United States Patent
Yang et al.

(10) Patent No.: US 10,106,578 B2
(45) Date of Patent: *Oct. 23, 2018

(54) MELANOCORTIN-1 RECEPTOR-SPECIFIC LINEAR PEPTIDES

(71) Applicant: Palatin Technologies, Inc., Cranbury, NJ (US)

(72) Inventors: Wei Yang, Edison, NJ (US); Yi-Qun Shi, East Brunswick, NJ (US)

(73) Assignee: Palatin Technologies, Inc., Cranbury, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/422,850

(22) Filed: Feb. 2, 2017

(65) Prior Publication Data

US 2017/0145056 A1    May 25, 2017

Related U.S. Application Data

(60) Continuation of application No. 14/585,686, filed on Dec. 30, 2014, now Pat. No. 9,580,466, which is a division of application No. 13/472,955, filed on May 16, 2012, now Pat. No. 8,933,194.

(51) Int. Cl.
*C07K 7/06* (2006.01)
*A61K 38/00* (2006.01)
*C07K 14/68* (2006.01)

(52) U.S. Cl.
CPC ............. *C07K 7/06* (2013.01); *C07K 14/68* (2013.01); *A61K 38/00* (2013.01)

(58) Field of Classification Search
CPC ........... C07K 7/06; C07K 14/68; A61K 38/00
See application file for complete search history.

(56) References Cited

U.S. PATENT DOCUMENTS

| | | | |
|---|---|---|---|
| 4,731,408 A | 3/1988 | Hadley et al. | |
| 5,576,290 A | 11/1996 | Hadley | |
| 5,674,839 A | 10/1997 | Hruby et al. | |
| 5,683,981 A | 11/1997 | Hadley et al. | |
| 5,714,576 A | 2/1998 | Hruby et al. | |
| 5,925,618 A | 7/1999 | Baumbach et al. | |
| 6,051,555 A | 4/2000 | Hadley | |
| 6,054,556 A | 4/2000 | Hruby et al. | |
| 6,265,162 B1 * | 7/2001 | Hoaki | C12Q 1/689 435/6.15 |
| 6,284,735 B1 | 9/2001 | Girten et al. | |
| 6,350,430 B1 | 2/2002 | Dooley et al. | |
| 6,476,187 B1 | 11/2002 | Cone et al. | |
| 6,534,503 B1 | 3/2003 | Dines et al. | |
| 6,579,968 B1 | 6/2003 | Blood et al. | |
| 6,600,015 B2 | 7/2003 | Chen et al. | |
| 6,613,874 B1 | 9/2003 | Mazur et al. | |
| 6,693,165 B2 | 2/2004 | Bednarek | |
| 6,693,184 B1 | 2/2004 | Howard et al. | |
| 6,699,873 B1 | 3/2004 | Maguire et al. | |
| 6,794,489 B2 | 9/2004 | Blood et al. | |
| 6,887,846 B2 | 5/2005 | Catania et al. | |
| 6,951,916 B2 | 10/2005 | Mazur et al. | |
| 7,008,925 B1 | 3/2006 | Szardenings | |
| 7,049,398 B1 | 5/2006 | Sharma et al. | |
| 7,084,111 B2 | 8/2006 | Haskell-Luevano | |
| 7,115,393 B2 | 10/2006 | Shu et al. | |
| 7,176,279 B2 | 2/2007 | Sharma et al. | |
| 7,226,910 B2 | 6/2007 | Wilson et al. | |
| 7,235,625 B2 | 6/2007 | Diamond et al. | |
| 7,342,089 B2 | 3/2008 | Sharma et al. | |
| 7,345,144 B2 | 3/2008 | Sharma et al. | |
| 7,368,433 B2 | 5/2008 | Haskell-Luevano et al. | |
| 7,396,814 B2 | 7/2008 | Sharma et al. | |
| 7,417,027 B2 | 8/2008 | Sharma et al. | |
| 7,473,760 B2 | 1/2009 | Sharma et al. | |
| 7,541,430 B2 | 6/2009 | Sensfuss et al. | |
| 7,582,610 B2 | 9/2009 | Haskell-Luevano | |
| 8,114,844 B2 | 2/2012 | Sharma et al. | |

(Continued)

FOREIGN PATENT DOCUMENTS

| | | |
|---|---|---|
| CA | 1340107 C | 10/1998 |
| CA | 2158425 C | 1/2003 |

(Continued)

OTHER PUBLICATIONS

Abdel-Malek, ZA et al., "alpha-MSH tripeptide analogs activate the melanocortin 1 receptor and reduce UV-induced DNA damage in human melanocytes", Pigment Cell Melanoma Res., Epub Jun. 23, 2009, Oct. 2009, 5:635-44.

Abdel-Malek, Zalfa A. et al., "Melanoma prevention strategy based on using tetrapeptide a-MSH analogs that protect human melanocytes from UV-induced DNA damage and cytotoxicity", The FASEB Journal, Jul. 2006, 20E888-E896.

Adan, Rah et al., "The MC4 Receptor and Control of Appetite", British Journal of Pharmacology, Oct. 16, 2006, 149:815-827.

Adan, Roger A. et al., "Characterization of melanocortin receptor ligands on cloned brain melanocortin receptors and on grooming behavior in the rat", European Journal of Pharmacology, 1999, 378:249-258.

(Continued)

*Primary Examiner* — Julie Ha
*Assistant Examiner* — Li N Komatsu
(74) *Attorney, Agent, or Firm* — Stephen A. Slusher

(57) ABSTRACT

Melanocortin receptor-specific linear peptides of the formula $$Z\text{-}Xaa^1\text{-}Xaa^2\text{-}Xaa^3\text{-}Xaa^4\text{-}Xaa^5\text{-}Xaa^6\text{-}Y \quad (VI)$$

or a pharmaceutically acceptable salt thereof, where Z, Y, $Xaa^1$, $Xaa^2$, $Xaa^3$, $Xaa^4$, $Xaa^5$, and $Xaa^6$ are as defined in the specification, compositions and formulations including peptides of the foregoing formula or salts thereof, and pharmaceutical compositions for preventing, ameliorating or treating melanocortin-1 receptor-mediated or responsive diseases, indications, conditions and syndromes.

7 Claims, No Drawings
Specification includes a Sequence Listing.

(56) References Cited

U.S. PATENT DOCUMENTS

| | | |
|---|---|---|
| 2001/0056179 A1 | 12/2001 | Chen et al. |
| 2002/0143141 A1 | 10/2002 | Chen et al. |
| 2003/0065921 A1 | 4/2003 | Millhauser et al. |
| 2003/0105024 A1 | 6/2003 | Cone et al. |
| 2003/0113263 A1 | 6/2003 | Marks et al. |
| 2003/0212002 A1 | 11/2003 | Haskell-Luevano et al. |
| 2004/0023859 A1 | 2/2004 | Mazur et al. |
| 2005/0026948 A1 | 2/2005 | Meade et al. |
| 2005/0038230 A1 | 2/2005 | Sharma et al. |
| 2005/0069911 A1 | 5/2005 | Lee |
| 2005/0130901 A1 | 6/2005 | Lipton et al. |
| 2005/0187164 A1 | 8/2005 | Pinel |
| 2005/0239711 A1 | 10/2005 | Chen et al. |
| 2006/0014676 A1 | 1/2006 | Sharma et al. |
| 2006/0105951 A1 | 5/2006 | Cunningham et al. |
| 2006/0111281 A1 | 5/2006 | Sharma et al. |
| 2006/0258590 A1 | 11/2006 | Haskell-Luevano |
| 2006/0293223 A1 | 12/2006 | Gadski et al. |
| 2007/0027091 A1 | 2/2007 | Conde-Frieboes et al. |
| 2007/0105759 A1 | 5/2007 | Flora et al. |
| 2007/0123453 A1 | 5/2007 | Heiman et al. |
| 2007/0244054 A1 | 10/2007 | Sensfuss et al. |
| 2007/0270411 A1 | 11/2007 | Szewczyk et al. |
| 2007/0293423 A1 | 12/2007 | Jungheim et al. |
| 2008/0039387 A1 | 2/2008 | Sensfuss et al. |
| 2009/0069224 A1 | 3/2009 | Sharma et al. |
| 2009/0069242 A1 | 3/2009 | Jonassen et al. |
| 2009/0305960 A1 | 12/2009 | Chen et al. |
| 2010/0311648 A1 | 12/2010 | Dodd et al. |

FOREIGN PATENT DOCUMENTS

| | | |
|---|---|---|
| CN | 1563076 A | 1/2005 |
| CN | 1709906 A | 12/2005 |
| WO | 92/00995 | 1/1992 |
| WO | 94/22460 | 10/1994 |
| WO | 97/40070 | 10/1997 |
| WO | 98/10068 | 3/1998 |
| WO | 98/27113 | 6/1998 |
| WO | 99/021571 | 5/1999 |
| WO | 99/54358 | 10/1999 |
| WO | 00/01730 | 1/2000 |
| WO | 00/05263 | 2/2000 |
| WO | 00/35952 | 6/2000 |
| WO | 00/58361 | 10/2000 |
| WO | 01/00224 | 1/2001 |
| WO | 01/30808 | 5/2001 |
| WO | 01/52880 | 7/2001 |
| WO | 01/74844 | 10/2001 |
| WO | 01/85930 | 11/2001 |
| WO | 01/90140 | 11/2001 |
| WO | 02/18437 | 3/2002 |
| WO | 02/26774 | 4/2002 |
| WO | 02/094873 | 11/2002 |
| WO | 03/006604 | 1/2003 |
| WO | 03/006620 A2 | 1/2003 |
| WO | 03/095474 | 11/2003 |
| WO | 04/005318 A2 | 1/2004 |
| WO | 04/005324 | 1/2004 |
| WO | 04/046166 A2 | 6/2004 |
| WO | 04/099246 | 11/2004 |
| WO | 05/000338 | 1/2005 |
| WO | 05/000339 A2 | 1/2005 |
| WO | 05/000877 A2 | 1/2005 |
| WO | 05/014617 | 2/2005 |
| WO | 05/030797 | 4/2005 |
| WO | 05/047251 A1 | 5/2005 |
| WO | 05/048967 | 6/2005 |
| WO | 05/060985 | 7/2005 |
| WO | 05/102377 | 11/2005 |
| WO | 06/012667 | 2/2006 |
| WO | 06/014552 | 2/2006 |
| WO | 06/032457 | 3/2006 |
| WO | 06/037188 | 4/2006 |
| WO | 06/048449 | 5/2006 |
| WO | 06/048450 | 5/2006 |
| WO | 06/048451 | 5/2006 |
| WO | 06/048452 | 5/2006 |
| WO | 06/060873 | 6/2006 |
| WO | 06/073771 | 7/2006 |
| WO | 06/076442 | 7/2006 |
| WO | 06/097526 | 9/2006 |
| WO | 06/129317 | 12/2006 |
| WO | 07/008684 A2 | 1/2007 |
| WO | 07/008704 A2 | 1/2007 |
| WO | 07/009894 | 1/2007 |
| WO | 07/027574 | 3/2007 |
| WO | 07/035474 | 3/2007 |
| WO | 08/056207 | 5/2008 |
| WO | 08/087186 | 7/2008 |
| WO | 08/087187 | 7/2008 |
| WO | 08/087188 | 7/2008 |
| WO | 08/087189 | 7/2008 |
| WO | 08/087190 | 7/2008 |
| WO | 08/135819 A1 | 11/2008 |
| WO | 08/142319 | 11/2008 |
| WO | 08/156677 A2 | 12/2008 |
| WO | 09/036243 A1 | 3/2009 |
| WO | 09/061411 A2 | 5/2009 |
| WO | 09/151383 | 12/2009 |
| WO | 09/152079 | 12/2009 |
| WO | 10/144341 | 12/2010 |
| WO | 11/063366 | 5/2011 |

OTHER PUBLICATIONS

Balbani, Aracy P. et al., "Recent developments for smoking cessation and treatment of nicotine dependence", Informa healthcare / Expert Opinion, 2007, 17:287-297.

Ballet, Steven et al., "Novel selective human melanocortin-3 receptor ligands: Use of the 4-amino-1,2,4,5-tetrahydro-2-benzazepin-3-one (Aba) scaffold", Bioorg Med. Chem. Lett., May 1, 2007, 17(9): 2492-2498.

Balse-Srinivasan, Preeti et al., "Structure-Activity Relationships of y-MSH Analogues at the Human Melanocortin MC3, MC4, and MC5 Receptors.", J. Med. Chem., Oct. 4, 2003, 46:4965-4973.

Bednarek, M. A. et al., "Cyclic analogs of alpha-melanocyte-stimulating hormone (aMSH) with high agonist potency and selectivity at human melanocortin receptor 1b", Peptides, 2008, 29:1010-1017.

Bednarek, Maria A. et al., "Analogs of lactam Derivatives of alpha-Melanotropin with Basic and Acidic Residues", Biochemical and Biophysical Research Communications, 2000, 272:23-28.

Bednarek, Maria A. et al., "Analogs of MTII, Lactam Derivatives of alpha-Melanotropin, Modified at the n-Terminus, and their selectivity at human melanocortin receptors 3, 4 and 5", Biochemical and Biophysical Research Communications, 1999, 261:209-213.

Bednarek, Maria A. et al., "Ligands of the melanocortin receptors, 2002-2003 update", Ashley publications / Expert Opinion, 2004, 14:327-336.

Chan, Ngai C. et al., "Molecular Modelling of B Turns in a Cyclic Melanotropin", J. Pharm. Pharmacol, 1996, 48:218-222.

Communication, "PCT/US2010/57700—Search Report", International Search Report, dated Feb. 8, 2011.

Gautron, Laurent et al., "Melanocortin-4 Receptor Expression in a Vago-vagal Circuitry Involved in Postprandial Functions", The Journal of Comparative Neurology, 2010, 518:6-24.

Giuliani, D. et al., "Selective melanocortin MC4 receptor agonists reverse haemorrhagic shock and prevent multiple organ damage", British Journal of Pharmacology, 2007, 150:595-603.

Grieco, Paolo et al., "Structure-activity studies of new melanocortin peptides containing an aromatic amino acid at the N-terminal position", Peptides, 27(2), Feb. 2006, 472-481.

Hadley, Mac E. et al., "The Proopiomelanocortin System", Annals New York Academy of Science, 2006, 1-21.

Han, G. et al., "Design of Novel Chimeric Melanotropin-Deltorphin Analogues, Discovery of the First Potent Human Melanocortin 1 Receptor Antagonist", J. Med. Chem., 2003, 46:810-819.

Haskell-Luevano, Carrie et al., "Discovery of Prototype Peptidomimetic Agonists at the Human Melanocortin Receptors MC1R and MC4R", J. Med. Chem., vol. 40, 1997, 2133-2139.

(56) References Cited

OTHER PUBLICATIONS

Holder, Jerry R. et al., "Structure-Activity Relationships of the Melanocortin Tetrapeptide Ac-His-DPhe-Arg-Trp-NH2 at the Mouse Melanocortin Receptors, 1.", J. Med. Chem., May 24, 2002, 45:2801-2810.

Hruby, V. J. et al., "A Highly Potent Cyclic alpha-MSH Antagonist Containing Naphthylalanine", Peptides: Chemistry, Structure and Biology, 1996, 364-365.

Hruby, V. J. et al., "Design of Potent and Specific Melanotropin Agonists and Antagonists: Investigating Ligands for New Receptors", Peptides, 1996, 485-486.

Hruby, Victor J. et al., "Cyclic Lactam a-Melanotropin Analogues of Ac-Nle(4)-cyclo[Asp(5),D-Phe(7),Lys(10)] a-Melanocyte-Stimulating Hormone-(4-10)-NH(2) with Bulky Aromatic Amino Acids at Position 7 Show High Antagonist Potency and Selectivity at Specific Melanocortin Receptors", J. Med. Chem., vol. 38, 1995, 3454-3461.

Kang, Liya et al., "A selective small molecule agonist of the melanocortin-1 receptor inhibits lipopolysaccharide-induced cytokine accumulation and leukocyte infiltration in mice", Journal of Leukocyte Biology, Oct. 2006, 80:897-904.

Koikov, L. N. et al., "Analogs of sub-nanomolar hMC1R agonist LK-184 [Ph(CH2)3CO-His-D-Phe-Arg-Trp-NH2]. An additional binding site within the human melanocortin receptor 1?", Bioorganic & Medicinal Chemistry Letters, 2004, 14:3997-4000.

Kokot, Agatha et al., "Systemic Sclerosis", Arthritis & Theumatism, a-melanocyte-stimulating hormone suppresses bleomycin-induced collagen synthesis and reduces tissue fibrosis in a mouse model of scleroderma: Melanocortin peptides as a novel treatment strategy for scleroderma?, Jan. 29, 2009, 60:2:592-603.

Maaser, Christian et al., "Role of the Melanocortin System in Inflammation", Ann. N.Y. Acad. Science, 2006, 1072:123-134.

Navarro, Montserrat, et al., "Effects of Melanocortin Receptor Activation and Blockade on Ethanol Intake: A Possible Role for the Melanocortin-4 Receptor", Alcohol Clin. Exp. Res., 2005, 29(6):949-957.

Nijenhuis, Wouter A. et al., "Accelerating sensory recovery after sciatic nerve crush: non-selective versus melanocortin MC4 receptor-selective peptides", European Journal of Pharmacology, 2004, 495:145-152.

Nijenhuis, Wouter A. et al., "Discovery and in vivo evaluation of new melanocortin-4 receptor-selective peptides", Peptides, 2003, 24:271-280.

Nogueiras, Ruben et al., "The central melanocortin system directly controls peripheral lipid metabolism", The Journal of Clinical Investigation, 2007, 117(11): 3475.

Nozawa, Dai et al., "Recent advances in the development of melanocortin-4 receptor ligands", informa healthcare / Expert Opinion, 2008, 18:403-427.

Oosterom, Julia et al., "Common Requirements for Melanocortin-4 Receptor Selectivity of Structurally Unrelated Melanocortin Agonist and Endogenous Antagonist, Agouti Protein", The Journal of Biological Chemistry, 2001, 278(2):931-936.

Schaaper, Wim M. et al., "Synthesis of cyclic alpha-MSH peptides", Letters in Peptide Science, 2008, 5:205-208.

Todorovic, Aleksandar et al., "A review of melanocortin receptor small molecule ligands", Peptides, 2005, 26:2026-2036.

Ujjainwalla, Feroze et al., "Small Molecule Ligands of the Human Melanocortin-4 Receptor", Current Topics in Medicinal Chemistry, 2007, 7:1068-1084.

Vrinten, Dorien H. et al., "Antagonism of the Melanocortin System Reduces Cold and Mechanical Allodynia in Mononeurophatic Rats", The Journal of Neuroscience, 2000, 20(21):8131-8137.

Wikberg, Jarl E. et al., "Targeting melanocortin receptors: an approach to treat weight disorders and sexual dysfunction", Nature Reviews Drug Discovery, 2008, 7:307-323.

Yan, Liang Z. et al., "Structure-Activity Relationships of B-MSH Derived Melanocortin-4 Receptor Peptide Agonists", Current Topics in Medicinal Chemistry, 2007, 7:1052-1067.

Adenylate cyclase, from http://www.ncbi.nlm.nih.gov/protein/914573712?report=genbank&log$=prottop&blast_r . . . , p. 1, accessed Dec. 18, 2015.

Ca(2+)-sensing receptor, from http://www.ncbi.nlm.nih.gov/protein/461089?report=genbank&log$=prottop&blast_rank . . . , p. 1, accessed Dec. 18, 2015.

Water, from http://www.biology-online.org/dictionary/Water, pp. 1-3, accessed Apr. 24, 2014.

Helicase-*Streptococcus pneumoniae*, from http://ncbi.nlm.nih.gov/protein/894790458?report=genbank&log$=prottop&blast_ra . . . , pp. 1-3, accessed Jul. 12, 2016.

Communication, Supplementary European Search Report, European Patent Application No. 10832345.2, published Oct. 2, 2013.

Asami, Taiji et al., Novel LH-RH receptor antagonists; design, synthesis, and antagonistic activities of cyclic pentapeptides, Peptide Science, Protein Research Foundation, Minoo, JP, vol. 35, Jan. 1, 1999, pp. 213-216, XP009172865, ISSN: 1344-7661, Tab. 1, cmpd. 21.

\* cited by examiner

MELANOCORTIN-1 RECEPTOR-SPECIFIC LINEAR PEPTIDES

CROSS-REFERENCE TO RELATED APPLICATIONS

This application is a continuation of U.S. Ser. No. 14/585,686, entitled "Melanocortin-1 Receptor-Specific Linear Peptides", filed Dec. 30, 2014, now U.S. Pat. No. 9,580,466, issued on Feb. 28, 2017; which in turn is a divisional of U.S. Ser. No. 13/472,955, entitled "Melanocortin-1 Receptor-Specific Linear Peptides", filed May 16, 2012, now U.S. Pat. No. 8,933,194, issued on Jan. 13, 2015; which in turn is a continuation of international Application No. PCT/US2010/057700, published as international Publication No. WO 2011/063367, entitled "Melanocortin-1 Receptor-Specific Linear Peptides", filed on Nov. 23, 2010; which in turn claimed priority to and the benefit of the filing of U.S. Provisional Patent Application Ser. No. 61/263,486 entitled "Melanocortin-1 Receptor-Specific Linear Peptides", filed on Nov. 23, 2009. The specification and claims of each of the foregoing applications are incorporated herein by reference.

BACKGROUND OF THE INVENTION

Field of the Invention (Technical Field)

The present invention relates to melanocortin receptor-specific linear peptides, particularly linear peptides selective and specific for the melanocortin-1 receptor, which may be used in the treatment of melanocortin-1 receptor-mediated or responsive diseases, indications, conditions and syndromes.

Description of Related Art

The following discussion refers to a number of publications by author(s) and year of publication, and that due to recent publication dates certain publications are not to be considered as prior art vis-a-vis the present invention. Discussion of such publications herein is given for more complete background and is not to be construed as an admission that such publications are prior art for patentability determination purposes.

A family of melanocortin receptor types and subtypes has been identified. Receptor types include melanocortin-1 (MC-1) receptor (MCR-1), commonly known to be expressed in normal human melanocytes and on melanoma cells, but which is also reported to be expressed in various other cells, including those involved in immune responses, such as monocytes, neutrophils, lymphocytes, dendritic cells, natural killer (NK) cells and endothelial cells. See generally, Kang, L., et al., "A selective small molecule agonist of melanocortin-1 receptor inhibits lipopolysaccharide-induced cytokine accumulation and leukocyte infiltration in mice," *J. Leuk. Biol.* 80:897-904 (2006), and references cited therein. A variety of human MCR-1 subtypes and variants are known, including those disclosed in U.S. Pat. Nos. 6,693,184 and 7,115,393. In addition to MCR-1, other melanocortin receptor types include melanocortin-2 receptor (MCR-2) for ACTH (adrenocorticotropin), expressed in cells of the adrenal gland, melanocortin-3 and melanocortin-4 (MC-4) receptors (MCR-3 and MCR-4), expressed primarily in cells in the hypothalamus, mid-brain and brain-stem, and melanocortin-5 receptor (MCR-5), expressed in a wide distribution of peripheral tissues.

The primary endogenous melanocortin agonist is the cyclic α-melanocyte-stimulating hormone ("α-MSH") peptide. Melanocortin receptor-specific peptides generally contain the central tetrapeptide sequence of native α-MSH, His$^6$-Phe$^7$-Arg$^8$-Trp$^9$ (SEQ ID NO:1), or a mimetic or variation thereof, including various substitutions at one or more positions (see, e.g., Hruby, V. J., et al., "Alpha-Melanotropin: the minimal active sequence in the frog skin bioassay," *J. Med. Chem.*, 30:2126-2130 (1987); Castrucci, A. M. L., et al., "Alpha-melanotropin: the minimal active sequence in the lizard skin bioassay," *Gen. Comp. Endocrinol.*, 73:157-163 (1989); Haskell-Luevano, C., et al., "Discovery of prototype peptidomimetic agonists at the human melanocortin receptors MC1R and MC4R," *J. Med. Chem.*, 40:2133-2139 (1997); Holder, J. R., et al., "Structure-activity relationships of the melanocortin tetrapeptide Ac-His-DPhe-Arg-Trp-NH$_2$. 1. Modifications at the His position," *J. Med. Chem.*, 45:2801-2810 (2002); Abdel-Malek, Z. A., et al., "Melanoma prevention strategy based on using tetrapeptide α-MSH analogs that protect human melanocytes from UV-induced DNA damage and cytotoxicity," *FASEB J.*, 20:E888-E896 (2006); Bednarek, M. A., et al., "Cyclic analogs of α-melanocyte-stimulating hormone (αMSH) with high agonist potency and selectivity at human melanocortin receptor 1b," *Peptides*, 29:1010-1017 (2008); Koikov, L. N., et al., "Analogs of subnanomolar hMC1R agonist LK-184 [Ph(CH$_2$)$_3$CO-His-D-Phe-Arg-Trp-NH$_2$]. An additional binding site with the human melanocortin receptor 1?" *Bioorg. Med. Chem. Lett.* 14:3997-4000 (2004); and Abdel-Malek, Z. A., et al., "Alpha-MSH tripeptide analogs activate the melanocortin 1 receptor and reduce UV-induced DNA damage in human melanocytes," *Pigment Cell Melanoma Res.* 22:635-44 (2009)).

Peptides or peptide-like compounds asserted to be specific for one or more melanocortin receptors are disclosed in U.S. Pat. Nos. 5,576,290, 5,674,839, 5,683,981, 5,714,576, 5,731,408, 6,051,555, 6,054,556, 6,284,735, 6,350,430, 6,476,187, 6,534,503, 6,600,015, 6,613,874, 6,693,165, 6,699,873, 6,887,846, 6,951,916, 7,008,925, 7,049,398, 7,084,111, 7,176,279, 7,473,760, and 7,582,610; in U.S. published patent application Publication Nos. 2001/0056179, 2002/0143141, 2003/0064921, 2003/0105024, 2003/0212002, 2004/0023859, 2005/0130901, 2005/0187164, 2005/0239711, 2006/0105951, 2006/0111281, 2006/0293223, 2007/0027091, 2007/0105759, 2007/0123453, 2007/0244054, 2008/0039387, and 2009/0069242; and in international patent applications nos. WO 98/27113, WO 99/21571, WO 00/05263, WO 99/54358, WO 00/35952, WO 00/58361, WO 01/30808, WO 01/52880, WO 01/74844, WO 01/85930, WO 01/90140, WO 02/18437, WO 02/26774, WO 03/006604, WO 2004/046166, WO 2005/000338, WO 2005/000339, WO 2005/000877, WO 2005/030797, WO 2005/060985, WO2006/048449, WO 2006/048450, WO 2006/048451, WO 2006/048452, WO 2006/097526, WO 2007/008684, WO 2007/008704, WO 2007/009894 and WO 2009/061411.

Notwithstanding the intense scientific and pharmaceutical interest in melanocortin receptor-specific peptides, there remains a need for highly selective and specific MCR-1 agonist peptides for use in pharmaceutical applications. It is against this background that the present invention was made.

BRIEF SUMMARY OF THE INVENTION

In one aspect, the invention provides a linear peptide of formula (I):

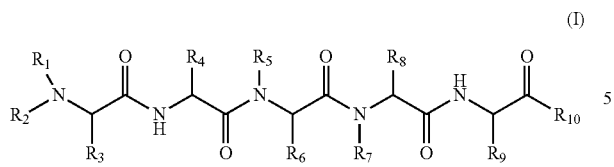

(I)

including all enantiomers, stereoisomers or diastereoisomers thereof, or a pharmaceutically acceptable salt of any of the foregoing, wherein:

$R_1$ is $-R_{11}-R_{12}$;

$R_2$ is $-H$, $-CH_3$ or $-CH_2-$, and if it is $-CH_2-$ forms with $R_3$ a ring of the general structure

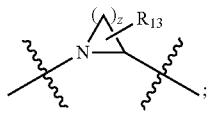
;

$R_3$ is $-H$, $-(CH_2)_z-$ if $R_2$ is $-CH_2-$, and if it is $-(CH_2)_z-$ forms the ring with $R_2$, or $R_3$ is $-(CH_2)_w-R_{14}-(CH_2)_w-R_{15}$, wherein any H in either $(CH_2)_w$ is optionally substituted with $-(CH_2)_w-CH_3$;

$R_4$ is $-(CH_2)_w-R_{16}$;

$R_5$ is $-H$, $-CH_3$ or $-CH_2-$, and if it is $-CH_2-$ forms with $R_6$ a ring of the general structure

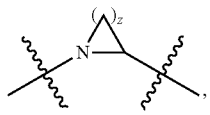
, wherein the ring is optionally substituted;

$R_6$ is $-(CH_2)_z-$ if $R_5$ is $-CH_2-$, and if it is $-(CH_2)_z-$ forms the ring with $R_5$, or $R_6$ is $-(CH_2)_w-R_{17}$;

$R_7$ is $-H$, $-CH_3$ or $-CH_2-$, and if it is $-CH_2-$ forms with $R_8$ a ring of the general structure

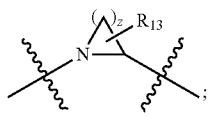
;

$R_8$ is $-H$, $-(CH_2)_z-$ if $R_7$ is $-CH_2-$, and if it is $-(CH_2)_z-$ forms the ring with $R_7$, or $R_8$ is a $C_1$-$C_{10}$ linear or branched alkyl, cycloalkyl or alkyl cycloalkyl;

$R_9$ is $-(CH_2)_w-R_{18}$;

$R_{10}$ is $-R_{11}-R_{19}$;

$R_{11}$ is in each instance independently optionally present, and if present, is in each instance independently from one to three L- or D-isomer amino acids, or a combination thereof;

$R_{12}$ is in each instance independently H or a $C_1$ to $C_7$ acyl group comprising a linear or branched alkyl, cycloalkyl, alkyl cycloalkyl, aryl or aralkyl;

$R_{13}$ is $-H$ or $-R_{14}-(CH_2)_w-R_{15}$;

$R_{14}$ is optionally present, and if present is
$-O-$,
$-S-$,
$-NH-$,
$-S(=O)_2-$,
$-S(=O)-$,
$-S(=O)_2-NH-$,
$-NH-S(=O)_2-$,
$-C(=O)-$,
$-C(=O)-O-$,
$-O-C(=O)-$,
$-NH-C(=O)-O-$,
$-O-C(=O)-NH-$,
$-NH-C(=O)-$, or
$-C(=O)-NH-$;

$R_{15}$ is
$-H$,
$-CH_3$,
$-N(R_{20a})(R_{20b})$,
$-NH-(CH_2)_z-N(R_{20a})(R_{20b})$,
$-NH-C(=NH)-N(R_{20a})(R_{20b})$,
$-NH-C(=O)-N(R_{20a})(R_{20b})$,
$-O(R_{20a})$,
$-(R_{20a})(R_{20b})$,
$-S(=O)_2(R_{20a})$
$-C(=O)-O(R_{20a})$

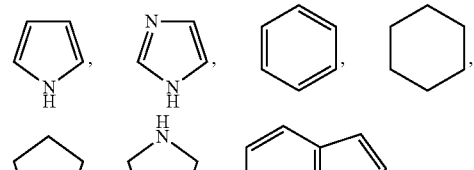

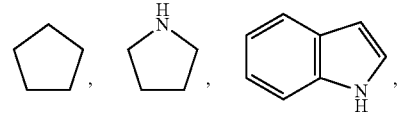

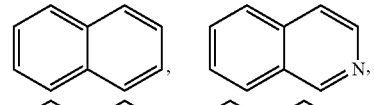

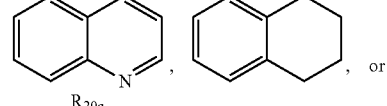
, or

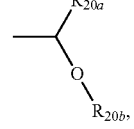
, wherein any ring in $R_{15}$ is optionally substituted with one or more ring substituents, and when one or more are present, are the same or different and independently hydroxyl, halogen, sulfonamide, alkyl, $-O$-alkyl, aryl, $-O$-aryl, $C(=O)-OH$, or $C(=O)-N(R_{20a})(R_{20b})$;

$R_{16}$ is substituted or unsubstituted aryl or heteroaryl;

$R_{17}$ is
$-H$,
$-N(R_{20a})(R_{20b})$,
$-NH-(CH_2)_z-N(R_{20a})(R_{20b})$,
$-NH-C(=NH)-N(R_{20a})(R_{20b})$,
$-NH-C(=O)-N(R_{20a})(R_{20b})$,
$-O(R_{20a})$,
$-C_1$ to $C_{17}$ linear, branched or cyclic alkyl chain,
$-C(=O)-N(R_{20a})(R_{20b})$,
$-S(=O)_2(R_{20a})$,

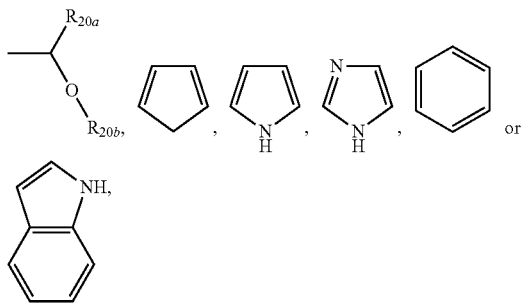

wherein any ring is optionally substituted with one or more optional ring substituents, and when one or more are present, are the same or different and independently hydroxyl, halogen, sulfonamide, alkyl, —O-alkyl, aryl, aralkyl, O-aralkyl, or —O-aryl;

$R_{18}$ is

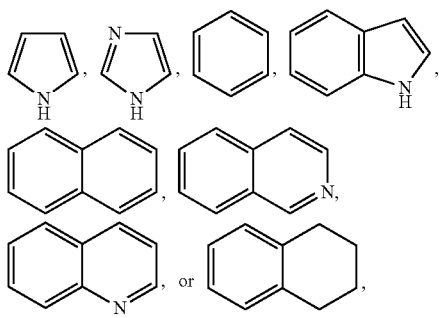

optionally substituted with one or more ring substituents, and when one or more are present, are the same or different and independently hydroxyl, halogen, sulfonamide, alkyl, —O-alkyl, aryl, or —O-aryl;

$R_{19}$ is —OH, —N($R_{20a}$)($R_{20b}$), —N($R_{20a}$)($CH_2$)$_w$-cycloalkyl, or —O—($CH_2$)$_w$-cycloalkyl;

$R_{20a}$ and $R_{20b}$ are each independently H or a $C_1$ to $C_4$ linear, branched or cyclic alkyl chain;

w is in each instance independently 0 to 5; and z is in each instance independently 1 to 5.

In the linear peptide of formula (I), $R_{16}$ may be substituted or unsubstituted phenyl, naphthyl or pyridyl. If $R_{16}$ is substituted phenyl, it may be substituted with between one and three ring substituents wherein the substituents are the same or different, and are each independently halo, ($C_1$-$C_{10}$)alkyl-halo, ($C_1$-$C_{10}$)alkyl, ($C_1$-$C_{10}$)alkoxy, ($C_1$-$C_{10}$)alkylthio, aryl, ($C_1$-$C_{10}$)alkylaryl, aryloxy, nitro, nitrile, sulfonamide, amino, monosubstituted amino, disubstituted amino, hydroxy, carbamoyl, carboxy, aryloxy-carbonyl, alkoxy-carbonyl, or aryloxy-carbonyl.

In the linear peptide of formula (I), the $R_{11}$ in —$R_{11}$-$R_{12}$ may be a single L- or D-isomer amino acid with an aliphatic side chain and the $R_{11}$ in $R_{11}$-$R_{19}$ may not be present. In the linear peptide of formula (I), $R_{11}$ in —$R_{11}$-$R_{12}$ may be a single L- or D-isomer amino acid with a side chain comprising at least one nitrogen atom. In the linear peptide of formula (I), $R_{11}$ in each instance may include at least one L- or D-isomer amino acid.

In another aspect, the invention provides a linear peptide of formula (II):

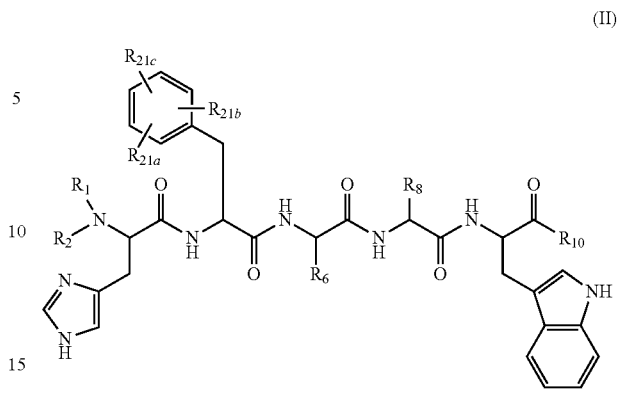

wherein:
substituents not otherwise defined are as defined for formula (I);

$R_{21a}$, $R_{21b}$ and $R_{21c}$ are independently in each instance hydrogen, halo, ($C_1$-$C_{10}$)alkyl-halo, ($C_1$-$C_{10}$)alkyl, ($C_1$-$C_{10}$)alkoxy, ($C_1$-$C_{10}$)alkylthio, aryl, ($C_1$-$C_{10}$)alkylaryl, aryloxy, nitro, nitrile, sulfonamide, amino, monosubstituted amino, disubstituted amino, hydroxy, carbamoyl, carboxy, aryloxy-carbonyl, alkoxy-carbonyl, or aryloxy-carbonyl;

$R_6$ is —($CH_2$)$_w$—N($R_{20a}$)($R_{20b}$), —($CH_2$)$_w$—NH($CH_2$)$_z$—N($R_{20a}$)($R_{20b}$), —($CH_2$)$_w$—NH—C(=NH)—N($R_{20a}$)($R_{20b}$) or —($CH_2$)$_w$—NH—C(=O)—N($R_{20a}$)($R_{20b}$); and $R_8$ is —H or $C_1$-$C_{10}$ linear or branched alkyl, cycloalkyl or alkyl cycloalkyl.

In the linear peptide of formula (II), $R_1$ may be —$R_{11}$-$R_{12}$ wherein $R_{11}$ comprises at least one L- or D-isomer amino acid and $R_2$ is H. Thus $R_1$ may be —$R_{11}$-$R_{12}$ wherein $R_{11}$ is an L- or D-isomer amino acid with a side chain comprising $C_1$-$C_{10}$ linear or branched alkyl and $R_{12}$ is a $C_1$ to $C_7$ acyl group comprising a linear or branched alkyl, cycloalkyl, alkyl cycloalkyl, aryl or aralkyl. If $R_{11}$ is an L- or D-isomer amino acid, then the side chain of $R_{11}$ may be —($CH_2$)$_3$—$CH_3$.

In another aspect the invention provides a linear peptide of formula (III).

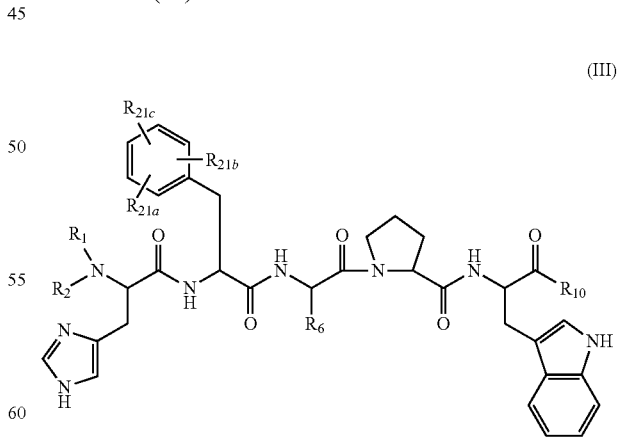

wherein:
substituents not otherwise defined are as defined for formula (I);

$R_{21a}$, $R_{21b}$ and $R_{21c}$ are independently in each instance hydrogen, halo, ($C_1$-$C_{10}$)alkyl-halo, ($C_1$-$C_{10}$)alkyl, ($C_1$-$C_{10}$)alkoxy, ($C_1$-$C_{10}$)alkylthio, aryl, ($C_1$-$C_{10}$)alkylaryl, aryloxy, nitro, nitrile, sulfonamide, amino, monosubstituted amino, disubstituted amino, hydroxy, carbamoyl, carboxy, aryloxy-carbonyl, alkoxy-carbonyl, or aryloxy-carbonyl; and $R_6$ is —$(CH_2)_w$—$N(R_{20a})(R_{20b})$, —$(CH_2)_w$—NH—$(CH_2)_z$—$N(R_{20a})(R_{20b})$, —$(CH_2)_w$—NH—C(=NH)—$N(R_{20a})(R_{20b})$ or —$(CH_2)_w$NH—C(=O)—$N(R_{20a})(R_{20b})$.

In the linear peptide of formula (III), $R_1$ may be —$R_{11}$-$R_{12}$ wherein $R_{11}$ comprises at least one L- or D-isomer amino acid and $R_2$ is H. Thus $R_1$ may be —$R_{11}$-$R_{12}$ wherein $R_{11}$ is an L- or D-isomer amino acid with a side chain comprising $C_1$-$C_{10}$ linear or branched alkyl and $R_{12}$ is a $C_1$ to $C_7$ acyl group comprising a linear or branched alkyl, cycloalkyl, alkyl cycloalkyl, aryl or aralkyl. If $R_{11}$ is an L- or D-isomer amino acid, then the side chain of $R_{11}$ may be —$(CH_2)_3$—$CH_3$.

In another aspect, the invention provides a linear peptide of formulas (IV) and (V):

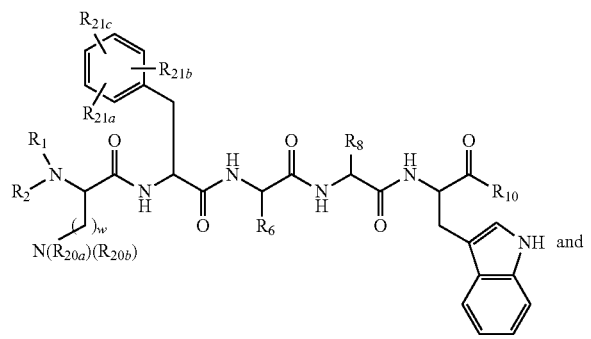

(IV)

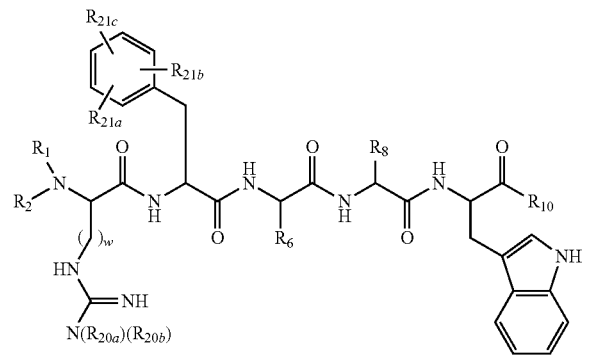

(V)

wherein substituents not otherwise defined are as defined for formula (I) and $R_{21a}$, $R_{21b}$ and $R_{21c}$ are independently in each instance hydrogen, halo, ($C_1$-$C_{10}$)alkyl-halo, ($C_1$-$C_{10}$) alkyl, ($C_1$-$C_{10}$)alkoxy, ($C_1$-$C_{10}$)alkylthio, aryl, ($C_1$-$C_{10}$) alkylaryl, aryloxy, nitro, nitrile, sulfonamide, amino, monosubstituted amino, disubstituted amino, hydroxy, carbamoyl, carboxy, aryloxy-carbonyl, alkoxy-carbonyl, or aryloxy-carbonyl.

In another aspect, the invention provides a linear peptide of formula (VI):

Z-$Xaa^1$-$Xaa^2$-$Xaa^3$-$Xaa^4$-$Xaa^5$-$Xaa^6$-Y      (VI)

or a pharmaceutically acceptable salt thereof, wherein:

Z is H or an N-terminal group;

$Xaa^1$ is optionally present, and if present is from one to three amino acid residues;

$Xaa^2$ is L- or D-Pro, optionally substituted with hydroxyl, halogen, sulfonamide, alkyl, —O-alkyl, aryl, alkyl-aryl, alkyl-O-aryl, alkyl-O-alkyl-aryl, or —O-aryl, or $Xaa^2$ is an L- or D-isomer amino acid with a side chain including at least one primary amine, secondary amine, alkyl, cycloalkyl, cycloheteroalkyl, aryl, heteroaryl, ether, sulfide, or carboxyl;

$Xaa^3$ is an L- or D-isomer amino acid with a side chain including phenyl or naphthyl, optionally substituted with one or more substituents independently selected from halo, ($C_1$-$C_{10}$)alkyl-halo, ($C_1$-$C_{10}$)alkyl, ($C_1$-$C_{10}$)alkoxy, ($C_1$-$C_{10}$)alkylthio, aryl, aryloxy, nitro, nitrile, sulfonamide, amino, monosubstituted amino, disubstituted amino, hydroxy, carboxy, and alkoxy-carbonyl;

$Xaa^4$ is L- or D-Pro or $Xaa^4$ is an L- or D-isomer amino acid with a side chain including at least one primary amine, secondary amine, guanidine, urea, alkyl, cycloalkyl, cycloheteroalkyl, aryl, heteroaryl, or ether;

$Xaa^5$ is Gly, Sar, an L- or D-isomer of Pro, or an amino acid with a side chain consisting of linear or branched alkyl, cycloalkyl, alkylcycloalkyl, aryl, or alkylaryl, $Xaa^6$ is an L- or D-amino acid with a side chain including at least one aryl or heteroaryl; and Y is a C-terminal group.

In the linear peptide of formula (VI) $Xaa^4$ may be D-Phe.

In the linear peptide of formula (VI) the N-terminal group may be a $C_1$ to $C_7$ acyl group, a linear or branched $C_1$ to $C_{17}$ alkyl, aryl, heteroaryl, alkene, alkenyl, or aralkyl chain or an N-acylated linear or branched $C_1$ to $C_{17}$ alkyl, aryl, heteroaryl, alkene, alkenyl, or aralkyl chain.

In the linear peptide of formula (VI) Y may be a hydroxyl, an amide, or an amide substituted with one or two linear or branched $C_1$ to $C_{17}$ alkyl, cycloalkyl, aryl, alkyl cycloalkyl, aralkyl, heteroaryl, alkene, alkenyl, or aralkyl chains.

In another aspect, the invention provides the linear peptide of formula (VI) wherein:

Z is H or a $C_1$ to $C_7$ acyl N-terminal group;

$Xaa^1$ is Gly or an L- or D-isomer of Ala, Nle, Leu, Ile or Val;

$Xaa^2$ is an L- or D-isomer of Ala, His or Pro, optionally substituted with hydroxyl, halogen, sulfonamide, alkyl, —O-alkyl, aryl, alkyl-aryl, alkyl-O-aryl, alkyl-O-alkyl-aryl, or —O-aryl;

$Xaa^3$ is L- or D-Phe, optionally substituted with one or more substituents independently selected from halo, ($C_1$-$C_{10}$)alkyl-halo, ($C_1$-$C_{10}$)alkyl, ($C_1$-$C_{10}$)alkoxy, ($C_1$-$C_{10}$) alkylthio, aryl, aryloxy, nitro, nitrile, sulfonamide, amino, monosubstituted amino, disubstituted amino, hydroxy, carboxy, and alkoxy-carbonyl;

$Xaa^4$ is an L- or D-isomer of Arg, His, Ser, Thr, Lys, HLys, Cit, Met(O), Orn, Dap, or Dab;

$Xaa^5$ is Gly, Sar or an L- or D-isomer of Ala or Pro, $Xaa^6$ is L- or D-Trp; and Y is a hydroxyl, an amide, or an amide substituted with one or two linear or branched $C_1$ to $C_{17}$ alkyl, cycloalkyl, aryl, alkyl cycloalkyl, aralkyl, heteroaryl, alkene, alkenyl, or aralkyl chains.

In another aspect, the invention provides a pharmaceutical composition comprising a linear peptide or pharmaceutically acceptable salt thereof of formula (I), (II), (III), (IV), (V) or (VI) and a pharmaceutically acceptable carrier.

In another aspect, the invention provides a method for treatment of a melanocortin receptor-mediated disease, indication, condition or syndrome in a human or non-human mammal, comprising the step of administering the pharmaceutical composition comprising a linear peptide or pharmaceutically acceptable salt thereof of formula (I), (II), (III), (IV), (V) or (VI) and a pharmaceutically acceptable carrier.

In another aspect, the invention provides a method for treating a condition responsive to changes in melanocortin receptor function in a human or non-human mammal, comprising the step of administering the pharmaceutical composition comprising a linear peptide or pharmaceutically acceptable salt thereof of formula (I), (II), (III), (IV), (V) or (VI) and a pharmaceutically acceptable carrier.

In another aspect, the present invention provides a melanocortin receptor-specific peptide-based pharmaceutical composition for use in treatment of melanocortin receptor-mediated diseases, indications, conditions and syndromes.

In another aspect, the present invention provides a peptide-based melanocortin receptor-specific pharmaceutical, wherein the peptide is a selective MCR-1 ligand, for use in treatment of MCR-1 associated disorders, diseases, indications, conditions and/or syndromes.

In another aspect, the present invention provides peptides which are specific for melanocortin receptor MCR-1 and which are agonists.

In another aspect, the present invention provides a melanocortin receptor-specific pharmaceutical for use in treatment wherein administration of the treatment is via pulmonary administration.

In another aspect, the present invention provides specific MCR-1 linear peptides that are effective over a significant dose range.

Yet another aspect of the present invention provides specific MCR-1 linear peptides which, because of increased efficacy at low doses, may be administered by delivery systems other than art conventional intravenous, subcutaneous or intramuscular injection, including but not limited to oral delivery systems, inhalation delivery systems, pulmonary delivery systems, nasal delivery systems and mucous membrane delivery systems.

Other aspects and novel features, and the further scope of applicability of the present invention will be set forth in part in the detailed description to follow, and in part will become apparent to those skilled in the art upon examination of the following, or may be learned by practice of the invention. The aspects of the invention may be realized and attained by means of the instrumentalities and combinations particularly pointed out in the appended claims.

DETAILED DESCRIPTION OF THE INVENTION 1.0 Definitions

Before proceeding with the description of the invention, certain terms are defined as set forth herein.

In the sequences given for the peptides according to the present invention, the amino acid residues have their conventional meaning as given in Chapter 2400 of the *Manual of Patent Examining Procedure* 8$^{th}$ Ed. Thus, "Nle" is norleucine, "Asp" is aspartic acid, "His" is histidine, "Phe" is phenylalanine, "Arg" is arginine, "Trp" is tryptophan, and "Lys" is lysine, and so on. It is to be understood that "D" isomers are designated by a "D-" before the three letter code or amino acid name, such that for example D-Phe is D-phenylalanine. Amino acid residues not encompassed by the foregoing have the following definitions:

| Abbreviation | Common Name | Side Chain or Amino Acid Structure |
| --- | --- | --- |
| Aib | alpha-aminoisobutyric acid | |
| Cit | citrulline | |
| Dab | diaminobutyric acid | |
| Dap | diaminoproprionic acid | |
| hGlu | homoglutamic acid | |
| Hyp | hydroxyproline | |
| Hyp(Bzl) | O-benzyl-hydroxyproline | |
| Nal 1 | 3-(1-naphthyl)alanine | |
| Nal 2 | 3-(2-naphthyl)alanine | |
| Nle | norleucine | |
| Orn | ornithine | |

| Abbreviation | Common Name | Side Chain or Amino Acid Structure |
|---|---|---|
| Pro(4-Bzl) | 4-benzyl-proline | 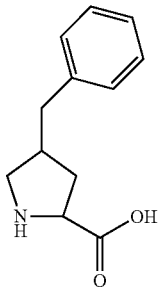 [SMILES: O=C(O)C1CC(Cc2ccccc2)CN1] |
| Pro(4-NH$_2$) | 4-amino-proline | 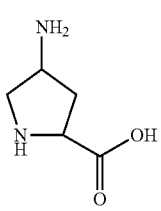 |
| Sar | sarcosine | 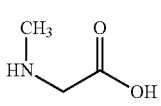 |

An "α, α-disubstituted amino acid" means any α-amino acid having a further substituent in the α-position, which substituent may be the same as or different from the side chain moiety of the α-amino acid. Suitable substituents, in addition to the side chain moiety of the α-amino acid, include $C_1$ to $C_6$ linear or branched alkyl. Aib is an example of an α, α-disubstituted amino acid. While α, α-disubstituted amino acids can be referred to using conventional L- and D-isomeric references, it is to be understood that such references are for convenience, and that where the substituents at the α-position are different, such amino acid can interchangeably be referred to as an α, α-disubstituted amino acid derived from the L- or D-isomer, as appropriate, of a residue with the designated amino acid side chain moiety. Thus (S)-2-Amino-2-methyl-hexanoic acid can be referred to as either an α, α-disubstituted amino acid derived from L-Nle or as an α, α-disubstituted amino acid derived from D-Ala. Similarly, Aib can be referred to as an α, α-disubstituted amino acid derived from Ala. Whenever an α, α-disubstituted amino acid is provided, it is to be understood as including all (R) and (S) configurations thereof. Whenever a claim or description herein refers to an "amino acid", such designation includes, but is not limited to, an "α, α-disubstituted amino acid."

An "N-substituted amino acid" means any amino acid wherein an amino acid side chain moiety is covalently bonded to the backbone amino group, including optionally where there are no substituents other than H in the α-carbon position. Sarcosine is an example of an N-substituted amino acid. By way of example, sarcosine can be referred to as an N-substituted amino acid derivative of Ala, in that the amino acid side chain moiety of sarcosine and Ala is the same, methyl. Whenever a claim or description herein refers to an "amino acid", such designation includes, but is not limited to, an "N-substituted amino acid."

The term "alkane" includes linear or branched saturated hydrocarbons. Examples of linear alkane groups include methane, ethane, propane, and the like. Examples of branched or substituted alkane groups include methylbutane or dimethylbutane, methylpentane, dimethylpentane or trimethylpentane, and the like. In general, any alkyl group may be a substitutent of an alkane.

The term "alkene" includes unsaturated hydrocarbons that contain one or more double carbon-carbon bonds. Examples of such alkene groups include ethylene, propene, and the like.

The term "alkenyl" includes a linear monovalent hydrocarbon radical of two to six carbon atoms or a branched monovalent hydrocarbon radical of three to six carbon atoms containing at least one double bond; examples thereof include ethenyl, 2-propenyl, and the like.

The "alkyl" groups specified herein include those alkyl radicals of the designated length in either a straight or branched configuration. Examples of such alkyl radicals include methyl, ethyl, propyl, isopropyl, butyl, sec-butyl, tertiary butyl, pentyl, isopentyl, hexyl, isohexyl, and the like.

The term "alkyne" includes a linear monovalent hydrocarbon radical of two to six carbon atoms or a branched monovalent hydrocarbon radical of three to six carbon atoms containing at least one triple bond; examples thereof include ethyne, propyne, butyne, and the like.

The term "aryl" includes a monocyclic or bicyclic aromatic hydrocarbon radical of 6 to 12 ring atoms, and optionally substituted independently with one or more substituents selected from alkyl, haloalkyl, cycloalkyl, alkoxy, alkythio, halo, nitro, acyl, cyano, amino, monosubstituted amino, disubstituted amino, hydroxy, carboxy, or alkoxycarbonyl. Examples of an aryl group include phenyl, biphenyl, naphthyl, 1-naphthyl, and 2-naphthyl, derivatives thereof, and the like.

The term "aralkyl" includes a radical —$R^aR^b$ where $R^a$ is an alkylene (a bivalent alkyl) group and $R^b$ is an aryl group as defined above. Examples of aralkyl groups include benzyl, phenylethyl, 3-(3-chlorophenyl)-2-methylpentyl, and the like.

The term "aliphatic" includes compounds with hydrocarbon chains, such as for example alkanes, alkenes, alkynes, and derivatives thereof.

The term "acyl" includes a group R(C=O)—, where R is an organic group. An example is the acetyl group $CH_3$—C (=O)—, referred to herein as "Ac".

A peptide or aliphatic moiety is "acylated" when an alkyl or substituted alkyl group as defined above is bonded through one or more carbonyl {—(C=O)—} groups. A peptide is most usually acylated at the N-terminus.

An "omega amino aliphatic chain" includes an aliphatic moiety with a terminal amino group. Examples of omega amino aliphatic chains include aminoheptanoyl and the amino acid side chain moieties of ornithine and lysine.

The term "heteroaryl" includes mono- and bicyclic aromatic rings containing from 1 to 4 heteroatoms selected from nitrogen, oxygen and sulfur. 5- or 6-membered heteroaryl are monocyclic heteroaromatic rings; examples thereof include thiazole, oxazole, thiophene, furan, pyrrole, imidazole, isoxazole, pyrazole, triazole, thiadiazole, tetrazole, oxadiazole, pyridine, pyridazine, pyrimidine, pyrazine, and the like. Bicyclic heteroaromatic rings include, but are not limited to, benzothiadiazole, indole, benzothiophene, benzofuran, benzimidazole, benzisoxazole, benzothiazole, quinoline, benzotriazole, benzoxazole, isoquinoline, purine, furopyridine and thienopyridine.

An "amide" includes compounds that have a trivalent nitrogen attached to a carbonyl group (—C(=O)—NH$_2$), such as for example methylamide, ethylamide, propylamide, and the like.

An "imide" includes compounds containing an imido group (—C(=O)—NH—C(=O)—).

An "amine" includes compounds that contain an amino group (—NH₂).

A "nitrile" includes compounds that contain a (—CN) group bound to an organic group.

The term "halogen" includes the halogen atoms fluorine, chlorine, bromine and iodine, and groups including one or more halogen atoms, such as —CF₃ and the like.

The term "composition", as in pharmaceutical composition, encompasses a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions utilized in the present invention encompass any composition made by admixing an active ingredient and one or more pharmaceutically acceptable carriers.

By a melanocortin receptor "agonist" is meant an endogenous substance, drug substance or compound, including a compound such as the peptides of the present invention, which can interact with a melanocortin receptor and initiate a pharmacological response, including but not limited to adenyl cyclase activation, characteristic of the melanocortin receptor. For the present invention, a melanocortin receptor agonist which is an agonist at MCR-1 is preferred.

By "α-MSH" is meant the peptide Ac-Ser-Tyr-Ser-Met-Glu-His-Phe-Arg-Trp-Gly-Lys-Pro-Val-NH₂ (SEQ ID NO:2) and analogs and homologs thereof, including without limitation NDP-α-MSH.

By "NDP-α-MSH" is meant the peptide Ac-Ser-Tyr-Ser-Nle-Glu-His-D-Phe-Arg-Trp-Gly-Lys-Pro-Val-NH₂ (SEQ ID NO:3) and analogs and homologs thereof.

By "EC₅₀" is meant the molar concentration of an agonist, including a partial agonist, which produced 50% of the maximum possible response for that agonist. By way of example, a test compound which, at a concentration of 72 nM, produces 50% of the maximum possible response for that compound as determined in a cAMP assay in an MCR-1 cell expression system has an EC₅₀ of 72 nM. Unless otherwise specified, the molar concentration associated with an EC₅₀ determination is in nanomoles per liter (nM).

By "Ki (nM)" is meant the equilibrium inhibitor dissociation constant representing the molar concentration of a competing compound that binds to half the binding sites of a receptor at equilibrium in the absence of radioligand or other competitors. In general, the numeric value of the Ki is inversely correlated to the affinity of the compound for the receptor, such that if the Ki is low, the affinity is high. Ki may be determined using the equation of Cheng and Prusoff (Cheng Y., Prusoff W. H., Biochem. Pharmacol. 22: 3099-3108, 1973):

$$K_i = \frac{EC_{50}}{1 + \frac{[ligand]}{K_D}}$$

where "ligand" is the concentration of radioligand and $K_D$ is an inverse measure of receptor affinity for the radioligand which produces 50% receptor occupancy by the radioligand. Unless otherwise specified, the molar concentration associated with a Ki determination is in nM. Ki may be expressed in terms of specific receptors (e.g., MCR-1, MCR-3, MCR-4 or MCR-5), specific species (e.g., human or murine), and specific ligands (e.g., α-MSH or NDP-α-MSH).

By "inhibition" is meant the percent attenuation, or decrease in receptor binding, in a competitive inhibition assay compared to a known standard. Thus, by "inhibition at 1 µM (NDP-α-MSH)" is meant the percent decrease in binding of NDP-α-MSH by addition of a determined amount of the compound to be tested, such as 1 µM of a test compound, such as under the assay conditions hereafter described. By way of example, a test compound that does not inhibit binding of NDP-α-MSH has a 0% inhibition, and a test compound that completely inhibits binding of NDP-α-MSH has a 100% inhibition. Typically, as described hereafter, a radio assay is used for competitive inhibition testing, such as with I¹²⁵-labeled NDP-α-MSH, or a lanthanide chelate fluorescent assay, such as with Eu-NDP-α-MSH. However, other methods of testing competitive inhibition are known, including use of label or tag systems other than radioisotopes, and in general any method known in the art for testing competitive inhibition may be employed in this invention. It may thus be seen that "inhibition" is one measure to determine whether a test compound attenuates binding of α-MSH to melanocortin receptors.

By "binding affinity" is meant the ability of a compound or drug to bind to its biological target, expressed herein as Ki (nM).

In general, "functional activity" is a measure of the signaling of a receptor, or measure of a change in receptor-associated signaling, such as a melanocortin receptor, and in particular MCR-1 or hMCR-1, upon activation by a compound. Melanocortin receptors initiate signal transduction through activation of heterotrimeric G proteins. In one aspect, melanocortin receptors signal through $G\alpha_s$, which catalyzes production of cAMP by adenylyl cyclase. Thus determination of stimulation of adenylyl cyclase, such as determination of maximal stimulation of adenylyl cyclase, is one measure of functional activity, and is the primary measure exemplified herein. However, it is to be understood that alternative measures of functional activity may be employed in the practice of this invention, and are specifically contemplated and included within the scope of this invention. Thus, in one example intracellular free calcium may be measured, such as reported by and using the methods disclosed in Mountjoy, K. G., et al., "Melanocortin receptor-medicated mobilization of intracellular free calcium in HEK293 cells," Physiol. Genomics 5:11-19 (2001), or Kassack, M. U., et al., "Functional screening of G protein-coupled receptors by measuring intracellular calcium with a fluorescence microplate reader," Biomol. Screening 7:233-246 (2002). It is also possible to measure activation by measurement of the production of inositol triphosphate or diacylglycerol from phosphatidylinositol 4,5-biphosphate, such as by use of radioassays. Yet another measure of functional activity is receptor internalization, resulting from activation of regulatory pathways, such as using the methods disclosed in Nickolls, S. A., et al., "Functional selectivity of melanocortin 4 receptor peptide and nonpeptide agonists: evidence for ligand specific conformational states," J. Pharm. Exper. Therapeutics 313:1281-1288 (2005). Yet another measure of functional activity is the exchange, and exchange rate, of nucleotides associated with activation of a G protein receptor, such as the exchange of GDP (guanosine diphosphate) for GTP (guanosine triphosphase) on the G protein α subunit, which may be measured by any number of means, including a radioassay using guanosine 5'-(γ-[³⁵S] thio)-triphosphate, as disclosed in Manning, D. R., "Measures of efficacy using G proteins as endpoints: differential engagement of G proteins through single receptors," *Mol. Pharmacol.* 62:451-452 (2002). Various gene-based assays have been developed for measuring activation of G-coupled proteins, such as those disclosed in Chen, W., et al., "A colorimetric assay from measuring activation of Gs- and Gq-coupled signaling pathways," *Anal. Biochem.* 226:349-354 (1995); Kent, T. C., et al., "Development of a generic dual-reporter gene assay for screening G-protein-coupled receptors," *Biomol Screening* 5:437-446 (2005); or Kotarsky, K., et al., "Improved receptor gene assays used to identify ligands acting on orphan seven-transmembrane receptors," *Pharmacology & Toxicology* 93:249-258 (2003). The colorimetric assay of Chen et al. has been adapted for use in measuring melanocortin receptor activation, as disclosed in Hruby, V. J., et al., "Cyclic lactam α-melanocortin analogues of Ac-Nle$^4$-cyclo[Asp$^5$,D-Phe$^7$,Lys$^{10}$] α-melanocyte-stimulating hormone-(4-10)-NH$_2$ with bulky aromatic amino acids at position 7 shows high antagonist potency and selectivity at specific melanocortin receptors," *J. Med. Chem.*, 38:3454-3461 (1995). In general, functional activity may be measured by any method, including methods of determining activation and/or signaling of a G-coupled receptor, and further including methods which may be hereafter developed or reported. Each of the foregoing articles, and the methods disclosed therein, is incorporated here by reference as if set forth in full.

The terms "treat," "treating" and "treatment," as used herein, contemplate an action that occurs while a patient is suffering from the specified disease or disorder, which reduces the severity of the disease or disorder.

As used herein, the term "therapeutically effective amount" means the amount of a compound including a peptide of the invention that will elicit a biological or medical response in the mammal that is being treated by a medical doctor or other clinician.

As used herein, the term "prophylactically effective" or "preventive" means the amount of a compound including a peptide of the invention that will prevent or inhibit affliction or mitigate affliction of a mammal with a medical condition that a medical doctor or other clinician is trying to prevent, inhibit, or mitigate before a patient begins to suffer from the specified disease or disorder.

By "circulatory shock" is meant the general medical condition in which organs and/or tissues of the body of the subject, which subject may be human or animal, are not receiving an adequate flow of blood. Circulatory shock includes conditions such as hypovolemic shock, cardiogenic shock, vasodilatory shock and the like. These conditions or dysfunctions in circulation can in turn have different causes, such as bacterial blood infection (septic shock or infectious), severe allergic reaction (anaphylactic shock), trauma (traumatic shock), severe bleeding or loss of blood (hemorrhagic shock), neurologic dysfunction causing abnormal opening of blood vessels (neurogenic shock) or endocrine related (endocrine shock). Circulatory shock can further result in ischemia and ischemic damage to bodily organs, tissues, cells or parts. Upon reperfusion, or restoration of blood flow, ischemia-reperfusion injury can occur, also resulting in damage to bodily organs, tissues, or cells.

By "inflammatory disease," also sometimes called an "inflammatory condition," is meant a disease or condition characterized in part by inflammatory mechanisms, such as specific T lymphocyte reactions or antibody-antigen interactions causing the recruitment of inflammatory cells and endogenous mediator chemicals, including but not limited to cytokines, which mediator chemicals include but are not limited to one or more of increased NF-κB activity, increased TNF-α production, increased IL-1 production and increased IL-6 production.

2.0 Clinical Indications and Utility

The compositions and methods disclosed herein can be used for both medical applications and animal husbandry or veterinary applications. Typically, the methods are used in humans, but may also be used in other mammals. The term "patient" denotes a mammalian individual, and is so used throughout the specification and in the claims. The primary applications of the present invention involve human patients, but the present invention may be applied to laboratory, farm, zoo, wildlife, pet, sport or other animals. Clinical indications and specific utilities include the following:

2.1 Inflammatory Diseases, Indications, Conditions and Syndromes.

Peptides, compositions and methods of the present invention are directed towards the treatment of inflammatory diseases and inflammatory conditions in a subject. There are a number of inflammatory diseases and inflammatory conditions which may be so treated. In one aspect, the inflammatory condition results from a disease including a form of arthritis, including but not limited to osteoarthritis, rheumatoid arthritis, septic arthritis, gout and pseudogout, juvenile idiopathic arthritis, Still's disease and ankylosing spondylitis, as well as arthritis secondary to other diseases, such as arthritis secondary to lupus erythematosus, Henoch-Schonlein purpura, psoriatic arthritis, reactive arthritis, haemochromatosis, hepatitis, Wegener's granulomatosis, vasculitis syndromes, Lyme disease, familial Mediterranean fever, hyperimmunoglobulinemia D with recurrent fever, TNF receptor-associated periodic syndrome and inflammatory bowel disease, including Crohn's disease and ulcerative colitis. In another aspect, the inflammatory condition results from a disease including a form of inflammatory bowel disease, such as Crohn's disease, ulcerative colitis, collagenous colitis, lymphocytic colitis, ischemic colitis, diversion colitis, Behçet's syndrome, infective colitis and indeterminate colitis. In another aspect, the inflammatory condition results from an autoimmune disease, including but not limited to systemic syndromes such as systemic lupus erythematosus, Sjögren's syndrome, scleroderma, rheumatoid arthritis and polymyositis, or a syndrome affecting only a local body system, such as the endocrine system (diabetes mellitus type 1, Hashimoto's thyroiditis, Addison's disease, etc.), dermatologic system (pemphigus vulgaris), hematologic system (autoimmune hemolytic anemia), or neural system (multiple sclerosis). Thus autoimmune diseases include, in addition to the general syndromes discussed above, such diseases and conditions as acute disseminated encephalomyelitis, Addison's disease, ankylosing spondylitis, antiphospholipid antibody syndrome, aplastic anemia, autoimmune hepatitis, autoimmune oophoritis, celiac disease, Crohn's disease, gestational pemphigoid, Goodpasture's syndrome, Graves' disease, Guillain-Barré syndrome, Hashimoto's disease, idiopathic thrombocytopenic purpura, Kawasaki disease, lupus erythematosus, mixed connective tissue disease, multiple sclerosis, myasthenia gravis, opsoclonus myoclonus syndrome, optic neuritis, Ord's thyroiditis, pemphigus, pernicious anaemia, primary biliary cirrhosis, Reiter's syndrome, Sjögren's syndrome, Takayasu's arteritis, temporal arteritis, autoimmune hemolytic anemia and Wegener's granulomatosis.

In another aspect, the inflammatory condition results from or is related to chronic obstructive pulmonary disease (COPD), also known as chronic obstructive airway diseases, including but not limited to diseases characterized by the pathological limitation of airflow in the airway that is not fully reversible, such as for example chronic bronchitis, emphysema, pneumoconiosis, pulmonary neoplasms and other lung disorders. Other inflammatory conditions include upper or lower airway diseases and disorders, such as allergic asthma, non-allergic asthma, allergic rhinitis, vasomotor rhinitis, allergic conjunctivitis, non-allergic conjunctivitis, and the like, as well as airway diseases related to external toxins or substances, such as various forms of pneumoconiosis (coalworkers pneumoconiosis, asbestosis, silicosis, bauxite fibrosis, berylliosis, or siderosis), byssinosis or hypersensitivity pneumonitis (farmers lung or bird fanciers lung). Other lung diseases involving an inflammatory condition include acute respiratory distress syndrome. The peptides and compositions of the present invention are of particular utility for treatment of conditions wherein glucocorticoids are either ineffectual or inadequate to bring about the desired pharmacological response, such as COPD, asthma in individuals who smoke, and other conditions characterized, in whole or in part, by eosinophil accumulation in the lung, neutrophil infiltration and activation, alveolar macrophage recruitment and activation, epithelial cell expression of IL-8 or increased expression of TNF-$\alpha$. For airway or lung disorders, in one aspect the peptides of the present invention are delivered systemically; in another aspect the peptides of the present invention are delivered locally, such as by inhalation administration.

In yet another aspect, the inflammatory condition results from or is related to some form of transplant-related condition or syndrome, such as graft-versus-host disease, hyperacute rejection, acute rejection, or chronic rejection. Graft-versus-host disease is a common complication of allogeneic bone marrow transplantation, but can occur with other transplantations, and particularly those with T cells present in the graft, either as contaminants or intentionally introduced. Hyperacute, acute or chronic rejection can occur with bodily organs such as kidneys, liver, pancreas, spleen, uterus, heart or lungs, as well as transplantation of bone, cornea, face, hand, penis or skin. In one embodiment, a pharmaceutical composition including one or more of the peptides of the present invention is given prophylactically to limit or prevent a transplant-related condition or syndrome, such as immediately before, during or after transplantation of a bodily fluid, organ or part. In another embodiment, the bodily fluid, organ or part being transplanted is perfused with a solution of a pharmaceutical composition including one or more of the peptides of the present invention. In yet another embodiment, one or more of the peptides of the present invention are administered in conjunction with, combination with or series with one or more other agents for transplant rejection, such as calcineurin inhibitors including cyclosporin or tacrolimus, mTOR inhibitors including sirolimus or everolimus, anti-proliferatives including azathioprine or mycophenolic acid, corticosteroids including prednisolone or hydrocortisone, antibodies such as monoclonal anti-IL-2R$\alpha$ receptor antibodies, basiliximab or daclizumab, or polyclonal anti-T-cell antibodies such as anti-thymocyte globulin or anti-lymphocyte globulin.

2.2 Fibrotic and Sclerotic Diseases, Indications, Conditions and Syndromes.

Peptides, compositions and methods of the present invention are directed towards the treatment of fibrotic and sclerotic diseases, indications, conditions and syndromes in a subject. There are a number of fibrotic and sclerotic diseases, indications, conditions and syndromes which may be so treated. Fibrotic and sclerotic diseases, indications, conditions and syndromes frequently include an inflammatory component, and thus many may similarly be categorized as an inflammatory disease or condition, and are listed in section 2.1 above. Fibrotic and sclerotic diseases and conditions, in addition to including an inflammatory component, may also be idiopathic, toxic, hereditary and/or pharmacologically-induced disorders. In general, fibrotic disorders are characterized by excessive production of extracellular matrix, primarily type I collagen, which may result in loss of organ function. It is believed, without wishing to be bound by theory, that agonism of MCR-1 can result in suppression of transforming growth factor-$\beta_1$-induced collagen synthesis by human dermal fibroblasts, thereby providing therapeutic and/or prophylactic benefit for fibrotic and sclerotic diseases, indications, conditions and syndromes. Representative fibrotic and sclerotic diseases and conditions that can be so treated include, but are not limited to, localized scleroderma, systemic sclerosis, sclerodermic graft-versus-host disease of the skin, idiopathic lung fibrosis, bleomycin-induced lung fibrosis, cyclosporine-induced nephropathy, cirrhosis of the liver, hypertrophic scars, keloids and the like.

2.3 Diseases Related to Increased Cytokine Expression and Related Diseases, Indications, Conditions and Syndromes.

Expression of various cytokines is increased during an inflammatory process, including an inflammatory process secondary to circulatory shock, ischemia, reperfusion injury and the like. TNF-$\alpha$ is a pleiotropic cytokine produced mainly by macrophages, and also by other types of cells. Other cytokines which increase during an inflammatory process, including an inflammatory process secondary to circulatory shock, ischemia, reperfusion injury and the like, include IL-1 and IL-6. While cytokines such as TNF-$\alpha$ have beneficial effects in many instances, significantly increased levels, such as secondary to circulatory shock, ischemia, reperfusion injury and the like, can have pathological effects. In one aspect, reperfusion of hypoxic or ischemic tissues, such as secondary to circulatory shock, results in inflammatory responses, including increased cytokine expression.

In one embodiment, the invention is directed to methods of using one or more of the peptides of the present invention to decrease pro-inflammatory cytokine production and expression, including decreasing pro-inflammatory cytokine production and expression secondary to circulatory shock, ischemia, reperfusion injury and the like. The decrease in pro-inflammatory cytokine production and expression, including without limitation one or more of TNF-$\alpha$, IL-1 and IL-6, occurs instantaneously or within a short time period following administration of a composition comprising one or more of the peptides of the present invention, preferably within at least about 40 minutes following administration, more preferably within 1-20 minutes, more preferably within 1-15 minutes, and most preferably within about 1-10 minutes.

In a related embodiment, the invention is directed to methods of using one or more of the peptides of the present invention to increase anti-inflammatory cytokine production and expression. The increase in anti-inflammatory cytokine production and expression, including without limitation IL-10, occurs instantaneously or within a short time period following administration of a composition comprising one or more of the peptides of the present invention, preferably within at least about 40 minutes following administration, more preferably within 1-20 minutes, more preferably within 1-15 minutes, and most preferably within about 1-10 minutes.

2.4 Dermatologic Diseases, Indications, Conditions and Syndromes.

Peptides, compositions and methods of the present invention are further directed towards the treatment of dermatologic and cosmetic diseases, indications, conditions and syndromes. In one aspect, peptides and compositions of the present invention are MCR-1 agonists which stimulate melanocytes and related cells to increase the level of melanin in the skin. By increasing the level of melanin in the skin, protection against ultraviolet radiation (UVR) and sunlight is afforded, including protection against phototoxicity and photosensitivity of the skin caused by UVR, sun and light.

In one aspect, peptides, compositions and methods of the present invention may be utilized for prophylactic and/or therapeutic treatment of dermal diseases, indications, conditions and syndromes such as acne vulgaris (commonly referred to as acne), atopic dermatitis (commonly referred to as atopic eczema or eczema), polymorphous light eruption, psoriasis, rosacea, seborrheic dermatitis, vitiligo, porphyria, porphyria cutanea tarda, erythropoietic protoporphyria, solar urticaria, urticaria pigmentosa or xeroderma pigmentosum. In another aspect, peptides, compositions and methods of the present invention may be utilized to prevent, limit or treat photosensitive or photoresponsive viral infections, such as herpes simplex virus (commonly referred to as cold sores and genital herpes depending on the site of infection), human papilloma virus and varicella zoster virus. In another aspect, peptides, compositions and methods of the present invention may be utilized to prevent, limit or treat cancers of the skin, including use in pre-cancerous conditions, and including use in actinic keratosis, basal cell carcinoma, melanoma or squamous cell carcinoma. In another aspect, peptides, compositions and methods of the present invention may be utilized to prevent or limit adverse effects of various therapies, including phototherapies, such as photodynamic therapy. In yet another aspect, peptides, compositions and methods of the present invention may be utilized to induce a tan, to decrease hair graying or for similar and related purposes relating to increased melanin production.

Peptides of the present invention may be administered by any of a variety of means, including application directly to the skin such as by means of oils, ointments, creams, gels, salves and the like, or by systemic administration, including by means of implants, such as subcutaneous dissolving implants.

2.5 Cytokine and/or Growth Factor Responsive Cancers.

Certain cancers, such as mesothelioma, are reported to be very sensitive to growth-promoting influences of cytokines and growth factors, and may be treatable by means of peptides selective for MCR-1. Canania, A., et al., "Autocrine inhibitory influences of α-melanocyte-stimulating hormone in malignant pleural mesothelioma," *J. Leukoc. Biol.* 75:253-259 (2004). Cancers that may be so treated include pleural mesothelioma, known to express mRHA for MCR-1 and the receptor protein, as well as other tumors that express MCR-1, including but not limited to adenocarcinoma, such as pulmonary adenocarcinoma.

2.6 Ocular Disease, Indications, Conditions and Syndromes.

There are a number of ocular diseases, indications, conditions and syndromes characterized by inflammation, including but not limited to increased cytokine production. One example is dry eye disease, an ocular disease affecting approximately 10-20% of the population. This disease progressively affects larger percentages of the population as it ages, with the majority of these patients being women. In addition, almost everyone experiences ocular irritation, or the symptoms and/or signs of dry eye as a condition, from time to time under certain circumstances, such as prolonged visual tasking (e.g., working on a computer), being in a dry environment, using medications that result in ocular drying and so on. In individuals suffering from dry eye, the protective layer of tears that normally protects the ocular surface is compromised, a result of insufficient or unhealthy production of one or more tear components. This can lead to exposure of the surface of the eye, ultimately promoting desiccation and damage of surface cells. Signs and symptoms of dry eye include but are not limited to keratitis, conjunctival and corneal staining, redness, blurry vision, decreased tear film break-up time, decreased tear production, tear volume, and tear flow, increased conjunctival redness, excess debris in the tear film, ocular dryness, ocular grittiness, ocular burning, foreign body sensation in the eye, excess tearing, photophobia, ocular stinging, refractive impairment, ocular sensitivity, and ocular irritation. Patients may experience one or more of these symptoms. The excess tearing response may seem counterintuitive, but it is a natural reflex response to the irritation and foreign body sensation caused by the dry eye. Some patients may also experience ocular itching due to a combination of ocular allergy and dry eye symptoms.

There are many possible variables that can influence a patient's signs or symptoms of dry eye including levels of circulating hormones, various autoimmune diseases (e.g., Sjögren's syndrome and systemic lupus erythematosus), ocular surgeries including PRK or LASIK, many medications, environmental conditions, visual tasking such as computer use, ocular fatigue, contact lens wear, and mechanical influences such as corneal sensitivity, partial lid closure, surface irregularities (e.g., pterygium), and lid irregularities (e.g., ptosis, entropion/ectropion, pinguecula). Environments with low humidity, such as those that cause dehydration, can exacerbate or cause dry eye symptoms, such as sitting in a car with the defroster on or living in a dry climate zone. In addition, visual tasking can exacerbate symptoms. Tasks that can greatly influence symptoms include watching TV or using a computer for long periods of time where the blink rate is decreased.

Uveitis is an ocular disease involving inflammation of the middle layer or uvea of the eye, and may also be understood to include any inflammatory process involving the interior of the eye. Uveitis includes anterior, intermediate, posterior and panuveitic forms, with the majority of uveitis cases anterior in location, involving inflammation of the iris and anterior chamber. This condition can occur as a single episode and subside with proper treatment or may take on a recurrent or chronic nature. Symptoms include red eye, injected conjunctiva, pain and decreased vision. Signs include dilated ciliary vessels, presence of cells and flare in the anterior chamber, and keratic precipitates on the posterior surface of the cornea. Intermediate uveitis includes inflammation and the presence of inflammatory cells in the vitreous cavity, and posterior uveitis include the inflammation of the retina and choroid. Uveitis may be secondary to any of a number of diseases and disorders, including acute posterior multifocal placoid pigment epitheliopathy, ankylosing spondylitis, Behçet's disease, birdshot retinochoroidopathy, brucellosis, herpes simplex, herpes zoster, inflammatory bowel disease, juvenile rheumatoid arthritis, Kawasaki disease, leptospirosis, Lyme disease, multiple sclerosis, psoriatic arthritis, Reiter's syndrome, sarcoidosis, syphilis, systemic lupus erythematosus, toxocariasis, toxoplasmosis, tuberculosis, Vogt-Koyanagi-Harada syndrome, Whipple disease or polyarteritis nodosa.

In one embodiment, the invention is directed to methods of using one or more of the peptides of the present invention for treatment of any of the foregoing ocular diseases, indications, conditions and syndromes. Such treatment may include treatment by means of eye drops, ointments, gels, washes, implants, plugs or other means and methods for delivering one or more of the peptides of the present invention to an ocular surface.

2.7 Ischemia and Related Diseases, Indications, Conditions and Syndromes.

Ischemia refers to any decrease or stoppage in the blood supply to any bodily organ, tissue, cell, or part, particularly where that decrease or stoppage leads to or would likely lead to ischemic damage to the bodily organ, tissue, cell, or part. An "ischemic episode" refers to any transient or permanent period of ischemia. Ischemia may result from any constriction or obstruction of the vasculature, or may result from circulatory shock, such as hemorrhagic shock, hypovolemic shock, or the like. The decrease or lack of blood flow results in a decrease or lack of oxygen to the affected part of the body, and may also result in an increase of inflammatory disease mediator chemicals such as various cytokines and other substances. During certain surgical procedures such as cardiac surgery and organ transplantation, the flow of blood is stopped temporarily and then resumed (reperfusion), resulting in ischemia-reperfusion injury. During a heart attack, the blood that supplies the heart is stopped, also resulting in ischemia that can evolve into infarction. Current treatment to relieve heart attacks requires reperfusion of the ischemic area of the heart, such as by using thrombolytic drugs or coronary angioplasty.

The invention has particular application in prevention of injury due to renal ischemia, including lung injury secondary to renal ischemia, preventing or limiting ischemic heart injuries subsequent to a myocardial infarction, preventing or limiting ischemic brain injuries subsequent to a cardiovascular injury, including without limitation myocardial infarction, stroke or the like. Neuroprotection is provided by administration of a composition of the invention to a patient with cerebral ischemia or stroke, particularly patients who are concurrently hypotensive. The invention has further particular application in preventing or limiting ischemic organ damage in organ transplant, including transplant of the heart, kidney, liver, lungs, pancreas or small intestine. In one aspect, the pharmaceutical composition of the present invention may be utilized for perfusion of a transplant organ, which perfusion may be prior to, during or subsequent to transplant of the organ.

In one embodiment, the invention is directed to methods of using one or more of the peptides of the present invention to protect the heart, brain or other organs of a patient against injury caused by ischemia. The protective effect against ischemia occurs instantaneously or within a short time period following administration of a composition comprising one or more of the peptides of the present invention, preferably within at least about 40 minutes following administration, more preferably within 1-20 minutes, more preferably within 1-15 minutes, and most preferably within about 1-10 minutes.

Ischemia may also results from any of a variety of diseases or conditions, and in one embodiment the invention is directed to methods of using one or more of the peptides of the present invention to protect the organs of a patient against injury resulting from ischemia, which ischemia is caused by a disease or condition. Such disease or condition may include, by way of example and not limitation, atherosclerotic diseases such as atheromata with thrombosis, embolism from the heart or from blood vessel from any organ, vasospasm, hypotension due to heart disease, hypotension due to systemic disease including infection or allergic reactions, or hypotension resulting from administration, ingestion or other exposure to one or more toxic compounds or drugs. Ischemia may also be secondary ischemia, and in another embodiment the invention is directed to methods of using one or more of the peptides of the present invention to protect the organs of a patient against injury resulting from secondary ischemia. Such secondary ischemia may be secondary to a disease or condition such diabetes mellitus, hyperlipidemia, hyperlipoproteinemia, dyslipidemia Buerger's disease, also called thromboangiitis obliterans, Takayasu's arteritis, arteritis temporalis, Kawasaki disease, also called lymph node syndrome, mucocutaneous node disease, infantile polyarteritis, cardiovascular syphilis, and various connective tissue diseases and disorders.

2.8 Ischemia-Reperfusion Injury and Related Diseases, Indications, Conditions and Syndromes.

Ischemia-reperfusion is the interruption of blood flow to bodily tissue and the subsequent and often abrupt restoration of blood flow to the tissue. While restoration of blood flow following ischemia is essential to preserve functional tissue, the reperfusion itself is known to be harmful to the tissue. Both ischemia and reperfusion are known to be important contributors to tissue necrosis. Several mechanisms appear to play a causative role in the generation of tissue damage associated with ischemia-reperfusion injury.

Various methods of limiting reperfusion injury have been described, such as induced hypothermia, controlled reperfusion, and ischemic preconditioning. Induced hypothermia is the induction of moderate hypothermia, thought to suppress many of the chemical reactions associated with reperfusion injury. Controlled reperfusion refers to controlling the initial period of reperfusion by reperfusing the tissue at a low pressure using blood that has been modified to be hyperosmolar, alkalotic, and substrate-enriched. Ischemic preconditioning is the purposeful causing of short ischemic events to have protective effect by slowing cell metabolism during a longer ischemic event. Although these treatments may be useful in surgical settings (e.g., before or after planned heart surgery), they are not possible in emergency settings.

The invention has particular application in preventing or limiting the severity of renal reperfusion injury, including lung injury secondary to renal reperfusion, preventing or limiting reperfusion heart injuries subsequent to a myocardial infarction, preventing or limiting reperfusion brain injuries subsequent to a cardiovascular injury, including without limitation myocardial infarction, stroke or the like. The invention has further particular application in preventing or limiting reperfusion organ damage in organ transplant, including transplant of the heart, kidney, liver, lungs, pancreas or small intestine. In one aspect, the pharmaceutical composition of the present invention may be utilized for perfusion of a transplant organ, which perfusion may be prior to, during or subsequent to transplant of the organ.

In one embodiment, the invention is directed to methods of using one or more of the peptides of the present invention to protect the heart, brain or other organs of a patient against injury caused by ischemia-reperfusion injury, including injury caused by or during reperfusion. The protective effect against ischemia-reperfusion injury occurs instantaneously or within a short time period following administration of a composition comprising one or more of the peptides of the present invention, preferably within at least about 40 minutes following administration, more preferably within 1-20 minutes, more preferably within 1-15 minutes, and most preferably within about 1-10 minutes.

2.9 Circulatory Shock and Related Diseases, Indications, Conditions and Syndromes.

Peptides, compositions and methods of the present invention may be employed for the treatment of circulatory shock in a subject. The compositions and methods provided herein may be employed to treat Stage I shock, Stage II shock or Stage III shock. In one particular embodiment, the methods of the present invention are used to treat the initial stage of shock, which initial stage of shock is characterized by cardiac output insufficient to meet the body's metabolic needs, but not otherwise low enough to produce significant symptoms. The patient may be anxious and alert, with increased respiration.

By "Stage I shock," also sometimes called "compensated shock" or "non-progressive shock," is meant a condition which occurs when the body detects decreased blood flow or perfusion and begins to activate one or more of several reactive mechanisms to restore perfusion or direct blood flow to the most vital body organs. Stage I shock can be asymptomatic, but may also include, but is not limited to, symptoms such as low blood flow or perfusion, rapid or increased heart rate, shallow or irregular breathing, hypotension, hypertension, pallor and cyanosis.

By "Stage II shock," also sometimes called "decompensated shock" or "progressive shock," is mean a condition which occurs when the compensatory mechanisms of the body begin to fail and organ perfusion cannot be restored to normal or maintained. Symptoms of Stage II shock include, but are not limited to, confusion, anxiety, disorientation and other mental disturbances indicating a lack of oxygen to the brain, chest pains, increased heart rate, oliguria, multiple organ dysfunction, falling blood pressure (hypotension), rapid breathing, weakness and pupil dilation.

By "Stage III shock," also sometimes called "irreversible shock," is meant a condition which occurs after the state of decreased perfusion or blood flow has existed to such an extent that the organs and tissues of the body are permanently affected. Such symptoms include, but are not limited to, multiple organ failure, kidney failure, coma, blood pooling in the extremities and death.

The invention provides compositions for use and methods of treating or preventing hemorrhagic shock in a patient, which include administering a composition including one or more of the peptides of the present invention to a patient diagnosed as suffering from blood loss. The blood loss may, but need not, be measured as a percentage of the subject's blood volume, such as, for example, a blood loss of greater than about 15% total blood volume, or greater than 20%, 25%, 30%, 35%, 40%, or 50% of the subject's total volume. Alternatively, the blood loss may, but need not, be measured in terms of a drop in blood volume in any amount sufficient to cause hemorrhagic shock in a particular subject, such as, for example, a loss of about 750 mL, 1000 mL, of about 1500 mL, or of about 2000 mL or more in a human subject. The blood loss may also be measured in terms of a drop in systolic blood pressure, such as, for example, a drop in systolic blood pressure that is about 20 mm Hg, 30 mm Hg, 40 mm Hg, 50 mm Hg, 60 mm Hg, 70 mm Hg, 80 mm Hg, 90 mm Hg or 100 mm Hg or more than 100 mm Hg lower than the subject's normal systolic blood pressure. In particular embodiments, the subject is undergoing or has undergone a medical procedure, such as, but not limited to, surgery, a transfusion or child birth. In other particular embodiments, the subject has suffered a traumatic injury, such as, but not limited to, resulting from a motor vehicle accident, from an industrial injury, or from a gunshot wound.

In additional embodiments of the present invention, the compositions and methods are used to treat cardiogenic shock, hypovolemic shock and vasodilatory shock, each of which can be in any of the aforementioned stages of shock. In one particular embodiment of the present invention, the methods are used to treat cardiogenic shock. Cardiogenic shock is, generally speaking, low blood flow or perfusion that is caused by heart malfunction where the heart does not pump adequate blood. Causes can include any condition that interferes with ventricular filling or emptying, such as, but not limited to, embolism, ischemia, regurgitation and valve malfunction. In another particular embodiment of the present invention, the methods are used to treat vasodilatory shock. Vasodilatory shock is caused by severe venous or arteriolar dilation, which results in inadequate blood flow. Several known causes contribute to vasodilatory shock including, but not limited to, cerebral trauma, drug or poison toxicity, anaphylaxis, liver failure, bacteremia and sepsis. In another more particular embodiment of the present invention, the methods are used to treat shock resulting from sepsis or bacteremia. In an even more particular embodiment, the compositions and methods are used to treat septic shock or bacteremic shock in Stage I, II or III. In yet another embodiment, the compositions and methods of the present invention are used to treat hypovolemic shock. Hypovolemic shock is, generally speaking, decreased intravascular volume, which decrease in intravascular volume can be relative or absolute. Hemorrhage from conditions such as, but not limited to, ulcers, gastrointestinal injury, trauma, accidents, surgery, and aneurysm may cause hypovolemic shock; but loss of other body fluids may also cause hypovolemic shock. For instance, renal fluid loss, intravascular fluid loss, water or other peritoneal fluid loss may contribute to hypovolemic shock. In one particular embodiment of the present invention, the compositions and methods, including administration of one or more of the peptides of the present invention, are used to treat hypovolemic shock. In an even more particular embodiment, the compositions and methods are used to treat hypovolemic shock in Stage I, Stage II or Stage III.

Circulatory shock, including hemorrhagic shock, may also result from partially controlled or uncontrolled bleeding within one or more internal organs or vessels of a patient. Bleeding may result from any cause, including by way of example from a ruptured aneurysm, dissected aorta, an ulcer, trauma or other gastrointestinal bleeding. In some instances the patient exhibits signs of circulatory shock or hypovolemia, which may include hypotension, but the source of internal bleeding is unknown.

In one embodiment, the invention is directed to methods of using one or more of the peptides of the present invention to protect the heart, brain or other organs of a patient against injury caused by circulatory shock. The protective effect against circulatory shock occurs instantaneously or within a short time period following administration of a composition comprising one or more of the peptides of the present invention, preferably within at least about 40 minutes following administration, more preferably within 1-20 minutes, more preferably within 1-15 minutes, and most preferably within about 1-10 minutes.

2.10 Targeted Imaging and Cytotoxic Therapy for Melanoma and Other Indications.

Peptides, compositions and methods of the present invention may be employed for imaging melanoma and other cancers or diseases or conditions characterized, in part, by relatively high expression of MCR-1, such as by diagnostic imaging using a radionuclide in combination with a peptide of the present invention. For diagnostic imaging, typically a peptide of the present invention is conjugated to radionuclide by use of a linker, such as a cross-linking agent that couples the peptide of the present invention to a radionuclide. The radionuclide is preferably a gamma emitter that may be imaged using a gamma detector or camera, such as single photon emission computed tomography, or is a positron emitter that may be imaged using positron emission tomography. Gamma emitters that may be so employed include $^{99m}$Tc, $^{111}$In, $^{123}$I and $^{67}$Ga, among others. Positron emitters that may be so employed include $^{11}$C, $^{13}$N, $^{15}$O and $^{18}$F.

In a related aspect, peptides, compositions and methods of the present invention may be employed for cytotoxic therapy of melanoma, other cancers or diseases or conditions characterized, in part, by relatively high expression of MCR-1, such as by utilizing a chemotherapeutic agent, including toxins, or radiation therapeutic agent, in combination with a peptide of the present invention. Chemotherapeutic agents include any antineoplastic drug or chemical, such as for example alkylating agents, antimetabolites, anthracyclines, plant alkaloids, topoisomerase inhibitors, and other antitumor agents. Non-limiting examples of alkylating agents include cisplatin, carboplatin, oxaliplatin, mechlorethamine, cyclophosphamide, chlorambucil and ifosfamide; examples of antimetabolites include azathioprine and mercaptopurine; examples of anthracyclines include daunorubicin, doxorubicin, epirubicin, idarubicin, valrubicin and mitoxantrone; examples of plant alkaloids include vinca alkaloids such as vincristine, vinblastine, vinorelbine and vindesine and taxanes such as paclitaxel and docetaxel; examples of topoisomerase inhibitors include camptothecins such as irinotecan and topotecan and type II topoisomerases such as amsacrine, etoposide, etoposide phosphate and teniposide. However, any agent suitable for use in targeted cytotoxic therapy may be so employed. Non-limiting examples of radiation therapeutic agents that may be so employed include $^{131}$I, $^{125}$I, $^{211}$At, $^{186}$Re, $^{188}$Re, $^{90}$Y, $^{153}$Sm, $^{212}$Bi and $^{32}$P, among others.

Diagnostic imaging or cytotoxic therapy agents may be incorporated into a peptide of the present invention, for example such as by use of $^{11}$C, $^{13}$N, $^{15}$O, among others, in place of nonradioactive isotopes; may be linked directly to a peptide of the present invention, such as for example by halogenation or other direct complexation methods; or may be linked indirectly to a peptide of the present invention, such as conjugation by means of a linker or chelation unit. Linker units are well known in the art, and include, but are not limited to, chemically-linked conjugates including at least one disulfide bond, thioether bond or covalent bond between free reactive groups. Representative cross-linking and conjugating reagents are disclosed in U.S. Pat. Nos. 7,169,603, 7,820,164 and 5,443,816 and US Publication No. 2009/0297444, among others, incorporated herein by reference.

3.0 Combination Therapy for Certain Indications

The peptides, compositions and methods of the present invention may be used for treatment of any of the foregoing diseases, indications, conditions or syndromes, or any disease, indication, condition or syndrome which is MCR-1 mediated or responsive, by administration in combination with one or more other pharmaceutically active compounds. Such combination administration may be by means of a single dosage form which includes both a peptide of the present invention and one more other pharmaceutically active compounds, such single dosage form including a tablet, capsule, spray, inhalation powder, injectable liquid or the like. Alternatively, combination administration may be by means of administration of two different dosage forms, with one dosage form containing a peptide of the present invention, and the other dosage form including another pharmaceutically active compound. In this instance, the dosage forms may be the same or different. The term "coadminister" indicates that each of at least two compounds in the combination therapy are administered during a time frame wherein the respective periods of biological activity or effects overlap. Thus the term includes sequential as well as concurrent administration of compounds where one compound is one or more of the peptides of the present invention. If more than one compound is coadministered, the routes of administration of the two or more compounds need not be the same. Without meaning to limit combination therapies, the following exemplifies certain combination therapies which may be employed.

3.1 Combination Therapy with Anti-Inflammatory Agents.

For the treatment of inflammation-related diseases, indications, conditions and syndromes, peptides of the present invention may be used in combination therapy, including by means of coadministration, with one or more anti-inflammatory agents. One class of anti-inflammatory agent is glucocorticoids, including but not limited to cortisone, including cortisone acetate, hydrocortisone, prednisone, prednisolone, methylprednisolone, dexamethasone, betamethasone, triamcinolone, beclometasone, prednisone, fludrocortisone acetate, deoxycorticosterone acetate and aldosterone. Other anti-inflammatory agents that may be used in combination therapy, including by means of coadministration, include aspirin, non-steroidal anti-inflammatory drugs (NSAIDs) (such as ibuprofen), TNF-α inhibitors (such as tenidap and rapamycin or derivatives thereof), or TNF-α antagonists (e.g., infliximab, OR1384), cyclooxygenase inhibitors (i.e., COX-1 and/or COX-2 inhibitors such as NAPROXEN® or CELEBREX®), CTLA4-Ig agonists/antagonists, CD40 ligand antagonists, IMPDH inhibitors, such as mycophenolate (CELLCEP®), integrin antagonists, alpha-4 beta-7 integrin antagonists, cell adhesion inhibitors, interferon gamma antagonists, ICAM-1, prostaglandin synthesis inhibitors, budesonide, clofazimine, p38 mitogen-activated protein kinase inhibitors, protein tyrosine kinase (PTK) inhibitors, IKK inhibitors, therapies for the treatment of irritable bowel syndrome (e.g., ZELMAC® and MAXI-K® openers such as those disclosed in U.S. Pat. No. 6,184,231), or other NF-κB inhibitors, such as corticosteroids, calphostin, CSAIDs, 4-substituted imidazo [1,2-A] quinoxalines as disclosed in U.S. Pat. No. 4,200,750; Interleukin-10, salicylates, nitric oxide, and other immunosuppressants; and nuclear translocation inhibitors, such as deoxyspergualin (DSG).

3.2 Combination Therapy with Phosphodiesterase Inhibitors.

For certain applications and indications, it is desirable to increase production of and maintain levels of cyclic adenoise 3',5' monophosphate (cAMP), a nucleotide messenger associated with inflammatory cell activity. Peptides of the present invention increase intracellular levels of cAMP, and can be coadministered with compounds or substances that inhibit the degradation of cAMP. cAMP is hydrolyzed to an inactive form by phosphodiesterase (PDE); compounds or substances that inhibit PDE may thereby result in maintenance of and/or an increase in available cAMP. A class of compounds known as PDE inhibitors has been extensively studied for use in treatment of inflammatory diseases, such as asthma, COPD and acute respiratory distress syndrome. Preferred are inhibitors of PDE type 1, 2, 3, 4, 7, 8, 10 or 11; in one aspect this includes cAMP-PDE inhibitors that are selective PDE type 4 inhibitors or inhibitors having selectivity for one particular type of PDE 4 isoenzyme, such as, by way of example, rolipram, cilomilast, ibudilast, and piclamilast. In general, the methods and compositions of this invention may comprise use of one or more cAMP-PDE inhibitors described in one or more of the following U.S. patents or patent applications, each of which is incorporated herein by reference: U.S. Pat. Appl. No. 20090221664, "Pharmaceutical Compositions of Muscarinic Receptor Antagonists"; U.S. Pat. Appl. No. 20090054382, "Compositions of Phosphodiesterase Type IV Inhibitors"; U.S. Pat. Appl. No. 20090017036, "Pharmaceutical Compositions for Treatment of Respiratory and Gastrointestinal Disorders"; U.S. Pat. Appl. No. 20080292562, "Medicaments for Inhalation Comprising PDE IV Inhibitors and Enantiomerically Pure Glycopyrrolate Salts"; U.S. Pat. Appl. No. 20080085858, "Pharmaceutical Composition"; U.S. Pat. Appl. No. 20080045718, "Process and intermediates for the synthesis of 2-(quinolin-5-yl)-4,5 disubstituted-azole derivatives"; U.S. Pat. Appl. No. 20070287689, "Therapeutic and/or Preventive Agents for Chronic Skin Diseases"; U.S. Pat. Appl. No. 20060239927, "Drug for airway administration"; U.S. Pat. No. 7,544,675, "Chemical compounds with dual activity, processes for their preparation and pharmaceutical compositions"; U.S. Pat. No. 7,459,451, "Pyrazolopyridine derivatives"; U.S. Pat. No. 7,317,009, "Pyrrolopyridazine derivatives"; U.S. Pat. No. 7,312,328, "Benzoylpyridazines"; U.S. Pat. No. 7,153,854, "Pyrrolopyridazine derivatives"; U.S. Pat. No. 7,115,623, "PDE IV inhibitors"; U.S. Pat. No. 6,924,292, "Furoisoquinoline derivatives, process for producing the same and use thereof"; U.S. Pat. No. 6,872,382, "Use of selective PDE IV inhibitors to treat dry eye disorders"; U.S. Pat. No. 6,765,095, "2,3-disubstituted pyridine derivative, process for the preparation thereof, pharmaceutical composition containing the same, and intermediate therefor"; U.S. Pat. No. 6,740,662, "Naphthyridine derivatives"; U.S. Pat. No. 6,683,186, "2,3-Disubstituted pyridine derivative, process for the preparation thereof, pharmaceutical composition containing the same, and intermediate therefor"; U.S. Pat. No. 6,656,959, "PDE IV inhibiting pyridine derivatives"; U.S. Pat. No. 6,642,250, "1,8-naphthyridin-2(1H)-one derivatives"; U.S. Pat. No. 6,555,557, "2,3-disubstituted pyridine derivatives, process for the preparation thereof, drug compositions containing the same and intermediates for the preparation"; U.S. Pat. No. 6,440,979, "Aryl isoguanines"; U.S. Pat. No. 6,436,965, "PDE IV inhibiting amides, compositions and methods of treatment"; U.S. Pat. No. 6,417,190, "Tricyclic nitrogen heterocycles as PDE IV inhibitors"; U.S. Pat. No. 6,413,975, "Purine derivatives having phosphodiesterase IV inhibition activity"; U.S. Pat. No. 6,403,805, "1,3-dihydro-1-(phenylalkyl)-2H-imidazol-2-one derivatives"; U.S. Pat. No. 6,372,770, "Benzoxazoles"; U.S. Pat. No. 6,365,606, "6,5-fused aromatic ring systems having enhanced phosphodiesterase IV inhibitory activity"; U.S. Pat. No. 6,310,205, "Hypoxathine compounds"; U.S. Pat. No. 6,306,583, "Human brain phosphodiesterase"; U.S. Pat. No. 6,268,373, "Trisubstituted thioxanthines"; U.S. Pat. No. 6,248,769, "Phenyltriazole compounds for PDE-IV inhibition"; U.S. Pat. No. 6,248,768, "Benzimidazole derivatives and pharmacologically acceptable salts thereof"; U.S. Pat. No. 6,248,746, "3-(arylalkyl) xanthines"; U.S. Pat. Nos. 6,211,222 and 6,127,398, "Substituted indazole derivatives and related compounds"; U.S. Pat. No. 6,211,203, "Benzofuran-4-carboxamides"; U.S. Pat. No. 6,200,993, "Heterosubstituted pyridine derivatives as PDE4 inhibitors"; U.S. Pat. No. 6,191,138, "Phenanthridines"; U.S. Pat. No. 6,180,650, "Heterosubstituted pyridine derivatives as PDE4 inhibitors"; U.S. Pat. No. 6,136,821, "Naphthyridine derivatives"; U.S. Pat. No. 6,054,475, "Substituted dihydrobenzofuran-based phosphodiesterase 4 Inhibitors useful for treating airway disorders"; U.S. Pat. No. 6,043,263, "(2,3-dihydrobenzofuranyl)-thiazoles as phosphodiesterase inhibitors"; U.S. Pat. No. 6,011,037, "Thiazole derivatives with phosphodiesterase-inhibiting action"; U.S. Pat. No. 5,972,927, "Diazepinoindoles as phosphodiesterase 4 inhibitors"; U.S. Pat. No. 5,919,801, "N-substituted piperidines as PDE4 inhibitors"; U.S. Pat. No. 6,204,275, "PDE IV Inhibiting compounds, compositions and methods of treatment"; U.S. Pat. No. 6,143,782, "Anti-inflammatory and anti-asthma treatment with reduced side effects"; U.S. Pat. No. 6,103,749, "Aryl imidazole compounds having phosphodiesterase IV activity"; U.S. Pat. No. 6,096,768, "Compounds containing phenyl linked to aryl or heteroaryl by an aliphatic or heteroatom containing linking group"; U.S. Pat. No. 6,075,016, "6,5-fused aromatic ring systems having enhanced phosphodiesterase IV inhibitory activity"; U.S. Pat. No. 6,040,447, "Purine compounds having PDE IV inhibitory activity and methods of synthesis"; U.S. Pat. No. 6,034,089, "Aryl thiophene derivatives as PDE IV inhibitors"; U.S. Pat. No. 6,020,339, "Aryl furan derivatives as PDE IV inhibitors"; U.S. Pat. No. 5,935,978, "Compounds containing phenyl linked to aryl or heteroaryl by an aliphatic or heteroatom containing linking group"; U.S. Pat. No. 5,935,977, "Substituted vinyl pyridine derivative and drugs containing same"; U.S. Pat. No. 5,840,724, "Compounds containing phenyl linked to aryl or heteroaryl by an aliphatic or heteroatom containing linking group"; U.S. Pat. No. 5,710,170, "Tri-aryl ethane derivatives as PDE IV inhibitors"; U.S. Pat. No. 5,710,160, "Diphenyl pyridyl ethane derivatives as PDE IV inhibitors"; U.S. Pat. No. 5,698,711, "Compounds containing phenyl linked to aryl or heteroaryl by an aliphatic or heteroatom containing linking group"; U.S. Pat. No. 5,691,376, "Substituted biphenyl derivatives"; U.S. Pat. No. 5,679,696, "Compounds containing phenyl linked to aryl or heteroaryl by an aliphatic or heteroatom containing linking group"; U.S. Pat. No. 5,665,737, "Substituted benzoxazoles"; U.S. Pat. No. 5,650,444, "Substituted biphenyl derivatives"; U.S. Pat. No. 5,616,614, "Naphthylalkylamines"; U.S. Pat. No. 5,541,219, "1-Alkoxy-2-(alkoxy or cycloalkoxy)-4-(cyclothio-alkyl or cyclothioalkenyl)benzenes as inhibitors of cyclic AMP phosphodiesterase and tumor necrosis factor"; U.S. Pat. No. 5,502,072, "Substituted oxindoles"; U.S. Pat. No. 5,466,697, "8-phenyl-1,6-naphthyri-dine-5-ones"; U.S. Pat. No. 5,459,151, "N-acyl substituted phenyl piperidines as bronchodilators and anti-inflammatory agents"; U.S. Pat. No. 5,393,788, "Phenylalkyl oxamides"; U.S. Pat. No. 5,356,923, "1-hydroxy-4(3-cyclopentyloxy-4-methoxphenyl)-2-pyrrolidone and antihypertensive use thereof"; U.S. Pat. No. 5,250,700, "Phenyl pyrazolidinones as bronchodilators and anti-inflammatory agents"; U.S. Pat. No. 5,191,084, "Phenyl pyrazolidinones as bronchodilators and anti-inflammatory agents"; U.S. Pat.

No. 5,124,455, "Oxime carbamates and oxime carbonates as bronchodilators and anti-inflammatory agents"; U.S. Pat. No. 6,180,791, "Synthesis of 8-substituted xanthines"; U.S. Pat. No. 6,057,369, "Substituted (aryl, heteroaryl, arylmethyl or heteroarylmethyl)hydroxamic acid compounds"; U.S. Pat. No. 5,541,219, "1-Alkoxy-2-(alkoxy or cycloalkoxy)-4-(cyclothioalkyl or cyclothioalkenyl)benzenes as inhibitors of cyclic AMP phosphodiesterase and tumor necrosis factor"; U.S. Pat. No. 5,362,915, "Phenyl substituted cycloalkenyl compounds useful as PDE IV inhibitors"; U.S. Pat. No. 6,040,329, "Substituted indazole analogs"; U.S. Pat. No. 5,958,953, "Substituted indazole derivatives"; U.S. Pat. No. 6,090,817, "Phenylpyridine derivatives useful as phosphodiesterase inhibitors"; U.S. Pat. No. 5,922,740, "Heterocyclylcarbonyl substituted benzofuranylureas"; U.S. Pat. No. 5,866,571, "9-substituted 2-2-n-alkoxyphenyl)-purin-6-ones-"; U.S. Pat. No. 5,861,404, "2,9-disubstituted purin-6-ones"; U.S. Pat. No. 5,861,396, "Purin-6-one derivatives"; U.S. Pat. No. 5,721,238, "2,8-disubstituted quinazolinones"; U.S. Pat. No. 5,723,463, "Pyrido 3,2-Pyrazinones with Anti-asthmatic action and Processes for their Manufacture"; and U.S. Pat. No. 5,596,013, "Dihydro pyrazolopyrroles."

3.3 Combination Therapy in Ocular Indications.

For ocular indications, an ophthalmic dosage form may include one or more active ingredients in addition to one or more of the peptides of the present invention, such as for example artificial tear components, topical corticosteroids, non-steroidal anti-inflammatory drugs, or calcineurin inhibitors such as cyclosporine-A (RESTASIS®-Allergan). It is also possible that coadministration includes administration of one or more additional compounds given separately from a peptide of the present invention, such as separate administration of an ophthalmic dosage form including an artificial tear component, a topical corticosteroid, a non-steroidal anti-inflammatory drugs, a calcineurin inhibitor such a cyclosporine-A, or a combination of any of the foregoing.

Combination ophthalmic solutions may be employed, including specifically solutions including more than one active pharmaceutical ingredient. In one aspect, a non-steroidal anti-inflammatory drug (NSAID) is employed in combination with a peptide of the present invention. NSAIDs suitable for use in combination ophthalmic solutions include agents, their esters and pharmaceutically acceptable salts thereof that inhibit the cycloxygenase (COX)-1 and/or -2 enzyme, including but not limited to propionic acid compounds such as naproxen, flurbiprofen, oxaprozin, ibuprofen, ketoprofen, fenoprofen; ketorolac tromethamine; acetic acid derivatives such as sulindac, indomethacin, and etodolac; phenylacetic acids such as diclofenac, bromfenac, and suprofen; arylacetic prodrugs such as nepafenac, and amfenac; salicyclic acids, such as aspirin, salsalate, diflunisal, choline magnesium trisalicylate; para-aminophenol derivatives such as acetaminophen; naphthylalkanones such as nabumetone; enolic acid derivatives such as piroxicam and meloxicam; femanates such as mefenamic acid, meclofenamate and flufenamic acid; pyrroleacetic acids such as tolmetin; and pyrazolones such as phenylbutazone; and COX-2 selective inhibitors such as celecoxib, valdecoxib, parecoxib, etoricoxib, and luaricoxib. The ophthalmic solutions may additionally comprise other active ingredients, including, but not limited to, vasoconstrictors, anti-allergenic agents, anti-infectives, steroids, anesthetics, anti-inflammatories, analgesics, dry eye treatment agents (e.g. secretagogues, mucomimetics, polymers, lipids, antioxidants), and the like, or be administered in conjunction (simultaneously or sequentially) with pharmaceutical compositions comprising other active ingredients, including, but not limited to, vasoconstrictors, anti-allergenic agents, anti-infectives, steroids, anesthetics, anti-inflammatories, analgesics, dry eye treatment agents (e.g. secretagogues, mucomimetics, polymers, lipids, antioxidants), and the like.

3.4 Combination Therapy in Shock-Related Indications.

The methods of treating or preventing circulatory shock of the present invention also relate to coadministering one or more substances to the subject in addition to one or more of the peptides of the present invention. For example, one or more of the peptides of the present invention may be coadministered with androstenetriol, androstenediol or derivatives thereof, various vasopressin agonists, or other pharmaceutically active substances, such as catecholamines or other $\alpha$ adrenergic agonists, $\alpha_2$ adrenergic agonists, $\beta$ adrenergic agonists or $\beta_2$ adrenergic agonists, including but not limited to epinephrine, norepinephrine, dopamine, isoproterenol, vasopressin and dobutamine. Alternatively, one or more of the peptides of the present invention may be coadministered with fluids or other substances that are capable of alleviating, attenuating, preventing or removing symptoms in a subject suffering from, exhibiting the symptoms of, or at risk of suffering from hypovolemic shock, vasodilatory shock or cardiogenic shock. Types of fluid that can be coadministered with one or more of the peptides of the present invention should be specific to the circumstances surrounding the particular subject that is suffering from, exhibiting the symptoms of, or at risk of suffering from shock. For example, fluids that may be coadministered with one or more of the peptides of the present invention include, but are not limited to, salt solutions—such as sodium chloride and sodium bicarbonate—as well as whole blood, synthetic blood substitutes, plasma, serum, serum albumin and colloid solutions. Colloid solutions include, but are not limited to, solutions containing hetastarch, albumin or plasma. In one particular embodiment of the present invention, fluids such as one or more of salt solutions, colloidal solutions, whole blood, synthetic blood substitutes, plasma or serum are coadministered with one or more of the peptides of the present invention in patients suffering from or exhibiting the symptoms of a hypovolemic shock, such as hemorrhagic shock.

Particular embodiments of the coadministration methods of the present invention include methods of performing a transfusion in a subject, with the transfusion methods comprising providing blood or synthetic blood substitutes that comprise one or more of the peptides of the present invention to a subject. The blood used in the transfusion methods can be whole blood, synthetic blood substitutes, or any fractionated portion of whole blood, such as plasma, serum, or red blood cells.

4.0 Methods of Administration and Use

The method of administration and use varies depending upon the characteristic of specific peptides of the present invention, the disease, indication, condition or syndrome to be treated, and other factors known to those in the art. In general, any method of administration and use known in the art or hereafter developed may be employed with the peptides of the present invention. Without limiting the foregoing, the following methods of administration and use have specific application.

4.1 Inhalation Use.

In one aspect, a composition including one or more peptides of the present invention is formulated for administration to the respiratory tract, such as in the form of an aerosol or solution for a nebulizer, or as a microfine powder for insufflation or inhalation (e.g., topically to the lung and/or airways), alone or in combination with one or more inert carriers or additional active pharmaceutical ingredients, and in the form of a solution, a suspension, an aerosol or a dry powder formulation. See generally, Cryan, S.-A., "Carrier-based strategies for targeting protein and peptide drugs to the lungs," *The AAPS Journal* 7:E20-41 (2005). In general, the peptides of the present invention may be used the devices, formulations, compositions and means described in one or more of the following U.S. patents or patent applications, each of which is incorporated herein by reference: U.S. Pat. Appl. No. 20090241949, "Dry powder inhalation system"; U.S. Pat. Appl. No. 20080066741, "Methods and systems of delivering medication via inhalation"; U.S. Pat. Appl. No. 20070298116, "Amorphous, spray-dried powders having a reduced moisture content and a high long term stability"; U.S. Pat. Appl. No. 20070140976, "Aqueous inhalation pharmaceutical composition"; U.S. Pat. Appl. No. 20060054166, "Inhalation nebulizer"; U.S. Pat. Appl. No. 20050211244, "Dry powder preparations"; U.S. Pat. Appl. No. 20050123509. "Modulating charge density to produce improvements in the characteristics of spray-dried proteins"; U.S. Pat. Appl. No. 20040241232, "Dry powder medicament formulations"; U.S. Pat. No. 7,582,284, "Particulate materials"; U.S. Pat. No. 7,481,212, "Increased dosage metered dose inhaler"; U.S. Pat. No. 7,387,794, "Preparation of powder agglomerate"; U.S. Pat. No. 7,258,873, "Preservation of bioactive materials by spray drying"; U.S. Pat. No. 7,186,401, "Dry powder for inhalation"; U.S. Pat. No. 7,143,764, "Inhalation device"; U.S. Pat. No. 7,022,311, "Powdery inhalational preparations and process for producing the same"; U.S. Pat. No. 6,962,151, "Inhalation nebulizer"; U.S. Pat. No. 6,907,880, "Inhalation device"; U.S. Pat. No. 6,881,398, "Therapeutic dry powder preparation"; U.S. Pat. No. 6,698,425, "Powder inhaler"; U.S. Pat. No. 6,655,380, "Inhalation device"; U.S. Pat. No. 6,645,466, "Dry powder for inhalation"; U.S. Pat. No. 6,632,456, "Compositions for inhalation"; U.S. Pat. No. 6,610,272, "Medicinal aerosol formulation"; U.S. Pat. No. 6,596,261, "Method of administering a medicinal aerosol formulation"; U.S. Pat. No. 6,585,957, "Medicinal aerosol formulation"; U.S. Pat. No. 6,582,729, "Powered pharmaceutical formulations having improved dispersibility"; U.S. Pat. No. 6,572,893, "Systems and processes for spray drying hydrophobic drugs with hydrophilic excipients"; U.S. Pat. No. 6,551,578, "Modulated release particles for aerosol delivery"; U.S. Pat. No. 6,520,179, "Inhalation device"; U.S. Pat. No. 6,518,239, "Dry powder compositions having improved dispersivity"; U.S. Pat. No. 6,503,481, "Compositions for aerosolization and inhalation"; U.S. Pat. No. 6,358,530, "Powdered pharmaceutical formulations having improved dispersibility"; U.S. Pat. No. 6,325,061, "Inhalation device"; U.S. Pat. No. 6,257,232, "Inhalation device"; U.S. Pat. No. 6,187,344, "Powdered pharmaceutical formulations having improved dispersibility"; U.S. Pat. No. 6,116,237, "Methods of dry powder inhalation"; U.S. Pat. No. 5,934,272, "Device and method of creating aerosolized mist of respiratory drug"; and, U.S. Pat. No. 5,558,085, "Intrapulmonary delivery of peptide drugs".

Thus the composition may be a dry powder composition for topical delivery to the lung by inhalation. Typically the composition would contain a powder mix for inhalation of a peptide of the present invention and a suitable powder base, diluent or carrier substance such as lactose, glucose, dextran, mannitol or another sugar or starch. The composition may be used in any of a variety of dry powder devices, such as a reservoir dry powder inhaler, a multi-dose dry powder inhaler, or a metered dose inhaler. The composition may include additional excipients, such as an alcohol, a surfactant, a lubricant, an anti-oxidant or a stabilizing agent. Suitable propellants include hydrocarbon, chlorofluorocarbon and hydrofluoroalkane propellants, or mixtures of any such propellants.

Inhalation solutions also can be formulated in a liquefied propellant for aerosol delivery, such as with a pressurized metered dose inhaler. In yet another formulation, solutions may be in the form of a nebulised aqueous suspension or solution, with or without a suitable pH or tonicity adjustment, either as a single dose or multidose device.

4.2 Subcutaneous Injection Use.

In one aspect, a composition including one or more peptides of the present invention is formulated for subcutaneous injection, and a subcutaneous injection is given one or more times each day, preferably prior to a meal, more preferably between about one and about three hours prior to a mean. In another aspect, the composition is formulated as an injectable sustained release formulation. In one embodiment, a peptide of the present invention is formulated with a polyethylene glycol, such as polyethylene glycol 3350, and optionally one or more additional excipients and preservatives, including but not limited to excipients such as salts, polysorbate 80, sodium hydroxide or hydrochloric acid to adjust pH, and the like. In another embodiment a peptide of the present invention is formulated with a poly(ortho ester), which may be an auto-catalyzed poly(ortho ester) with any of a variable percentage of lactic acid in the polymeric backbone, and optionally one or more additional excipients. In one embodiment poly (D,L-lactide-co-glycolide) polymer (PLGA polymer) is employed, preferably a PLGA polymer with a hydrophilic end group, such as PLGA RG502H from Boehringer Ingelheim, Inc. (Ingelheim, Germany). Such formulations may be made, for example, by combining a peptide of the present invention in a suitable solvent, such as methanol, with a solution of PLGA in methylene chloride, and adding thereto a continuous phase solution of polyvinyl alcohol under suitable mixing conditions in a reactor. In general, any of a number of injectable and biodegradable polymers, which are preferably also adhesive polymers, may be employed in a sustained release injectable formulation. The teachings of U.S. Pat. Nos. 4,938,763, 6,432,438, and 6,673,767, and the biodegradable polymers and methods of formulation disclosed therein, are incorporated here by reference. The formulation may be such that an injection is required on a weekly, monthly or other periodic basis, depending on the concentration and amount of peptide, the biodegradation rate of the polymer, and other factors known to those of skill in the art.

4.3 Methods of Administration and Use for Circulatory Shock and Related Diseases, Indications, Conditions and Syndromes.

In yet another aspect, the invention includes methods which optionally include monitoring the subject for symptoms of circulatory shock both before and after administration of a pharmaceutical composition including one or more of the peptides of the present invention. Thus a subject may be administered one or more of the peptides of the present invention by one of the methods of the invention after suffering an injury likely to induce circulatory shock but prior to the manifestation of overt symptoms of cardiovascular shock, including prior to manifestation of circulatory shock in Stage I, Stage II or Stage III.

When administration is for the purpose of treatment, one or more of the peptides of the present invention are provided at, or after the onset of, a symptom of shock. The therapeutic administration of one or more of the peptides of the present invention may further serve to attenuate any symptom, or prevent additional symptoms from arising. When administration is for the purposes of preventing shock ("prophylactic administration"), one or more of the peptides of the present invention are provided in advance of any visible or detectable symptom. The prophylactic administration of one or more of the peptides of the present invention serve to attenuate subsequently arising symptoms or prevent symptoms from arising altogether. The route of administration of one or more of the peptides of the present invention include, but are not limited to, topical, transdermal, intranasal, pulmonary, vaginal, rectal, oral, subcutaneous, intravenous, intraarterial, intramuscular, intraosseous, intraperitoneal, epidural and intrathecal.

4.4 Methods of Administration and Use for Prophylactic Therapy.

The invention also relates to methods of preventing undesired cytokine expression by administering a therapeutically effective amount of one or more of the peptides of the present invention to the subject, prior to or immediately at the onset of the first symptoms. As used herein, the term "prevent," as it relates to shock, indicates that a substance of the present invention is administered to a subject to prohibit one or more symptoms of shock from detectably appearing or to attenuate the effects of one or more symptoms of shock. The term "prevent" also encompasses prohibiting or limiting excessive or undesired cytokine expression, such as with a "cytokine storm". Thus a subject may be "pretreated," such as a subject in a surgical setting, by using the substances of the present invention to prevent undesired cytokine expression or shock from arising. The phrase "preventing the progression," as it relates to shock, is used to mean a procedure designed to prohibit the detectable appearance of one or more additional symptoms of shock in a patient already exhibiting one or more symptoms of shock, and is also used to mean prohibiting the already-present symptoms of shock from worsening in the subject. The symptoms of shock that are included in preventative methods of the present invention include, but are not limited to, such symptoms of shock as highlighted herein, such as tachycardia, shallow or erratic breathing and death. A subject that is at risk of shock may be recognized based upon the specific circumstances surrounding a subject. Similarly, a patient with a bacterial or viral infection and exhibiting a fever or low blood pressure may also be at risk of excessive cytokine expression, shock or an inflammatory disease or condition.

In additional embodiments of the present invention, the methods are used to prevent cardiogenic shock, hypovolemic shock and vasodilatory shock, each of which can be in any of the three aforementioned stages of shock. In one particular embodiment of the present invention, the methods are used to prevent cardiogenic shock. In another particular embodiment of the present invention, the methods are used to prevent vasodilatory shock. In another more particular embodiment of the present invention, the methods are used to prevent shock resulting from sepsis or bacteremia. In an even more particular embodiment, the methods are used to prevent septic shock or bacteremic shock in Stage I, II or III shock. In yet another embodiment, the methods of the present invention are used to prevent hypovolemic shock.

Similar to the methods of treating shock described herein, one embodiment of the methods of preventing shock of the present invention comprises coadministering another substance with one or more of the peptides of the present invention or a derivative thereof. The scope of the invention is not limited by the identity of the substance which may be coadministered with one or more of the peptides of the present invention to prevent shock. For example, one or more of the peptides of the present invention may be coadministered with androstenetriol, androstenediol or derivatives thereof, various vasopressin agonists, or other pharmaceutically active substances, such as catecholamines or other α adrenergic agonists, $\alpha_2$ adrenergic agonists, β adrenergic agonists or $\beta_2$ adrenergic agonists, including but not limited to epinephrine, norepinephrine, dopamine, isoproterenol, vasopressin and dobutamine, to prevent shock.

Alternatively, one or more of the peptides of the present invention may be coadministered with fluids or other substances that are capable of preventing or removing symptoms in a subject at risk of suffering from hypovolemic shock, vasodilatory shock or cardiogenic shock. The types of fluid that can be coadministered with one or more of the peptides of the present invention to prevent shock should be specific to the circumstances surrounding the particular subject that is at risk of suffering from shock. For example, fluids that may be coadministered with one or more of the peptides of the present invention include, but are not limited to, salt solutions—such as sodium chloride and sodium bicarbonate—as well as whole blood, synthetic blood substitutes, plasma, serum, serum albumin and colloid solutions. Colloid solutions include, but are not limited to, solutions containing hetastarch, albumin or plasma. In one particular embodiment of the present invention, fluids including one or more of salt solutions, colloidal solutions, whole blood, synthetic blood substitutes, plasma or serum are coadministered with one or more of the peptides of the present invention or a derivative thereof in subjects at risk of suffering a hypovolemic shock, such as hemorrhagic shock.

4.5 Methods of Administration and Use for Inflammation Related Applications, Diseases, Indications, Conditions and Syndromes.

In yet another aspect, the invention includes methods which optionally include monitoring the subject for signs or symptoms of inflammation, inflammatory diseases or inflammatory conditions both before and after administration of one or more of the peptides of the present invention. Thus a subject may be administered one or more of the peptides of the present invention by one of the methods of the invention after being diagnosed with a condition, disease or syndrome likely to induce an inflammatory response, but prior to the manifestation of overt symptoms of inflammation, inflammatory disease or inflammatory condition. Methods of treating or preventing inflammation, inflammatory diseases or inflammatory conditions described herein comprise administering a therapeutically effective amount of one or more of the peptides of the present invention to a subject. As used herein, the term "administer" and "administering" are used to mean introducing at least one compound into a subject. When administration is for the purpose of treatment, the substance is provided at, or after the onset of, a sign or symptom of inflammation, inflammatory disease or inflammatory condition. The therapeutic administration of this substance serves to attenuate any symptom, or prevent additional symptoms from arising. When administration is prophylactic administration for the purposes of preventing or limiting inflammation, inflammatory disease or an inflammatory condition, a pharmaceutical composition including one or more of the peptides of the present invention is provided in advance of any visible or detectable symptom. The prophylactic administration of one or more of the peptides of the present invention serves to attenuate subsequently arising symptoms or prevent symptoms from arising altogether. The route of administration of one or more of the peptides of the present invention include, but are not limited to, topical, transdermal, intranasal, pulmonary, vaginal, rectal, oral, subcutaneous, intravenous, intraarterial, intramuscular, intraosseous, intraperitoneal, epidural and intrathecal.

4.6 Methods of Administration and Use for Ocular Diseases, Indications, Conditions and Syndromes.

For ocular applications, in one aspect one or more of the peptides of the present invention are formulated in an ophthalmic dosage form and administered in the form of eye drops, eye washes or by means of other ocular delivery systems. Emulsions, ointments, gels, ocular inserts, biodegradable ocular inserts, liposomes, microparticles, nanoparticles, nanospheres or ion pairing formulations may also be employed, which may, in some instances, result in increasing the ocular residence times of a peptide of the present invention. In one embodiment, the ophthalmic formulation is a solution that includes between about 0.0000001% and about 5% (w/v) of a peptide of the present invention or a salt thereof, alternatively between about 0.000001% and about 0.2% (w/v) of a peptide of the present invention or a salt thereof, or alternatively between about 0.00001% and about 0.2% (w/v) of a peptide of the present invention or a salt thereof.

5.0 Methods of Making

In general, the peptides of the present invention may be synthesized by solid-phase synthesis and purified according to methods known in the art. Any of a number of well-known procedures utilizing a variety of resins and reagents may be used to prepare the peptides of the present invention.

The linear peptides of the present invention may be readily synthesized by known conventional procedures for the formation of a peptide linkage between amino acids. Such conventional procedures include, for example, any solution phase procedure permitting a condensation between the free alpha amino group of an amino acid or residue thereof having its carboxyl group and other reactive groups protected and the free primary carboxyl group of another amino acid or residue thereof having its amino group or other reactive groups protected. In a preferred conventional procedure, the linear peptides of the present invention may be synthesized by solid-phase synthesis and purified according to methods known in the art. Any of a number of well-known procedures utilizing a variety of resins and reagents may be used to prepare the peptides of the present invention.

The process for synthesizing the linear peptides may be carried out by a procedure whereby each amino acid in the desired sequence is added one at a time in succession to another amino acid or residue thereof or by a procedure whereby peptide fragments with the desired amino acid sequence are first synthesized conventionally and then condensed to provide the desired peptide.

Solid phase peptide synthesis methods are well known and practiced in the art. In such methods the synthesis of peptides of the invention can be carried out by sequentially incorporating the desired amino acid residues one at a time into the growing peptide chain according to the general principles of solid phase methods. These methods are disclosed in numerous references, including Merrifield, R. B., "Solid phase synthesis (Nobel lecture)," *Angew Chem* 24:799-810 (1985) and Barany et al., *The Peptides, Analysis, Synthesis and Biology*, Vol. 2, Gross, E. and Meienhofer, J., Eds. Academic Press 1-284 (1980).

In chemical syntheses of peptides, reactive side chain groups of the various amino acid residues are protected with suitable protecting groups, which prevent a chemical reaction from occurring at that site until the protecting group is removed. Also common is the protection of the alpha amino group of an amino acid residue or fragment while that entity reacts at the carboxyl group, followed by the selective removal of the alpha amino protecting group to allow a subsequent reaction to take place at that site. Specific protecting groups have been disclosed and are known in solid phase synthesis methods and solution phase synthesis methods.

Alpha amino groups may be protected by a suitable protecting group, including a urethane-type protecting group, such as benzyloxycarbonyl (Z) and substituted benzyloxycarbonyl, such as p-chlorobenzyloxycarbonyl, p-nitrobenzyloxycarbonyl, p-bromobenzyloxycarbonyl, p-biphenyl-isopropoxycarbonyl, 9-fluorenylmethoxycarbonyl (Fmoc) and p-methoxybenzyloxycarbonyl (Moz) and aliphatic urethane-type protecting groups, such as t-butyloxycarbonyl (Boc), diisopropylmethoxycarbonyl, isopropoxycarbonyl, and allyloxycarbonyl (Alloc). Fmoc is preferred for alpha amino protection.

Guanidino groups may be protected by a suitable protecting group, such as nitro, p-toluenesulfonyl (Tos), Z, pentamethylchromanesulfonyl (Pmc), adamantyloxycarbonyl, pentamethyldihydrobenzofuran-5-sulfonyl (Pbf) and Boc. Pbf and Pmc are preferred protecting groups for Arg.

The peptides of the invention described herein were prepared using solid phase synthesis, such as by means of a Symphony Multiplex Peptide Synthesizer (Rainin Instrument Company) automated peptide synthesizer, using programming modules as provided by the manufacturer and following the protocols set forth in the manufacturer's manual.

Solid phase synthesis was commenced from the C-terminal end of the peptide by coupling a protected alpha amino acid to a suitable resin. Such starting material may be prepared by attaching an alpha amino-protected amino acid by means of an amide linkage to 9-Fmoc-aminoxanthen-3-yloxy-Merrifield resin (Sieber Amide resin) or to 4-(2',4'-Dimethoxyphenyl-Fmoc-aminomethyl)phenoxy resin (Rink Amide resin), or by means of an ester linkage to a p-benzyloxybenzyl alcohol (Wang) resin, a 2-chlorotrityl chloride resin or an oxime resin, or by other means well known in the art.

Following removal of the alpha amino protecting group, the subsequent protected amino acids were coupled stepwise through repetitive cycles to add amino acids in the desired order to obtain an intermediate, protected peptide-resin. Typically, alpha amino Fmoc protecting groups are removed under basic conditions. Piperidine, piperazine, diethylamine, or morpholine (20-40% v/v) in N,N-dimethylformamide (DMF) may be used for this purpose.

The activating reagents used for coupling of the amino acids in the solid phase synthesis of the peptides are well known in the art. After the peptide is synthesized, if desired, the orthogonally protected side chain protecting groups may be removed using methods well known in the art for further derivatization of the peptide.

Reactive groups in a peptide can be selectively modified, either during solid phase synthesis or after removal from the resin. For example, peptides can be modified to obtain N-terminus modifications, such as acetylation, while on resin, or may be removed from the resin by use of a cleaving reagent and then modified. Similarly, methods for modifying side chains of amino acids are well known to those skilled in the art of peptide synthesis. The choice of modifications made to reactive groups present on the peptide will be determined, in part, by the characteristics that are desired in the peptide.

In the peptides of the present invention, in one embodiment the N-terminus group is modified by introduction of an N-acetyl group. In one aspect, a method is employed wherein after removal of the protecting group at the N-terminal, the resin-bound peptide is reacted with acetic anhydride in DMF in the presence of an organic base, such as pyridine. Other methods of N-terminus acetylation are known in the art, including solution phase acetylation, and may be employed.

The peptides can be cleaved from solid phase using any suitable reagent, such as ethylamine in DCM or various combinations of agents, such as trifluoroacetic acid (TFA), tri-isopropylsilane (TIS), dimethoxybenezene (DMB), water and the like. The resulting crude peptide is dried and remaining amino acid side chain protecting groups, if any, are cleaved using any suitable reagent, such as (TFA) in the presence of water, TIS, 2-mercaptopethane (ME), and/or 1,2-ethanedithiol (EDT). The final product is precipitated by adding cold ether and collected by filtration. Final purification is by reverse phase high performance liquid chromatography (RP-HPLC), using a suitable column, such as a $C_{18}$ column, or other methods of separation or purification, such as methods based on the size or charge of the peptide, can also be employed. Once purified, the peptide can be characterized by any number of methods, such as high performance liquid chromatograph (HPLC), amino acid analysis, mass spectrometry, and the like.

For peptides of the present invention which have a C-terminus substituted amide derivative or N-alkyl group, synthesis may proceed by solid phase synthesis commenced from the C-terminal end of the peptide by coupling a protected alpha amino acid to a suitable resin. Such methods for preparing substituted amide derivatives on solid-phase have been described in the art. See, for example, Barn, D. R., et al., "Synthesis of an array of amides by aluminum chloride assisted cleavage on resin bound esters," Tetrahedron Letters, 37:3213-3216 (1996); DeGrado, W. F. and Kaiser E. T., "Solid-phase synthesis of protected peptides on a polymer bound oxime: Preparation of segments comprising the sequences of a cytotoxic 26-peptide analogue," J. Org. Chem., 47:3258-3261 (1982). Such a starting material can be prepared by attaching an alpha amino-protected amino acid by an ester linkage to a p-benzyloxybenzyl alcohol (Wang) resin or an oxime resin by well known means. The peptide chain is grown with the desired sequence of amino acids and the peptide-resin treated with a solution of appropriate amine (such as methyl amine, dimethyl amine, ethylamine, and so on). Peptides employing a p-benzyloxybenzyl alcohol (Wang) resin may be cleaved from resin by aluminum chloride in DCM, and peptides employing an oxime resin may be cleaved by DCM. Another method to prepare a peptide with a C-terminus substituted amide is to attach an alkyl amine by reductive amination to formyl resins, such as 4-(4-Formyl-3-methoxyphenoxy)butyryl-AM resin (FMPB AM resin), following which the desired amino acid residues are incorporated into the desired peptide chain utilizing general principles of solid phase methods.

While synthesis has been described primarily with reference to solid phase Fmoc chemistry, it is to be understood that other chemistries and synthetic methods may be employed to make the linear peptides of the invention, such as by way of example and not limitation, methods employing Boc chemistry, solution chemistry, and other chemistries and synthetic methods.

6.0 Formulations

Depending on the desired route of administration, the formulation of a composition including one or more linear peptides of the present invention may be varied. Thus the formulation may be suitable for subcutaneous injection, or intravenous injection, for topical applications, for ocular applications, for nasal spray applications, for inhalation applications, for other transdermal applications and the like.

6.1 Salt Form of Linear Peptides of the Present Invention.

The linear peptides of the present invention may be in the form of any pharmaceutically acceptable salt. The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, lithium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the linear peptide of the present invention is basic, acid addition salts may be prepared from pharmaceutically acceptable non-toxic acids, including inorganic and organic acids. Such acids include acetic, benzenesulfonic, benzoic, camphorsulfonic, carboxylic, citric, ethanesulfonic, formic, fumaric, gluconic, glutamic, hydrobromic, hydrochloric, isethionic, lactic, maleic, malic, mandelic, methanesulfonic, malonic, mucic, nitric, pamoic, pantothenic, phosphoric, propionic, succinic, sulfuric, tartaric, p-toluenesulfonic acid, trifluoroacetic acid, and the like. Acid addition salts of the peptides of the present invention are prepared in a suitable solvent from the peptide and an excess of an acid, such as hydrochloric, hydrobromic, sulfuric, phosphoric, acetic, trifluoroacetic, citric, tartaric, maleic, succinic or methanesulfonic acid. The acetate, ammonium acetate and trifluoracetic acid salt forms are especially useful. Where the peptides of the present invention include an acidic moiety, suitable pharmaceutically acceptable salts may include alkali metal salts, such as sodium or potassium salts, or alkaline earth metal salts, such as calcium or magnesium salts.

6.2 Pharmaceutical Compositions.

The invention provides a pharmaceutical composition that includes a linear peptide of the present invention and a pharmaceutically acceptable carrier. The carrier may be a liquid formulation, and is preferably a buffered, isotonic, aqueous solution. Pharmaceutically acceptable carriers also include excipients, such as diluents, carriers and the like, and additives, such as stabilizing agents, preservatives, solubilizing agents, buffers and the like, as hereafter described.

The linear peptide compositions of the present invention may be formulated or compounded into pharmaceutical compositions that include at least one linear peptide of the present invention together with one or more pharmaceutically acceptable carriers, including excipients, such as diluents, carriers and the like, and additives, such as stabilizing agents, preservatives, solubilizing agents, buffers and the like, as may be desired. Formulation excipients may include polyvinylpyrrolidone, gelatin, hydroxy cellulose, acacia, polyethylene glycol, manniton, sodium chloride and sodium citrate. For injection or other liquid administration formulations, water containing at least one or more buffering constituents is preferred, and stabilizing agents, preservatives and solubilizing agents may also be employed. For solid administration formulations, any of a variety of thickening, filler, bulking and carrier additives may be employed, such as starches, sugars, fatty acids and the like. For topical administration formulations, any of a variety of creams, ointments, gels, lotions and the like may be employed. For most pharmaceutical formulations, non-active ingredients will constitute the greater part, by weight or volume, of the preparation. For pharmaceutical formulations, it is also contemplated that any of a variety of measured-release, slow-release or sustained-release formulations and additives may be employed, so that the dosage may be formulated so as to effect delivery of a peptide of the present invention over a period of time.

In general, the actual quantity of linear peptides of the present invention administered to a patient will vary between fairly wide ranges depending on the mode of administration, the formulation used, and the response desired.

In practical use, the linear peptides of the invention can be combined as the active ingredient in an admixture with a pharmaceutical carrier according to conventional pharmaceutical compounding techniques. The carrier may take a wide variety of forms depending on the form of preparation desired for administration, for example, oral, parenteral (including intravenous), urethral, vaginal, nasal, buccal, sublingual, or the like. In preparing the compositions for oral dosage form, any of the usual pharmaceutical media may be employed, such as, for example, water, glycols, oils, alcohols, flavoring agents, preservatives, coloring agents and the like in the case of oral liquid preparations such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets.

Because of their ease of administration, tablets and capsules represent an advantageous oral dosage unit form. If desired, tablets may be coated by standard aqueous or nonaqueous techniques. The amount of active peptide in such therapeutically useful compositions is such that an effective dosage will be obtained. In another advantageous dosage unit form, sublingual constructs may be employed, such as sheets, wafers, tablets or the like.

The tablets, pills, capsules, and the like may also contain a binder such as gum tragacanth, acacia, corn starch or gelatin; excipients such as dicalcium phosphate; a disintegrating agent such as corn starch, potato starch or alginic acid; a lubricant such as magnesium stearate; and a sweetening agent such as sucrose, lactose or saccharin. When a dosage unit form is a capsule, it may contain, in addition to materials of the above type, a liquid carrier such as fatty oil.

Various other materials may be utilized as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Linear peptides may also be administered parenterally. Solutions or suspensions of these active peptides can be prepared in water suitably mixed with a surfactant such as hydroxy-propylcellulose. Dispersions can also be prepared in glycerol, liquid polyethylene glycols and mixtures thereof in oils. These preparations may optionally contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that it may be administered by syringe. The form must be stable under the conditions of manufacture and storage and must be preserved against the contaminating action of microorganisms such as bacteria and fungi. The carrier can be a solvent or dispersion medium containing, for example, water, ethanol, a polyol, for example glycerol, propylene glycol or liquid polyethylene glycol, suitable mixtures thereof, and vegetable oils.

The linear peptides of the present invention may be therapeutically applied by means of nasal administration. By "nasal administration" is meant any form of intranasal administration of any of the linear peptides of the present invention. The peptides may be in an aqueous solution, such as a solution including saline, citrate or other common excipients or preservatives. The peptides may also be in a dry or powder formulation.

The linear peptides of the present invention may be formulated with any of a variety of agents that increase effective nasal absorption of drugs, including peptide drugs. These agents should increase nasal absorption without unacceptable damage to the mucosal membrane. U.S. Pat. Nos. 5,693,608, 5,977,070 and 5,908,825, among others, teach a number of pharmaceutical compositions that may be employed, including absorption enhancers, and the teachings of each of the foregoing, and all references and patents cited therein, are incorporated by reference.

If in an aqueous solution, the linear peptides may be appropriately buffered by means of saline, acetate, phosphate, citrate, acetate or other buffering agents, which may be at any physiologically acceptable pH, generally from about pH 4 to about pH 7. A combination of buffering agents may also be employed, such as phosphate buffered saline, a saline and acetate buffer, and the like. In the case of saline, a 0.9% saline solution may be employed. In the case of acetate, phosphate, citrate, and the like, a 50 mM solution may be employed. In addition to buffering agents, a suitable preservative may be employed, to prevent or limit bacteria and other microbial growth. One such preservative that may be employed is 0.05% benzalkonium chloride.

In an alternative embodiment, linear peptides of the present invention may be administered directly into the lung. Intrapulmonary administration may be performed by means of a metered dose inhaler, a device allowing self-administration of a metered bolus of a peptide of the present invention when actuated by a patient during inspiration. In one aspect of this embodiment, the linear peptide may be in a dried and particulate form, for example particles between about 0.5 and 6.0 µm, such that the particles have sufficient mass to settle on the lung surface, and not be exhaled, but are small enough that they are not deposited on surfaces of the air passages prior to reaching the lung. Any of a variety of different techniques may be used to make dry powder microparticles, including but not limited to micro-milling, spray drying and a quick freeze aerosol followed by lyophilization. With microparticles, the peptides may be deposited to the deep lung, thereby providing quick and efficient absorption into the bloodstream. Further, with such approach penetration enhancers are not required, as is sometimes the case in transdermal, nasal or oral mucosal delivery routes. Any of a variety of inhalers can be employed, including propellant-based aerosols, nebulizers, single dose dry powder inhalers and multidose dry powder inhalers. Common devices in current use include metered dose inhalers, which are used to deliver medications for the treatment of asthma, chronic obstructive pulmonary disease and the like. Preferred devices include dry powder inhalers, designed to form a cloud or aerosol of fine powder with a particle size that is always less than about 6.0 µm.

Microparticle size, including mean size distribution, may be controlled by means of the method of making. For micro-milling, the size of the milling head, speed of the rotor, time of processing and the like control the microparticle size. For spray drying, the nozzle size, flow rate, dryer heat and the like control the microparticle size. For making by means of quick freeze aerosol followed by lyophilization, the nozzle size, flow rate, concentration of aerosoled solution and the like control the microparticle size. These parameters and others may be employed to control the microparticle size.

The linear peptides of the present invention may be therapeutically administered by means of an injection of a sustained release formulation. In one embodiment, a linear peptide of the present invention is formulated for a deep intramuscular injection, such as in the gluteal or deltoid muscle, of a formulation with a polyethylene glycol, such as polyethylene glycol 3350, and optionally one or more additional excipients and preservatives, including but not limited to excipients such as salts, polysorbate 80, sodium hydroxide or hydrochloric acid to adjust pH, and the like. In another embodiment a linear peptide of the present invention is formulated with a poly(ortho ester), which may be an auto-catalyzed poly(ortho ester) with any of a variable percentage of lactic acid in the polymeric backbone, and optionally one or more additional excipients. In one embodiment poly (D,L-lactide-co-glycolide) polymer is employed. In general, any of a number of injectable and bioerodible polymers, which are preferably also adhesive polymers, may be employed in a sustained release injectable formulation. Alternatively other sustained release formulations may be employed, including formulations permitting subcutaneous injection, which other formulations may include one or more of nano/microspheres (such as compositions including PLGA polymers), liposomes, emulsions (such as water-in-oil emulsions), gels, insoluble salts or suspensions in oil. The formulation may be such that an injection is required on a daily, weekly, monthly or other periodic basis, depending on the concentration and amount of linear peptide, the sustained release rate of the materials employed, and other factors known to those of skill in the art.

6.3 Oral Formulations of Peptides of the Present Invention.

In one aspect, the peptides of the present invention are formulated for oral delivery. The peptide is preferably formulated and made such that it is encased in an enteric protectant, more preferably such that it is not released until the tablet or capsule has transited the stomach, and optionally has further transited a portion of the small intestine. In the context of this application it will be understood that the term enteric coating or material refers to a coating or material that will pass through the stomach essentially intact but will rapidly disintegrate in the small intestine to release the active drug substance. One enteric coating solution that may be used includes cellulose acetate phthalate, and optionally other ingredients such as ammonium hydroxide, triacetin, ethyl alcohol, methylene blue, and purified water. Cellulose acetate phthalate is a polymer that has been used in the pharmaceutical industry for enterically coating individual dosage forms such as tablets and capsules, and is not soluble in water at a pH of less than about 5.8. Enteric coatings including cellulose acetate phthalate provide protection against the acidic environment of the stomach, but begin to dissolve in environment of the duodenum (pH of about 6-6.5), and are completely dissolved by the time the dosage form reaches the ileum (pH of about 7-8). In addition to cellulose acetate phthalate, other enteric coating materials are known and may be used with peptides of the present invention, including without limitation hydroxypropylmethylethylcellulose succinate, hydroxypropylmethylcellulose phthalate, polyvinyl acetate phthalate, and methacrylic acid-methyl methacrylate copolymer. The enteric coating employed promotes dissolution of the dosage form primarily at a site outside the stomach, and may be selected such that the enteric coating dissolves at a pH of approximately at least 6.0, more preferable at a pH of from about 6.0 to about 8.0. In one preferred aspect, the enteric coating dissolves and breaks down in the proximity of the ileum.

Any of a variety of permeation enhancers may be employed, to increase uptake in the intestines upon dissolution of the enteric coating. In one aspect, permeation enhancers increase either paracellular or transcellular transport systems. An increase in paracellular transport can be achieved by opening the tight junctions of the cells; an increase in transcellular transport can be achieved by increasing the fluidity of the cell membrane. Representative, non-limiting examples of such permeation enhancers include calcium chelators, bile salts (such as sodium cholate), and fatty acids. The peptides of the present invention may be in an enteric-coated individual dosage form that includes a fatty acid, such as for example oleate, palmitate, stearate, sodium caprate, or conjugated linoleic acid, in an enteric-coated capsule, to increase paracellular transport.

In one aspect, the individual dosage form, such as a tablet or capsule, optionally further includes common pharmaceutical binders such as povidone, diluents, glidants, fillers such as microcrystalline cellulose, lubricants such as magnesium stearate, disintegrants such as croscarmellose sodium, preservatives, colorants and the like in their usual known sizes and amounts. In some embodiments, peptides or polypeptides that act as substrates for intestinal proteases are further added.

6.4 Ophthalmic Formulations.

In one embodiment, ocular diseases, indications, conditions and syndromes, such as for example either dry eye disease or uveitis, may be treated with an ophthalmic dosage form including one or more of the peptides of the present invention. The ophthalmic dosage form may include one or more active ingredients in addition to one or more of the peptides of the present invention, such as for example artificial tear components, topical corticosteroids, non-steroidal anti-inflammatory drugs, or calcineurin inhibitors such as cyclosporine-A (RESTASIS®-Allergan). In a related embodiment, one or additional compounds may be given separately from one or more of the peptides of the present invention, such as separate administration of an ophthalmic dosage form including an artificial tear component, a topical corticosteroid, a non-steroidal anti-inflammatory drugs, a calcineurin inhibitor such a cyclosporine-A, or a combination of any of the foregoing.

Ophthalmic solutions are preferably maintained in a pH range between about pH 3.5 to 9.0, and preferably about pH 6.5 and pH 7.2, with a suitable buffer. The pH may be adjusted by any known means, such as by use of HCl or NaOH. Buffers may include acetate, boric acid, sodium borate, potassium citrate, citric acid, sodium bicarbonate, TRIS, various mixed phosphate buffers (such as combinations of $Na_2HPO_4$, $NaH_2PO_4$ and $KH_2PO_4$) and mixtures thereof. Generally, buffers will be used in amounts ranging from about 0.05% to 2.5% (w/v), and preferably from about 0.1% to 1.5% percent; buffers should be as close to physiological ion concentrations as possible to minimize potential irritation but still maintain drug product pH over the shelf life of the product.

The ophthalmic solutions employed in the present invention may be made from purified water, and in one aspect preferably from a physiological saline solution. Additional tonicity enhancing agents may be employed, including either ionic or non-ionic tonicity enhancing agents, or both. Ionic tonicity enhancing agents include alkali metal or earth metal halides, such as $CaCl_2$, KBr, KCl, LiCl, NaI, NaBr, NaCl, $Na_2SO_4$ or boric acid. Non-ionic tonicity enhancing agents include urea, glycerol, sorbitol, mannitol, propylene glycol, or dextrose. The aqueous solutions of the present invention are typically adjusted with tonicity agents to approximate an osmotic pressure equivalent to a 0.9% (w/v) solution of sodium chloride or a 2.5% solution of glycerol. However, tonicity ranges equivalent to between 0.7% and 1.5% NaCl are generally considered to be acceptable.

The solutions can also contain conventional, pharmaceutically acceptable preservatives, stabilizers, cosolvents and/or penetration enhancers as well as viscoelastic substances included in artificial tear preparations. Pharmaceutically acceptable preservatives include quaternary ammonium compounds such as benzalkonium chloride, benzoxonium chloride or the like; alkyl-mercury salts of thiosalicylic acid such as thiomersal, phenylmercuric nitrate, phenylmercuric acetate or phenylmercuric borate; sodium perborate; sodium chlorite; parabens, such asmethylparaben or propylparaben; alcohols such as chlorobutanol, benzyl alcohol or phenyl ethanol; guanidine derivatives such as chlorohexidine or polyhexamethylene biguanide; sorbic acid; boric acid; or peroxide forming preservatives, or combinations of two or more of the foregoing. Pharmaceutically acceptable antioxidants and chelating agents may be used including various sulphites (such as sodium metabisulphite, sodium thiosulphate, sodium bisulfite, or sodium sulfite), α-tocopherol, ascorbic acid, acetylcysteine, 8-hydroxyquinolome, antipyrine, butylated hydroxyanisole or butylated hydroxytoluene, EDTA, and others. Cosolvents such as alcohols and others may also be used. Various substances can also be used to enhance formulation stability, such as cyclodextrins.

Penetration enhancers may be employed in ophthalmic solutions, including compounds such as surfactants, certain organic solvents such as dimethylsulphoxide and other sulphoxides, dimethylacetamide and pyrrolidine, certain amides of heterocyclic amines, glycols (e.g. propylene glycol), propylene carbonate, oleic acid, alkylamines and derivatives, various cationic, anionic and nonionic surfactants, amphoteric surfactants and the like. Additional penetration enhancers that may be employed include cetylpyridinium chloride, ionophores such as lasalocid, benzalkonium chloride, polysorbates such as polysorbate 20 (TWEEN® 20), parabens, saponins, various polyoxyethylene ether compounds such as BRIJ® 35, BRIJ® 78 or BRIJ® 98, ethylenediaminetetraacetic acid (EDTA), bile salts, and bile acids (such as sodium cholate, sodium taurocholate, sodium glycodeoxycholate, sodium taurodeoxycholate, taurocholic acid, chenodeoxycholic acid and ursodeoxycholic acid), capric acid, azone, fucidic acid, hexamethylene lauramide, saponins, hexamethylene octanamide, and decylmethyl sulfoxide. Ion pairing formulations utilizing charged excipients or counter ions to shield/neutralize charged groups on drug molecules may also be employed to lower the lipophilicity of the compound to increase corneal penetration. These formulations include but are not limited to ions such as sorbic acid, boric acid and maleic acid, among other charged ion pairing agents.

Viscosity enhancers or lubricants may be employed as necessary or appropriate. In one aspect, the viscosity enhancer includes a water soluble polymer, such as polyols, including polyvinyl alcohol, a polyethylene glycol, or combinations of water soluble polymers. In one aspect, polyethylene glycol 300 or 400 is employed. The contents of water soluble polymer may be between about 0.25% and about 4.0% (w/v). Thus an ophthalmic solution can include, by way of example, 1% of polyvinyl alcohol, 1% of polyethylene glycol 300 or 400, or both. Other polyols may be employed, including glycerol, glycerin, polysorbate 80, propylene glycol, ethylene glycol, povidone, and polyvinylpyrrolidone. Other lubricants, sometimes also called tear substitutes, may also be employed, including cellulose derivatives such hydroxypropyl methyl cellulose, carboxymethyl cellulose sodium, hydroxypropyl cellulose, hydroxyethyl cellulose, and methyl cellulose; dextrans such as dextran 70; water soluble proteins such as gelatin; carbomers such as carbomer 934P, carbomer 941, carbomer 940 and carbomer 974P; and gums such as HP-guar, xanthan gum or combinations thereof. Other viscosity enhancers that can be employed include polysaccharide compounds, such as sulfated or non-sulfated glycosaminoglycan compounds. In one aspect, the polysaccharide compound is a non-sulfated glycosaminoglycan such as hyaluronic acid or a pharmaceutically acceptable salt thereof, such as sodium hyaluronate. Any commercially available molecular weight range of hyaluronic acid or salts thereof may be employed. From about 0.05% to about 0.4% (w/v) of hyaluronic acid or a salt thereof may be employed in an ophthalmic solution. In another aspect, the polysaccharide compound is a non-sulfated glycosaminoglycan such as dextran. In yet another aspect, the polysaccharide is a sulfated glycosaminoglycan such as chondroitin sulfate.

Semi-solid formulations may be employed for ophthalmic delivery to increase corneal residence times of drug molecules. Ointments containing polyethylene glycols, lanolin alcohols, ozokerite, ceresin, microcrystalline wax, surfactants, preservatives, sorbitan monolaurate, white petrolatum and light liquid petrolatum (mineral oil) or other petrolatum like bases may be used. Aqueous or non-aqueous suspensions may also be used. For hydrophilic peptides, suspensions using pharmaceutically acceptable oils or petrolatum may be used. Suspensions may contain microspheres or microparticulates, nanoparticulates, mucoadhesive particles, viscosity increasing agents, surfactants and other agents. Mucoadhesive compounds include synthetic polymers, such as polyacrylic acid and polycarbophil; biopolymers such as hyaluronic acid or sodium carboxy methylcellulose (CMC); polyanionic polymers such as polyacrylic acid (PAA); polyacrylic acids such as Carbopol® 934P, polycarbophil, and CMC or PAA with PLURONIC® polyoxalkylene ethers; or polycationic polymers such as chitosan. Emulsions (oil in water or water in oil), including microemulsions, may also be employed that are composed of pharmaceutically acceptable oils together with one or more of viscosity increasing agents, preservatives, cosolvents, surfactants and other agents. Pharmaceutically acceptable oils include mineral oils and organic oils, including oils comprising medium chain or long chain saturated or unsaturated fatty acids or esters thereof. Pharmaceutically acceptable oils thus include any of a range of medium chain triglycerides, as well as oils such as almond oil, castor oil, cottonseed oil, glycerin (glycerol), peanut oil, mineral oil, polyethylene glycol, poppyseed oil, propylene glycol, safflower oil, sesame oil, soybean oil, olive oil and vegetable oil. A surfactant such as a polyoxyethylene alkyl ether, polyoxyl castor oil, tyloxapol, alkyl aryl ether sulfonate, lecithin, sorbitan esters, glyceryl monostearate, cetyl alcohol, octoxynol-9, nonoxynol-9, polyoxyethylene stearates, polyoxyethylene sorbitan fatty acid esters such as polysorbate 20, 60 and 80 or others may also be employed. Aqueous gels, often comprised of polymers such as polyvinyl alcohol (PVA), polyacrylamide, poloxamer, hydroxypropyl methylcellulose (HPMC), carbomer, polymethylvinylether maleic anhydride, and hydroxypropyl ethylcellulose may also be used. Hydrogels containing swellable, water insoluble polymers may be utilized containing polymers such as poly(acrylic acid), poly(acrylic acids), poly(acrylamide), and ethylene maleic anhydride, and chemically or thermally-treated gelatins. Ocular inserts, liposomes, discomes, niosomes, dedrimers, nanosuspensions, nanoparticles and microparticles may also be used to provide a controlled release of the drug. Liposomes and other controlled release agents may be positively charged to increase residence times through ionic interactions with the negatively charged corneal surface. Nanoparticles may be composed of biodegradable polymers such as polyactides (PLAs), polycyano acrylates, poly (D,L-lactides), and natural polymers such as chitosan, gelatin, sodium alginate, albumin and others.

6.5 Routes of Administration of Formulations.

If a formulation including one or more peptides of the present invention is administered by injection, the injection may be intravenous, subcutaneous, intramuscular, intraperitoneal or other means known in the art. The peptides of the present invention may be formulated by any means known in the art, including but not limited to formulation as tablets, capsules, caplets, suspensions, powders, lyophilized preparations, suppositories, ocular drops, skin patches, oral soluble formulations, sprays, aerosols and the like, and may be mixed and formulated with buffers, binders, excipients, stabilizers, anti-oxidants and other agents known in the art. In general, any route of administration by which the peptides of invention are introduced across an epidermal layer of cells may be employed. Administration means may thus include formulations for administration through mucous membranes, buccal administration, oral administration, dermal administration, inhalation administration, nasal administration, urethral administration, vaginal administration, and the like.

6.6 Therapeutically Effective Amount.

In general, the actual quantity of linear peptide of the present invention administered to a patient will vary between fairly wide ranges depending upon the mode of administration, the formulation used, and the response desired. The dosage for treatment is administration, by any of the foregoing means or any other means known in the art, of an amount sufficient to bring about the desired therapeutic effect. Thus a therapeutically effective amount includes an amount of a peptide or pharmaceutical composition of the present invention that is sufficient to therapeutically alleviate sexual dysfunction in a patient, or to prevent or delay onset or recurrence of the sexual dysfunction.

In general, the linear peptides of the present invention are highly active. For example, the linear peptide can be systemically administered at about 0.1, 0.5, 1, 5, 50, 100, 500, 1000 or 5000 μg/kg body weight, depending on the specific peptide selected, the desired therapeutic response, the route of administration, the formulation and other factors known to those of skill in the art.

7.0 Peptides of the Present Invention

In one aspect, the invention provides a linear peptide which contains a core sequence derived Phe-Arg-Xaa$^5$-Trp or His-Phe-Arg-Xaa$^5$-Trp. The core sequence derived from (His)-Phe-Arg-Xaa$^5$-Trp may include a number of substitutions. The His position, if present, may be His, or may be a substituted or unsubstituted Pro or an amino acid with a side chain including at least one primary amine, secondary amine, alkyl, cycloalkyl, cycloheteroalkyl, aryl, heteroaryl, alcohol, ether, sulfide, sulfone, sufoxide, carbomyl or carboxyl. Substituted Pro includes, but is not limited to, amino acids such as Hyp, Hyp(Bzl), Pro(4R-Bzl) or Pro(4R-NH$_2$). The Phe position may be Phe, but is most typically substituted or unsubstituted D-Phe, D-Nal 1, D-Nal 2 or an amino acid with a side chain including pyridyl. The Arg position may be Arg, Lys, Orn, Dab or Dap, or a substituted or unsubstituted Pro, or Cit, or may be an amino acid with a side chain including at least one primary amine, secondary amine, guanidine, urea, alkyl, cycloalkyl, cycloheteroalkyl, aryl, heteroaryl, or ether. Xaa$^5$ may be Gly, Sar, an L- or D-isomer of Pro or an amino acid with a side chain consisting of linear or branched alkyl, cycloalkyl, alkylcycloalkyl, aryl, or alkylaryl. The Trp position may be an amino acid with a side chain including at least one substituted or unsubstituted aryl or heteroaryl, such as Trp, Nal 1 or Nal 2.

The invention thus provides a linear peptide of formula (VI):

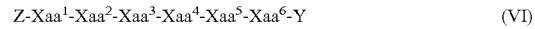

Z-Xaa$^1$-Xaa$^2$-Xaa$^3$-Xaa$^4$-Xaa$^5$-Xaa$^6$-Y  (VI)

or a pharmaceutically acceptable salt thereof, wherein:

Z is H or an N-terminal group;

Xaa$^1$ is optionally present, and if present is from one to three amino acid residues;

Xaa$^2$ is L- or D-Pro, optionally substituted with hydroxyl, halogen, sulfonamide, alkyl, —O-alkyl, aryl, alkyl-aryl, alkyl-O-aryl, alkyl-O-alkyl-aryl, or —O-aryl, or Xaa$^2$ is an L- or D-isomer amino acid with a side chain including at least one primary amine, secondary amine, alkyl, cycloalkyl, cycloheteroalkyl, aryl, heteroaryl, ether, sulfide, or carboxyl;

Xaa$^3$ is an L- or D-isomer amino acid with a side chain including phenyl or naphthyl, optionally substituted with one or more substituents independently selected from halo, (C$_1$-C$_{10}$)alkyl-halo, (C$_1$-C$_{10}$)alkyl, (C$_1$-C$_{10}$)alkoxy, (C$_1$-C$_{10}$)alkylthio, aryl, aryloxy, nitro, nitrile, sulfonamide, amino, monosubstituted amino, disubstituted amino, hydroxy, carboxy, and alkoxy-carbonyl;

Xaa$^4$ is L- or D-Pro or Xaa$^4$ is an L- or D-isomer amino acid with a side chain including at least one primary amine, secondary amine, guanidine, urea, alkyl, cycloalkyl, cycloheteroalkyl, aryl, heteroaryl, or ether;

Xaa$^6$ is Gly, Sar, an L- or D-isomer of Pro or an amino acid with a side chain consisting of linear or branched alkyl, cycloalkyl, alkylcycloalkyl, aryl, or alkylaryl, Xaa⁶ is an L- or D-amino acid with a side chain including at least one aryl or heteroaryl; and Y is a C-terminal group.

In another aspect, $Xaa^1$ may be an amino acid with a side chain including a linear or branched alkyl, cycloalkyl, cycloheteroalkyl, aryl or heteroaryl.

In another aspect, the N-terminal group may be a $C_1$ to $C_7$ acyl group, a linear or branched $C_1$ to $C_{17}$ alkyl, aryl, heteroaryl, alkene, alkenyl, or aralkyl chain or an N-acylated linear or branched $C_1$ to $C_{17}$ alkyl, aryl, heteroaryl, alkene, alkenyl, or aralkyl chain.

In another aspect, Y may be a hydroxyl, an amide, or an amide substituted with one or two linear or branched $C_1$ to $C_{17}$ alkyl, cycloalkyl, aryl, alkyl cycloalkyl, aralkyl, heteroaryl, alkene, alkenyl, or aralkyl chains.

In the foregoing and in formula (I), substituted Pro, where provided, may be, for example, Hyp, Hyp(Bzl), Pro(4-Bzl), and Pro(4-NH₂).

The peptides encompassed within formulas (I) through (VI) contain one or more asymmetric elements such as stereogenic centers, stereogenic axes and the like, so that the peptides encompassed within formula (I) can exist in different stereoisomeric forms. For both specific and generically described peptides, including the peptides encompassed within formulas (I) through (VI), all forms of isomers at all chiral or other isomeric centers, including enantiomers and diastereomers, are intended to be covered herein. The peptides of the invention each include multiple chiral centers, and may be used as a racemic mixture or an enantiomerically enriched mixture, in addition to use of the peptides of the invention in enantiopure preparations. Typically, the peptides of the invention will be synthesized with the use of chirally pure reagents, such as specified L- or D-amino acids, using reagents, conditions and methods such that enantiomeric purity is maintained, but it is possible and contemplated that racemic mixtures may be made. Such racemic mixtures may optionally be separated using well-known techniques and an individual enantiomer may be used alone. In cases and under specific conditions of temperature, solvents and pH wherein peptides may exist in tautomeric forms, each tautomeric form is contemplated as being included within this invention whether existing in equilibrium or predominantly in one form. Thus a single enantiomer of a peptide of formula (I), which is an optically active form, can be obtained by asymmetric synthesis, synthesis from optically pure precursors, or by resolution of the racemates.

The invention is further intended to include prodrugs of the present peptides, which on administration undergo chemical conversion by metabolic processes before becoming active pharmacological peptides. In general, such prodrugs will be functional derivatives of the present peptides, which are readily convertible in vivo into a peptide of formula (I) through (VI). Prodrugs are any covalently bonded compounds, which release the active parent peptide drug of formula (I) through (VI) in vivo. Conventional procedures for the selection and preparation of suitable prodrug derivatives are described, for example, in "Design of Prodrugs", ed. H. Bundgaard, Elsevier, 1985. Typical examples of prodrugs have biologically labile protecting groups on a functional moiety, such as for example by esterification of hydroxyl, carboxyl or amino functions. Thus by way of example and not limitation, a prodrug includes peptides of formula (I) wherein an ester prodrug form is employed, such as, for example, lower alkyl esters of an R group of formula (I), such as where R is —OH, which lower alkyl esters may include from 1-8 carbons in an alkyl radical or aralkyl esters which have 6-12 carbons in an aralkyl radical. Broadly speaking, prodrugs include compounds that can be oxidized, reduced, aminated, deaminated, hydroxylated, dehydroxylated, hydrolyzed, dehydrolyzed, alkylated, dealkylated, acylated, deacylated, phosphorylated or dephosphorylated to produce an active parent peptide drug of formula (I) in vivo.

The subject invention also includes peptides which are identical to those recited in formula (I) through (III), but for the fact that one or more atoms depicted in formula (I) through (III) are replaced by an atom having an atomic mass or mass number different from the atomic mass or mass number usually found in nature. Examples of isotopes that can be incorporated into compounds of the invention include isotopes of hydrogen, carbon, nitrogen and oxygen, such as $^2H$, $^3H$, $^{13}C$, $^{14}C$, $^{15}N$, $^{18}O$ and $^{17}O$, respectively. Peptides of the present invention and pharmaceutically acceptable salts or solvates of said compounds which contain the aforementioned isotopes and/or other isotopes of other atoms are within the scope of this invention. Certain isotopically-labeled compounds of the present invention, for example those into which radioactive isotopes such as $^3H$ and $^{14}C$ are incorporated, may have use in a variety of assays, such as in drug and/or substrate tissue distribution assays. Substitution with heavier isotopes, such as substitution of one or more hydrogen atoms with deuterium ($^2H$), can provide pharmacological advantages in some instances, including increased metabolic stability. Isotopically labeled peptides of formula (I) through (VI) can generally be prepared by substituting an isotopically labeled reagent for a non-isotopically labeled reagent.

8.0 Tests and Assays Employed in Evaluation of the Peptides of the Present Invention The melanocortin receptor-specific peptides of the present invention of this invention may be tested by a variety of assay systems and animal models to determine binding, functional status and efficacy.

8.1 Competitive Inhibition Assay Using [$I^{125}$]-NDP-α-MSH.

A competitive inhibition binding assay was performed using membrane homogenates prepared from HEK-293 cells that express recombinant hMCR-1a or hMCR-4 (in each instance where the h prefix refers to human), or alternatively membrane homogenates from B16-F10 mouse melanoma cells containing endogenous murine MCR-1. In the examples that follow, all MCR-1 and MCR-4 values are for human recombinant receptors, unless otherwise noted. Assays were performed in 96 well polypropylene round-bottom plates (VWR catalog number 12777-030). Membrane homogenates were incubated with 0.1 nM [$I^{125}$]-NDP-α-MSH (Perkin Elmer) and increasing concentrations of test peptides of the present invention in buffer containing 25 mM HEPES buffer (pH 7.5) with 100 mM NaCl, 2 mM $CaCl_2$, 2 mM $MgCl_2$, 0.3 mM 1,10-phenanthroline, and 0.2% bovine serum albumin. After incubation for 90 minutes at 37° C., the assay mixture was filtered onto GF/B Unifilter plates (Perkin-Elmer catalog number 6005177) and washed with 3 mL of ice-cold buffer per well. Filters were air dried and 35 μL of scintillation cocktail added to each well. Plates were counted in a Microbeta counter for bound radioactivity. Non-specific binding was measured by inhibition of binding of [$I^{125}$]-NDP-α-MSH in the presence of 1 μM NDP-α-MSH. Maximal specific binding (100%) was defined as the difference in radioactivity (cpm) bound to cell membranes in the absence and presence of 1 μM NDP-α-MSH. Each assay was conducted in duplicate and the actual mean values are described, with results less than 0% reported as 0%. Ki values for peptides of the present invention were determined using Graph-Pad PRISM® curve-fitting software.

8.2 Assay for Agonist Activity.

Accumulation of intracellular cAMP was examined as a measure of the ability of the peptides of the present invention to elicit a functional response in a human melanoma cell line, HBL, that express hMCR-1 (see Kang, L., et al., "A selective small molecule agonist of melanocortin-1 receptor inhibits lipopolysaccharide-induced cytokine accumulation and leukocyte infiltration in mice," *J. Leuk. Biol.* 80:897-904 (2006)) or HEK-293 cells that express hMCR-4. Confluent HBL cells that express hMCR-1 or HEK-293 cells that express recombinant hMCR-4 were detached from culture plates by incubation in enzyme-free cell dissociation buffer. Dispersed cells were suspended in Earle's Balanced Salt Solution containing 10 mM HEPES (pH 7.5), 1 mM $MgCl_2$, 1 mM glutamine, 0.5% albumin and 0.3 mM 3-isobutyl-1-methyl-xanthine (IBMX), a phosphodiesterase inhibitor. The cells were plated in 96-well plates at a density of $0.4 \times 10^5$ cells per well for HBL cells and $0.5 \times 10^5$ cells per well for HEK-293 cells and pre-incubated for 10 minutes. Cells were exposed for 15 minutes at 37° C. to peptides of the present invention dissolved in DMSO (final DMSO concentration of 1%) at a concentration range of 0.05-5000 nM in a total assay volume of 200 μL. NDP-α-MSH was used as the reference agonist. cAMP levels were determined by an HTRF® cAMP cell-based assay system from Cisbio Bioassays utilizing cryptate-labeled anti-cAMP and d2-labeled cAMP, with plates read on a Perkin-Elmer Victor plate reader at 665 and 620 nM. Data analysis was performed by nonlinear regression analysis with Graph-Pad PRISM® software. Maximum efficacy ($E_{max}$) values were determined for each test peptide of the present invention, compared to that achieved by the reference melanocortin agonist NDP-α-MSH.

9.0 Examples

Peptides of the following structures were synthesized and purified as described in Section 5 above, with the resulting peptide having the structure depicted. After synthesis and purification, the foregoing peptide was tested as described in Section 8 above, and average MCR-1 and MCR-4 Ki values determined as indicated. All Ki values were determined using $[I^{125}]$-NDP-α-MSH. All results are expressed in nM except for $E_{max}$ values, which are percentage values.

9.1 Ac-Nle-Ala-His-D-Phe-Arg-Ala-Trp-$NH_2$ (SEQ ID NO:4)

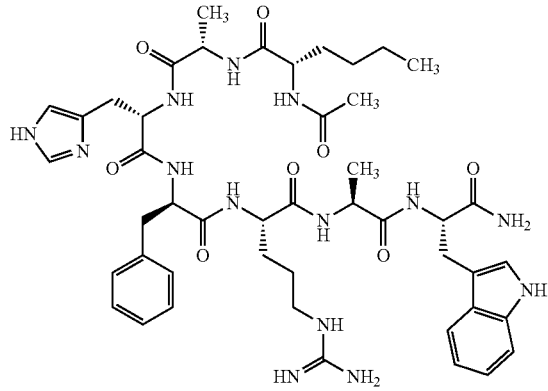 [SMILES: CCCC[C@H](NC(C)=O)C(=O)N[C@@H](C)C(=O)N[C@@H](Cc1c[nH]cn1)C(=O)N[C@H](Cc1ccccc1)C(=O)N[C@@H](CCCNC(=N)N)C(=O)N[C@@H](C)C(=O)N[C@@H](Cc1c[nH]c2ccccc12)C(N)=O]

| Assay | Result |
|---|---|
| MC-4 Ki (average) | 1735 |
| MC-1 Ki (average) | 0.2 |
| MC-1 $EC_{50}$ (average; cAMP HBL) | 0.02 |
| MC-1 $E_{max}$ (average; cAMP HBL) | 96% |

9.2 Ac-Nle-Ala-His-D-Phe-Arg-Pro-Trp-$NH_2$ (SEQ ID NO:5)

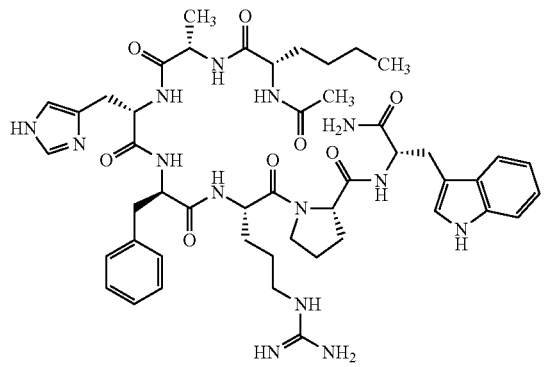 [SMILES: CCCC[C@H](NC(C)=O)C(=O)N[C@@H](C)C(=O)N[C@@H](Cc1c[nH]cn1)C(=O)N[C@H](Cc1ccccc1)C(=O)N[C@@H](CCCNC(=N)N)C(=O)N1CCC[C@H]1C(=O)N[C@@H](Cc1c[nH]c2ccccc12)C(N)=O]

| Assay | Result |
|---|---|
| MC-4 Ki (average) | 20 |
| MC-1 Ki (average) | 185 |
| MC-1 $EC_{50}$ (average; cAMP HBL) | 9 |
| MC-1 $E_{max}$ (average; cAMP HBL) | 78% |

9.3 Ac-Nle-His-D-Phe-Arg-Ala-Trp-$NH_2$ (SEQ ID NO:6)

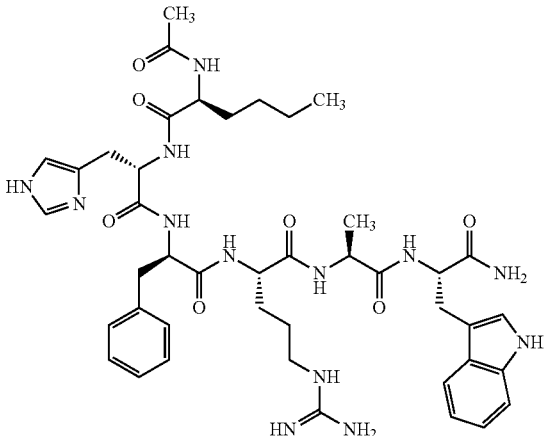

| Assay | Result |
|---|---|
| MC-4 Ki (average) | 3425 |
| MC-1 Ki (average) | 35 |
| MC-1 $EC_{50}$ (average; cAMP HBL) | 1 |
| MC-1 $E_{max}$ (average; cAMP HBL) | 95% |

9.4 Ac-Nle-Ala-His-D-Phe-Arg-Sar-Trp-NH$_2$ (SEQ ID NO:7)

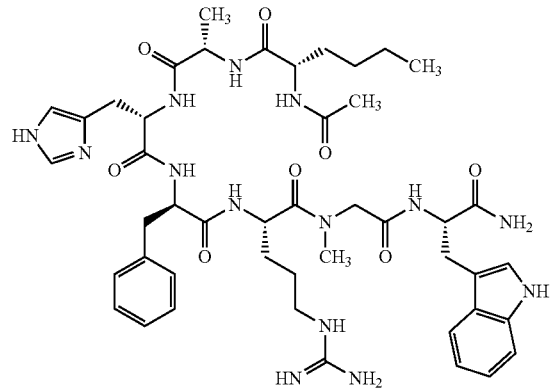 [SMILES: CCCC[C@H](NC(C)=O)C(=O)N[C@@H](C)C(=O)N[C@@H](Cc1c[nH]cn1)C(=O)N[C@H](Cc1ccccc1)C(=O)N[C@@H](CCCNC(=N)N)C(=O)N(C)CC(=O)N[C@@H](Cc1c[nH]c2ccccc12)C(N)=O]

| Assay | Result |
|---|---|
| MC-4 Ki (average) | 870 |
| MC-1 Ki (average) | 2 |
| MC-1 EC$_{50}$ (average; cAMP HBL) | 0.17 |
| MC-1 E$_{max}$ (average; cAMP HBL) | 77% |

9.5 Ac-Nle-Ala-His-D-Phe-Arg-Gly-Trp-NH$_2$ (SEQ ID NO:8)

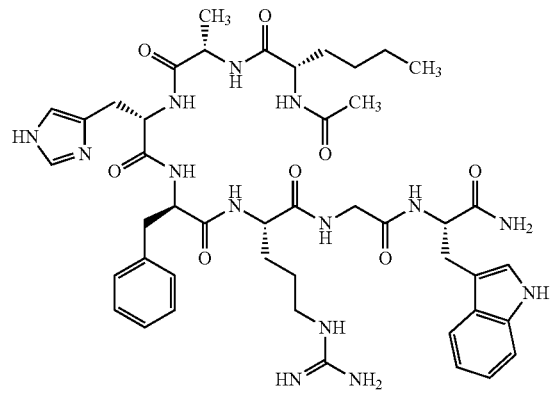 [SMILES: CCCC[C@H](NC(C)=O)C(=O)N[C@@H](C)C(=O)N[C@@H](Cc1c[nH]cn1)C(=O)N[C@H](Cc1ccccc1)C(=O)N[C@@H](CCCNC(=N)N)C(=O)NCC(=O)N[C@@H](Cc1c[nH]c2ccccc12)C(N)=O]

| Assay | Result |
|---|---|
| MC-4 Ki (average) | 885 |
| MC-1 Ki (average) | 0.8 |
| MC-1 EC$_{50}$ (average; cAMP HBL) | 0.038 |
| MC-1 E$_{max}$ (average; cAMP HBL) | 90% |

9.6 Ac-Nle-Ala-His-Phe-Arg-Ala-Trp-NH$_2$ (SEQ ID NO:9)

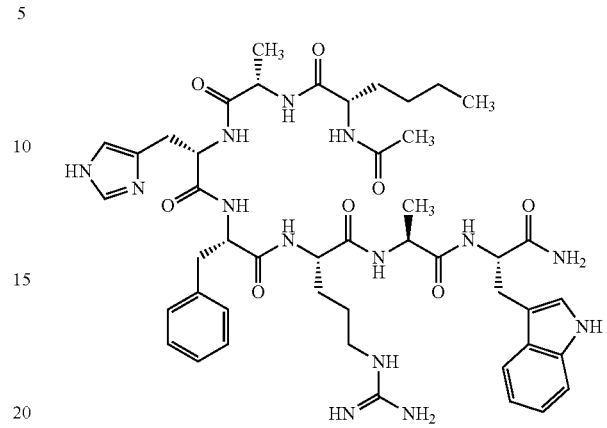

| Assay | Result |
|---|---|
| MC-4 Ki (average) | 10000 |
| MC-1 Ki (average) | 85 |
| MC-1 EC$_{50}$ (average; cAMP HBL) | 4 |
| MC-1 E$_{max}$ (average; cAMP HBL) | 72% |

9.7 Ac-Nle-Ala-His-Phe-Arg-Gly-Trp-NH$_2$ (SEQ ID NO:10)

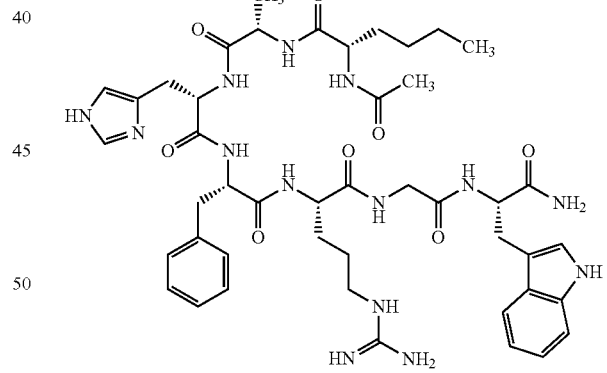

| Assay | Result |
|---|---|
| MC-4 Ki (average) | 10000 |
| MC-1 Ki (average) | 340 |
| MC-1 EC$_{50}$ (average; cAMP HBL) | 21 |
| MC-1 E$_{max}$ (average; cAMP HBL) | 75% |

9.8 Ac-Nle-His-Phe-Arg-Ala-Trp-NH₂ (SEQ ID NO:11)

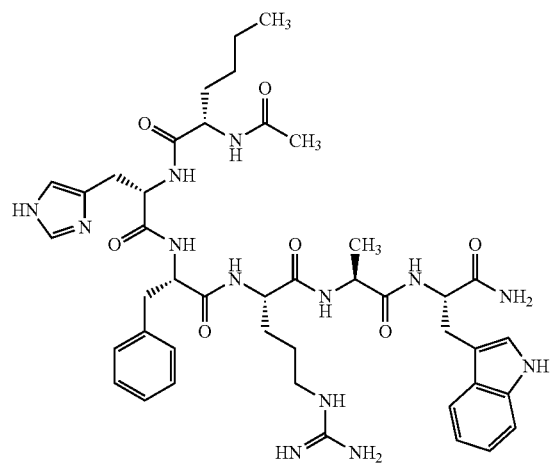 [SMILES: CCCC[C@H](NC(C)=O)C(=O)N[C@@H](Cc1c[nH]cn1)C(=O)N[C@@H](Cc1ccccc1)C(=O)N[C@@H](CCCNC(=N)N)C(=O)N[C@@H](C)C(=O)N[C@@H](Cc1c[nH]c2ccccc12)C(N)=O]

| Assay | Result |
|---|---|
| MC-4 Ki (average) | 10000 |
| MC-1 Ki (average) | 5925 |
| MC-1 EC$_{50}$ (average; cAMP HBL) | NA |
| MC-1 E$_{max}$ (average; cAMP HBL) | 55% |

9.9 Ac-Nle-Ala-His-D-Phe-Arg-Ala-D-Trp-NH₂ (SEQ ID NO:12)

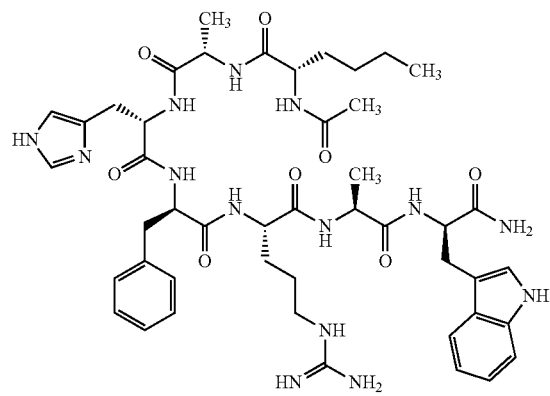 [SMILES: CCCC[C@H](NC(C)=O)C(=O)N[C@@H](C)C(=O)N[C@@H](Cc1c[nH]cn1)C(=O)N[C@H](Cc1ccccc1)C(=O)N[C@@H](CCCNC(=N)N)C(=O)N[C@@H](C)C(=O)N[C@H](Cc1c[nH]c2ccccc12)C(N)=O]

| Assay | Result |
|---|---|
| MC-4 Ki (average) | 215 |
| MC-1 Ki (average) | 7 |
| MC-1 EC$_{50}$ (average; cAMP HBL) | 0.6 |
| MC-1 E$_{max}$ (average; cAMP HBL) | 70% |

9.10 Ac-Nle-Ala-D-Phe-Arg-Ala-Trp-NH₂ (SEQ ID NO:13)

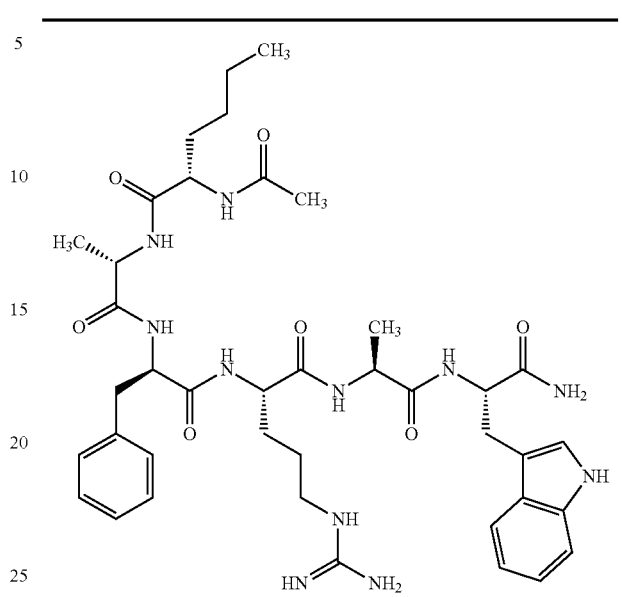

| Assay | Result |
|---|---|
| MC-4 Ki (average) | 10000 |
| MC-1 Ki (average) | 6675 |
| MC-1 EC$_{50}$ (average; cAMP HBL) | NA |
| MC-1 E$_{max}$ (average; cAMP HBL) | 85% |

9.11 Ac-Nle-Ala-His-D-Phe-Arg-D-Pro-Trp-NH₂ (SEQ ID NO:14)

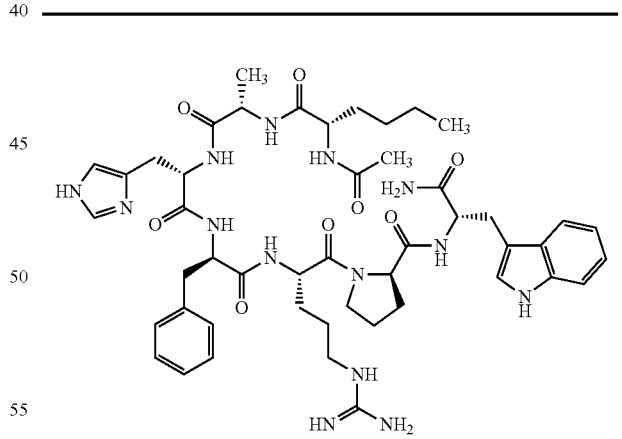

| Assay | Result |
|---|---|
| MC-4 Ki (average) | 6200 |
| MC-1 Ki (average) | 14 |
| MC-1 EC$_{50}$ (average; cAMP HBL) | 1 |
| MC-1 E$_{max}$ (average; cAMP HBL) | 70% |

9.12  Ac-Nle-Ala-His-D-Phe-Arg-D-Pro-D-Trp-NH$_2$ (SEQ ID NO:15)

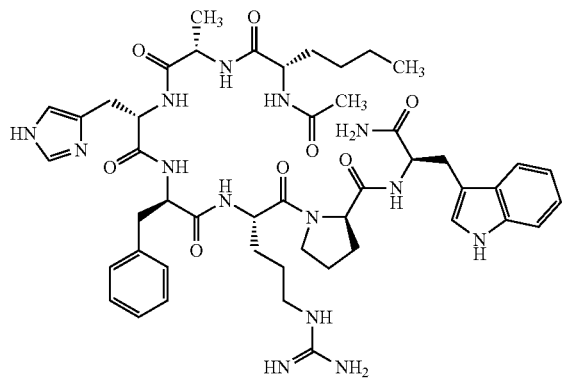 [SMILES: CCCC[C@H](NC(C)=O)C(=O)N[C@@H](C)C(=O)N[C@@H](Cc1c[nH]cn1)C(=O)N[C@H](Cc1ccccc1)C(=O)N[C@@H](CCCNC(=N)N)C(=O)N1CCC[C@@H]1C(=O)N[C@H](Cc1c[nH]c2ccccc12)C(N)=O]

| Assay | Result |
| --- | --- |
| MC-4 Ki (average) | 10000 |
| MC-1 Ki (average) | 20 |
| MC-1 EC$_{50}$ (average; cAMP HBL) | 2 |
| MC-1 E$_{max}$ (average; cAMP HBL) | 72% |

9.13  Ac-Nle-Ala-His-D-Phe-Arg-Pro-D-Trp-NH$_2$ (SEQ ID NO:16)

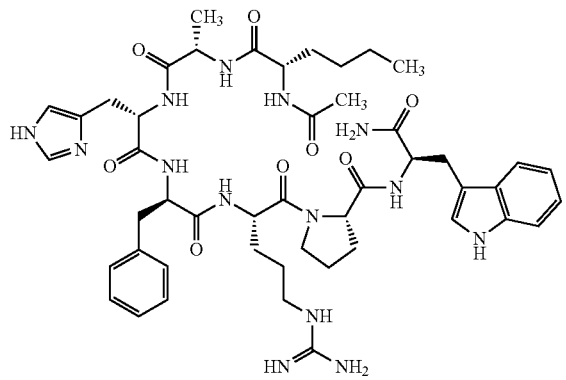 [SMILES: CCCC[C@H](NC(C)=O)C(=O)N[C@@H](C)C(=O)N[C@@H](Cc1c[nH]cn1)C(=O)N[C@H](Cc1ccccc1)C(=O)N[C@@H](CCCNC(=N)N)C(=O)N1CCC[C@H]1C(=O)N[C@H](Cc1c[nH]c2ccccc12)C(N)=O]

| Assay | Result |
| --- | --- |
| MC-4 Ki (average) | 650 |
| MC-1 Ki (average) | 2 |
| MC-1 EC$_{50}$ (average; cAMP HBL) | 0.17 |
| MC-1 E$_{max}$ (average; cAMP HBL) | 90% |

9.14 Ac-Nle-Ala-His-D-Phe-Arg-Ala-Trp-OH (SEQ ID NO:17)

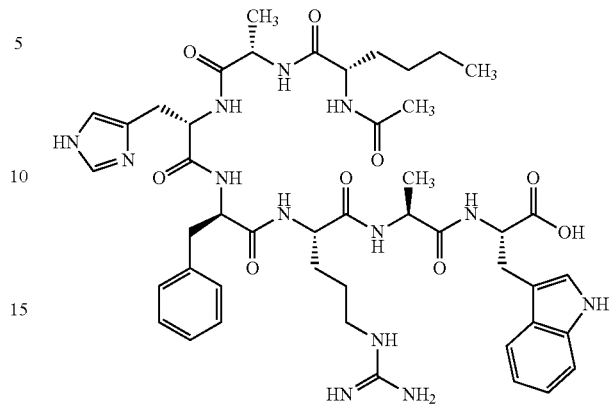

| Assay | Result |
| --- | --- |
| MC-4 Ki (average) | 7425 |
| MC-1 Ki (average) | 6 |
| MC-1 EC$_{50}$ (average; cAMP HBL) | 0.4 |
| MC-1 E$_{max}$ (average; cAMP HBL) | 73% |

9.15 Ac-Nle-D-Phe-Arg-Ala-Trp-NH$_2$ (SEQ ID NO:18)

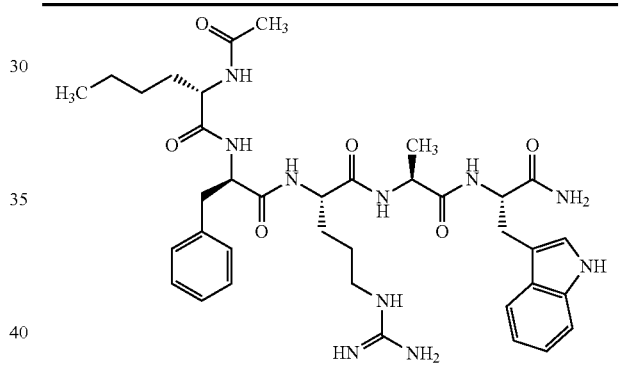

| Assay | Result |
| --- | --- |
| MC-4 Ki (average) | 7125 |
| MC-1 Ki (average) | 1290 |
| MC-1 EC$_{50}$ (average; cAMP HBL) | 402 |
| MC-1 E$_{max}$ (average; cAMP HBL) | 67% |

9.16 Ac-Nle-Ala-His-D-Phe-Ala-Ala-Trp-NH$_2$ (SEQ ID NO:19)

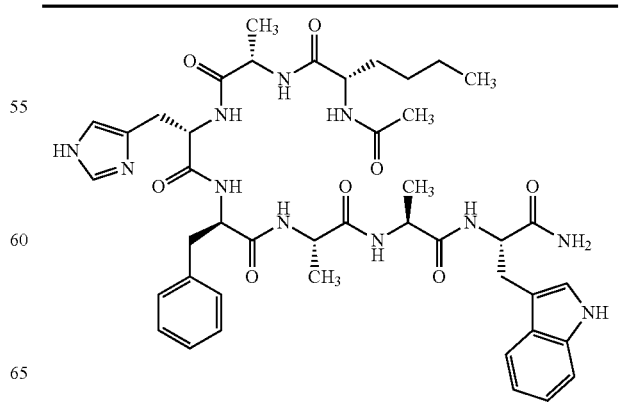

-continued

| Assay | Result |
|---|---|
| MC-4 Ki (average) | 10000 |
| MC-1 Ki (average) | 43 |
| MC-1 EC$_{50}$ (average; cAMP HBL) | 4 |
| MC-1 E$_{max}$ (average; cAMP HBL) | 99 |

9.17 Ac-Nle-Ala-Ala-D-Phe-Arg-Ala-Trp-NH$_2$ (SEQ ID NO:20)

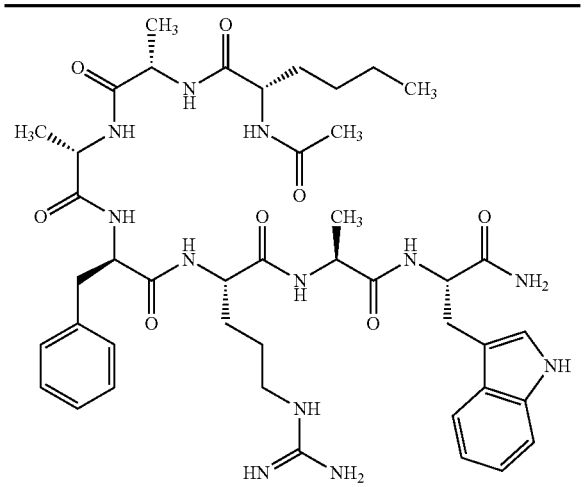

| Assay | Result |
|---|---|
| MC-4 Ki (average) | 10000 |
| MC-1 Ki (average) | 195 |
| MC-1 EC$_{50}$ (average; cAMP HBL) | 8 |
| MC-1 E$_{max}$ (average; cAMP HBL) | 94% |

9.18 Ac-Nle-Ala-Arg-D-Phe-Arg-Ala-Trp-NH$_2$ (SEQ ID NO:21)

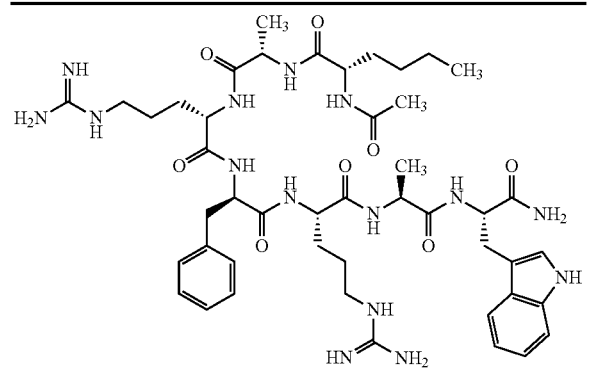

| Assay | Result |
|---|---|
| MC-4 Ki (average) | 1183 |
| MC-1 Ki (average) | 0.45 |
| MC-1 EC$_{50}$ (average; cAMP HBL) | 0.04 |
| MC-1 E$_{max}$ (average; cAMP HBL) | 106% |

9.19 Ac-Nle-Ala-Phe-D-Phe-Arg-Ala-Trp-NH$_2$ (SEQ ID NO:22)

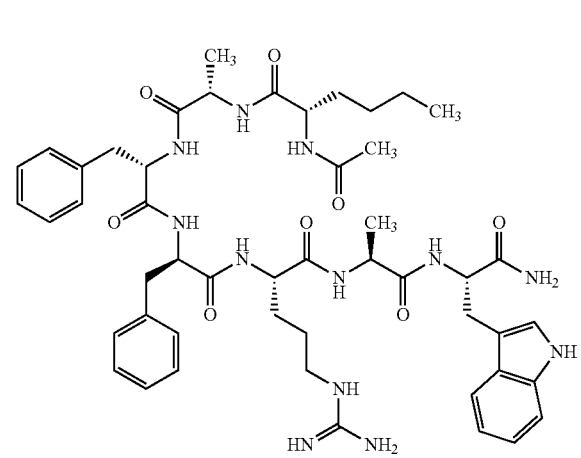 [SMILES: CCCC[C@H](NC(C)=O)C(=O)N[C@@H](C)C(=O)N[C@@H](Cc1ccccc1)C(=O)N[C@H](Cc1ccccc1)C(=O)N[C@@H](CCCNC(=N)N)C(=O)N[C@@H](C)C(=O)N[C@@H](Cc1c[nH]c2ccccc12)C(N)=O]

| Assay | Result |
|---|---|
| MC-4 Ki (average) | 1625 |
| MC-1 Ki (average) | 20 |
| MC-1 EC$_{50}$ (average; cAMP HBL) | 6 |
| MC-1 E$_{max}$ (average; cAMP HBL) | 99% |

9.20 Ac-Nle-Ala-Lys-D-Phe-Arg-Ala-Trp-NH$_2$ (SEQ ID NO:23)

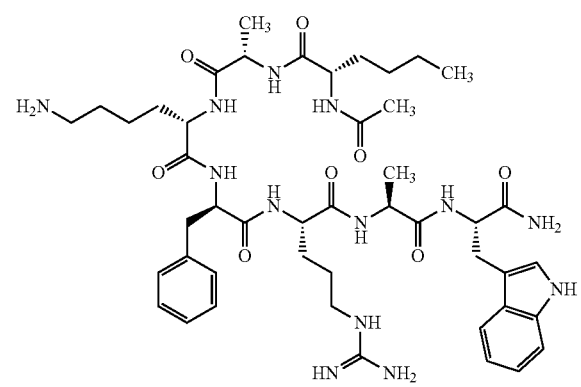 [SMILES: CCCC[C@H](NC(C)=O)C(=O)N[C@@H](C)C(=O)N[C@@H](CCCCN)C(=O)N[C@H](Cc1ccccc1)C(=O)N[C@@H](CCCNC(=N)N)C(=O)N[C@@H](C)C(=O)N[C@@H](Cc1c[nH]c2ccccc12)C(N)=O]

| Assay | Result |
|---|---|
| MC-4 Ki (average) | 10000 |
| MC-1 Ki (average) | 4 |
| MC-1 EC$_{50}$ (average; cAMP HBL) | 0.1 |
| MC-1 E$_{max}$ (average; cAMP HBL) | 107% |

9.21 Ac-Nle-Ala-Orn-D-Phe-Arg-Ala-Trp-NH$_2$ (SEQ ID NO:24)

9.22 Ac-Nle-Ala-Dab-D-Phe-Arg-Ala-Trp-NH$_2$ (SEQ ID NO:25)

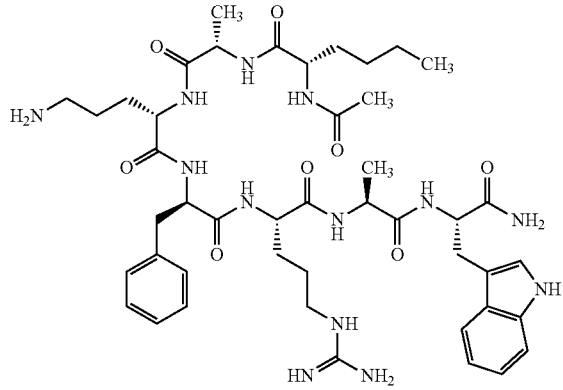 [SMILES: CCCC[C@H](NC(C)=O)C(=O)N[C@@H](C)C(=O)N[C@@H](CCCN)C(=O)N[C@H](Cc1ccccc1)C(=O)N[C@@H](CCCNC(=N)N)C(=O)N[C@@H](C)C(=O)N[C@@H](Cc1c[nH]c2ccccc12)C(N)=O]

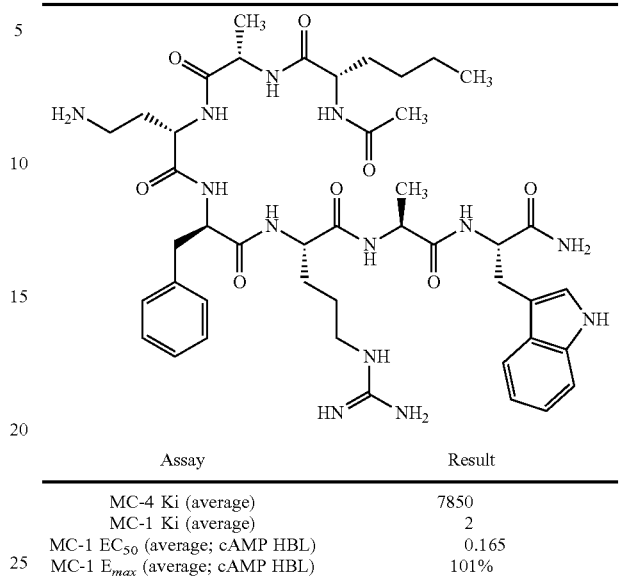

| Assay | Result |
|---|---|
| MC-4 Ki (average) | 7583 |
| MC-1 Ki (average) | 0.3 |
| MC-1 EC$_{50}$ (average; cAMP HBL) | 0.045 |
| MC-1 E$_{max}$ (average; cAMP HBL) | 107% |

| Assay | Result |
|---|---|
| MC-4 Ki (average) | 7850 |
| MC-1 Ki (average) | 2 |
| MC-1 EC$_{50}$ (average; cAMP HBL) | 0.165 |
| MC-1 E$_{max}$ (average; cAMP HBL) | 101% |

Although the invention has been described in detail with particular reference to these preferred embodiments, other embodiments can achieve the same results. Variations and modifications of the present invention will be obvious to those skilled in the art and it is intended to cover all such modifications and equivalents. The entire disclosures of all references, applications, patents, and publications cited above are hereby incorporated by reference.

We claim:

1. An isolated linear peptide of formula $$Z-Xaa^1-Xaa^2-Xaa^3-Xaa^4-Xaa^5-Xaa^6-Y$$

or a pharmaceutically acceptable salt thereof, wherein:
Z is a $C_1$ to $C_7$ acyl;
$Xaa^1$ is from one to three amino acid residues;
$Xaa^2$ is an L-isomer of Ala, His or Pro, optionally substituted with hydroxyl, halogen, sulfonamide, alkyl, —O-alkyl, aryl, alkyl-aryl, alkyl-O-aryl, alkyl-O-alkyl-aryl, or —O-aryl;
$Xaa^3$ is L- or D-Phe, optionally substituted with one or more substituents independently selected from halo, $(C_1-C_{10})$alkyl-halo, $(C_1-C_{10})$alkyl, $(C_1-C_{10})$alkoxy, ($C_1$-$C_{10}$)alkylthio, aryl, aryloxy, nitro, nitrile, sulfonamide, amino, monosubstituted amino, disubstituted amino, hydroxy, carboxy, and alkoxy-carbonyl;

Xaa$^4$ is an L-isomer of Arg, His, Ser, Thr, Lys, Cit, Met(O), Orn, Dap, or Dab;

Xaa$^5$ is Gly, Sar or Ala;

Xaa$^6$ is L- or D-Trp; and

Y is an amide.

2. The isolated linear peptide of claim 1, wherein

Xaa$^3$ is D-Phe, optionally substituted with one or more substituents independently selected from halo, ($C_1$-$C_{10}$)alkyl-halo, ($C_1$-$C_{10}$)alkyl, ($C_1$-$C_{10}$)alkoxy, ($C_1$-$C_{10}$)alkylthio, aryl, aryloxy, nitro, nitrile, sulfonamide, amino, monosubstituted amino, disubstituted amino, hydroxy, carboxy, and alkoxy-carbonyl; and Xaa$^6$ is L-Trp.

3. The isolated linear peptide of claim 1, wherein the isolated linear peptide is Ac-Nle-His-D-Phe-Arg-Ala-Trp-NH$_2$ (SEQ ID NO:6).

4. The isolated linear peptide of claim 1, wherein Xaa$^1$ is Gly or an L-isomer of Ala, Nle, Leu, Ile or Val.

5. A pharmaceutical composition comprising a linear peptide or pharmaceutically acceptable salt thereof of claim 1 and a pharmaceutically acceptable carrier.

6. A linear peptide selected from the group consisting of

```
                                        (SEQ ID NO: 4)
Ac-Nle-Ala-His-D-Phe-Arg-Ala-Trp-NH2, (SEQ ID NO: 6)
Ac-Nle-His-D-Phe-Arg-Ala-Trp-NH2, (SEQ ID NO: 7)
Ac-Nle-Ala-His-D-Phe-Arg-Sar-Trp-NH2, (SEQ ID NO: 8)
Ac-Nle-Ala-His-D-Phe-Arg-Gly-Trp-NH2, (SEQ ID NO: 9)
Ac-Nle-Ala-His-Phe-Arg-Ala-Trp-NH2, (SEQ ID NO: 10)
Ac-Nle-Ala-His-Phe-Arg-Gly-Trp-NH2, (SEQ ID NO: 12)
Ac-Nle-Ala-His-D-Phe-Arg-Ala-D-Trp-NH2, (SEQ ID NO: 17)
Ac-Nle-Ala-His-D-Phe-Arg-Ala-Trp-OH, (SEQ ID NO: 18)
Ac-Nle-D-Phe-Arg-Ala-Trp-NH2, (SEQ ID NO: 19)
Ac-Nle-Ala-His-D-Phe-Ala-Ala-Trp-NH2, (SEQ ID NO: 20)
Ac-Nle-Ala-Ala-D-Phe-Arg-Ala-Trp-NH2, (SEQ ID NO: 21)
Ac-Nle-Ala-Arg-D-Phe-Arg-Ala-Trp-NH2, (SEQ ID NO: 22)
Ac-Nle-Ala-Phe-D-Phe-Arg-Ala-Trp-NH2, (SEQ ID NO: 23)
Ac-Nle-Ala-Lys-D-Phe-Arg-Ala-Trp-NH2, (SEQ ID NO: 24)
Ac-Nle-Ala-Orn-D-Phe-Arg-Ala-Trp-NH2,
and
                                        (SEQ ID NO: 25)
Ac-Nle-Ala-Dab-D-Phe-Arg-Ala-Trp-NH2.
```

7. A pharmaceutical composition comprising a linear peptide of claim 6 or pharmaceutically acceptable salt thereof and a pharmaceutically acceptable carrier.

* * * * *

SEQUENCE LISTING

```
<160> NUMBER OF SEQ ID NOS: 25

<210> SEQ ID NO 1
<211> LENGTH: 4
<212> TYPE: PRT
<213> ORGANISM: Homo sapiens

<400> SEQUENCE: 1

His Phe Arg Trp
1

<210> SEQ ID NO 2
<211> LENGTH: 13
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (13)..(13)
<223> OTHER INFORMATION: AMIDATION

<400> SEQUENCE: 2

Ser Tyr Ser Met Glu His Phe Arg Trp Gly Lys Pro Val
1               5                   10

<210> SEQ ID NO 3
<211> LENGTH: 13
```

```
<212> TYPE: PRT
<213> ORGANISM: Artificial Sequence
<220> FEATURE:
<223> OTHER INFORMATION: Synthetic analog of SEQ ID NO:2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: Nle
<220> FEATURE:
<221> NAME/KEY: MISC_FEATURE
<222> LOCATION: (7)..(7)
<223> OTHER INFORMATION: D-Phe
<220> FEATURE:
<221> NAME/KEY: MOD_RES
<222> LOCATION: (13)..(13)
<223> OTHER INFORMATION: AMIDATION

<400> SEQUENCE: 3

Ser Tyr Ser Xaa Glu His Xaa Arg Trp Gly Lys Pro Val
1               5                   10

<210> SEQ ID NO 4
<211> LENGTH: 7
<212> TYPE: PRT
<213> ORGANISM: Artificial Sequence
<220> FEATURE:
<223> OTHER INFORMATION: Synthetic melanocortin-1 receptor-specific
      peptide of invention
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MISC_FEATURE
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: AMIDATION

<400> SEQUENCE: 4

Xaa Ala His Xaa Arg Ala Trp
1               5

<210> SEQ ID NO 5
<211> LENGTH: 7
<212> TYPE: PRT
<213> ORGANISM: Artificial Sequence
<220> FEATURE:
<223> OTHER INFORMATION: Synthetic melanocortin-1 receptor-specific
      peptide of invention
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MISC_FEATURE
<222> LOCATION: (4)..(4)
<223> OTHER INFORMATION: D-Phe
<220> FEATURE:
<221> NAME/KEY: MOD_RES
<222> LOCATION: (7)..(7)
```

<223> OTHER INFORMATION: AMIDATION

<400> SEQUENCE: 5

Xaa Ala His Xaa Arg Pro Trp
1               5

<210> SEQ ID NO 6
<211> LENGTH: 6
<212> TYPE: PRT
<213> ORGANISM: Artificial Sequence
<220> FEATURE:
<223> OTHER INFORMATION: Synthetic melanocortin-1 receptor-specific
      peptide of invention
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MISC_FEATURE
<222> LOCATION: (3)..(3)
<223> OTHER INFORMATION: D-Phe
<220> FEATURE:
<221> NAME/KEY: MOD_RES
<222> LOCATION: (6)..(6)
<223> OTHER INFORMATION: AMIDATION

<400> SEQUENCE: 6

Xaa His Xaa Arg Ala Trp
1               5

<210> SEQ ID NO 7
<211> LENGTH: 7
<212> TYPE: PRT
<213> ORGANISM: Artificial Sequence
<220> FEATURE:
<223> OTHER INFORMATION: Synthetic melanocortin-1 receptor-specific
      peptide of invention
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MISC_FEATURE
<222> LOCATION: (4)..(4)
<223> OTHER INFORMATION: D-Phe
<220> FEATURE:
<221> NAME/KEY: MISC_FEATURE
<222> LOCATION: (6)..(6)
<223> OTHER INFORMATION: Sar
<220> FEATURE:
<221> NAME/KEY: MOD_RES
<222> LOCATION: (7)..(7)
<223> OTHER INFORMATION: AMIDATION

<400> SEQUENCE: 7

Xaa Ala His Xaa Arg Xaa Trp
1               5

<210> SEQ ID NO 8
<211> LENGTH: 7
<212> TYPE: PRT
<213> ORGANISM: Artificial Sequence
<220> FEATURE:
<223> OTHER INFORMATION: Synthetic melanocortin-1 receptor-specific
      peptide of invention

```
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MISC_FEATURE
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: AMIDATION

<400> SEQUENCE: 8

Xaa Ala His Xaa Arg Gly Trp
1               5

<210> SEQ ID NO 9
<211> LENGTH: 7
<212> TYPE: PRT
<213> ORGANISM: Artificial Sequence
<220> FEATURE:
<223> OTHER INFORMATION: Synthetic melanocortin-1 receptor-specific
      peptide of invention
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (7)..(7)
<223> OTHER INFORMATION: AMIDATION

<400> SEQUENCE: 9

Xaa Ala His Phe Arg Ala Trp
1               5

<210> SEQ ID NO 10
<211> LENGTH: 7
<212> TYPE: PRT
<213> ORGANISM: Artificial Sequence
<220> FEATURE:
<223> OTHER INFORMATION: Synthetic melanocortin-1 receptor-specific
      peptide of invention
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (7)..(7)
<223> OTHER INFORMATION: AMIDATION

<400> SEQUENCE: 10

Xaa Ala His Phe Arg Gly Trp
1               5

<210> SEQ ID NO 11
<211> LENGTH: 6
<212> TYPE: PRT
<213> ORGANISM: Artificial Sequence
```

```
<220> FEATURE:
<223> OTHER INFORMATION: Synthetic melanocortin-1 receptor-specific
      peptide of invention
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (6)..(6)
<223> OTHER INFORMATION: AMIDATION

<400> SEQUENCE: 11

Xaa His Phe Arg Ala Trp
1               5

<210> SEQ ID NO 12
<211> LENGTH: 7
<212> TYPE: PRT
<213> ORGANISM: Artificial Sequence
<220> FEATURE:
<223> OTHER INFORMATION: Synthetic melanocortin-1 receptor-specific
      peptide of invention
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MISC_FEATURE
<222> LOCATION: (4)..(4)
<223> OTHER INFORMATION: D-Phe
<220> FEATURE:
<221> NAME/KEY: MISC_FEATURE
<222> LOCATION: (7)..(7)
<223> OTHER INFORMATION: D-Trp
<220> FEATURE:
<221> NAME/KEY: MOD_RES
<222> LOCATION: (7)..(7)
<223> OTHER INFORMATION: AMIDATION

<400> SEQUENCE: 12

Xaa Ala His Xaa Arg Ala Xaa
1               5

<210> SEQ ID NO 13
<211> LENGTH: 6
<212> TYPE: PRT
<213> ORGANISM: Artificial Sequence
<220> FEATURE:
<223> OTHER INFORMATION: Synthetic melanocortin-1 receptor-specific
      peptide of invention
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MISC_FEATURE
<222> LOCATION: (3)..(3)
<223> OTHER INFORMATION: D-Phe
<220> FEATURE:
<221> NAME/KEY: MOD_RES
<222> LOCATION: (6)..(6)
<223> OTHER INFORMATION: AMIDATION
```

```
<400> SEQUENCE: 13

Xaa Ala Xaa Arg Ala Trp
1               5

<210> SEQ ID NO 14
<211> LENGTH: 7
<212> TYPE: PRT
<213> ORGANISM: Artificial Sequence
<220> FEATURE:
<223> OTHER INFORMATION: Synthetic melanocortin-1 receptor-specific
      peptide of invention
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MISC_FEATURE
<222> LOCATION: (4)..(4)
<223> OTHER INFORMATION: D-Phe
<220> FEATURE:
<221> NAME/KEY: MISC_FEATURE
<222> LOCATION: (6)..(6)
<223> OTHER INFORMATION: D-Pro
<220> FEATURE:
<221> NAME/KEY: MOD_RES
<222> LOCATION: (7)..(7)
<223> OTHER INFORMATION: AMIDATION

<400> SEQUENCE: 14

Xaa Ala His Xaa Arg Xaa Trp
1               5

<210> SEQ ID NO 15
<211> LENGTH: 7
<212> TYPE: PRT
<213> ORGANISM: Artificial Sequence
<220> FEATURE:
<223> OTHER INFORMATION: Synthetic melanocortin-1 receptor-specific
      peptide of invention
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MISC_FEATURE
<222> LOCATION: (4)..(4)
<223> OTHER INFORMATION: D-Phe
<220> FEATURE:
<221> NAME/KEY: MISC_FEATURE
<222> LOCATION: (6)..(6)
<223> OTHER INFORMATION: D-Pro
<220> FEATURE:
<221> NAME/KEY: MISC_FEATURE
<222> LOCATION: (7)..(7)
<223> OTHER INFORMATION: D-Trp
<220> FEATURE:
<221> NAME/KEY: MOD_RES
<222> LOCATION: (7)..(7)
<223> OTHER INFORMATION: AMIDATION

<400> SEQUENCE: 15

Xaa Ala His Xaa Arg Xaa Xaa
1               5
```

```
<210> SEQ ID NO 16
<211> LENGTH: 7
<212> TYPE: PRT
<213> ORGANISM: Artificial Sequence
<220> FEATURE:
<223> OTHER INFORMATION: Synthetic melanocortin-1 receptor-specific
      peptide of invention
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MISC_FEATURE
<222> LOCATION: (4)..(4)
<223> OTHER INFORMATION: D-Phe
<220> FEATURE:
<221> NAME/KEY: MISC_FEATURE
<222> LOCATION: (7)..(7)
<223> OTHER INFORMATION: D-Trp
<220> FEATURE:
<221> NAME/KEY: MOD_RES
<222> LOCATION: (7)..(7)
<223> OTHER INFORMATION: AMIDATION

<400> SEQUENCE: 16

Xaa Ala His Xaa Arg Pro Xaa
1               5

<210> SEQ ID NO 17
<211> LENGTH: 7
<212> TYPE: PRT
<213> ORGANISM: Artificial Sequence
<220> FEATURE:
<223> OTHER INFORMATION: Synthetic melanocortin-1 receptor-specific
      peptide of invention
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MISC_FEATURE
<222> LOCATION: (4)..(4)
<223> OTHER INFORMATION: D-Phe

<400> SEQUENCE: 17

Xaa Ala His Xaa Arg Ala Trp
1               5

<210> SEQ ID NO 18
<211> LENGTH: 5
<212> TYPE: PRT
<213> ORGANISM: Artificial Sequence
<220> FEATURE:
<223> OTHER INFORMATION: Synthetic melanocortin-1 receptor-specific
      peptide of invention
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MISC_FEATURE
<222> LOCATION: (2)..(2)
<223> OTHER INFORMATION: D-Phe
```

```
<220> FEATURE:
<221> NAME/KEY: MOD_RES
<222> LOCATION: (5)..(5)
<223> OTHER INFORMATION: AMIDATION

<400> SEQUENCE: 18

Xaa Xaa Arg Ala Trp
1               5

<210> SEQ ID NO 19
<211> LENGTH: 7
<212> TYPE: PRT
<213> ORGANISM: Artificial Sequence
<220> FEATURE:
<223> OTHER INFORMATION: Synthetic melanocortin-1 receptor-specific
      peptide of invention
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MISC_FEATURE
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: AMIDATION

<400> SEQUENCE: 19

Xaa Ala His Xaa Ala Ala Trp
1               5

<210> SEQ ID NO 20
<211> LENGTH: 7
<212> TYPE: PRT
<213> ORGANISM: Artificial Sequence
<220> FEATURE:
<223> OTHER INFORMATION: Synthetic melanocortin-1 receptor-specific
      peptide of invention
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MISC_FEATURE
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: AMIDATION

<400> SEQUENCE: 20

Xaa Ala Ala Xaa Arg Ala Trp
1               5

<210> SEQ ID NO 21
<211> LENGTH: 7
<212> TYPE: PRT
<213> ORGANISM: Artificial Sequence
<220> FEATURE:
<223> OTHER INFORMATION: Synthetic melanocortin-1 receptor-specific
      peptide of invention
<220> FEATURE:
```

```
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MISC_FEATURE
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: AMIDATION

<400> SEQUENCE: 21

Xaa Ala Arg Xaa Arg Ala Trp
1               5

<210> SEQ ID NO 22
<211> LENGTH: 7
<212> TYPE: PRT
<213> ORGANISM: Artificial Sequence
<220> FEATURE:
<223> OTHER INFORMATION: Synthetic melanocortin-1 receptor-specific
      peptide of invention
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MISC_FEATURE
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: AMIDATION

<400> SEQUENCE: 22

Xaa Ala Phe Xaa Arg Ala Trp
1               5

<210> SEQ ID NO 23
<211> LENGTH: 7
<212> TYPE: PRT
<213> ORGANISM: Artificial Sequence
<220> FEATURE:
<223> OTHER INFORMATION: Synthetic melanocortin-1 receptor-specific
      peptide of invention
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MISC_FEATURE
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: AMIDATION

<400> SEQUENCE: 23

Xaa Ala Lys Xaa Arg Ala Trp
```

```
<210> SEQ ID NO 24
<211> LENGTH: 7
<212> TYPE: PRT
<213> ORGANISM: Artificial Sequence
<220> FEATURE:
<223> OTHER INFORMATION: Synthetic melanocortin-1 receptor-specific
      peptide of invention
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (3)..(3)
<223> OTHER INFORMATION: Orn
<220> FEATURE:
<221> NAME/KEY: MISC_FEATURE
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: AMIDATION

<400> SEQUENCE: 24

Xaa Ala Xaa Xaa Arg Ala Trp
1               5

<210> SEQ ID NO 25
<211> LENGTH: 7
<212> TYPE: PRT
<213> ORGANISM: Artificial Sequence
<220> FEATURE:
<223> OTHER INFORMATION: Synthetic melanocortin-1 receptor-specific
      peptide of invention
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MISC_FEATURE
<222> LOCATION: (3)..(3)
<223> OTHER INFORMATION: Dab
<220> FEATURE:
<221> NAME/KEY: MISC_FEATURE
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: AMIDATION

<400> SEQUENCE: 25

Xaa Ala Xaa Xaa Arg Ala Trp
1               5
```